United States Patent
Bryan et al.

(10) Patent No.: US 6,682,899 B2
(45) Date of Patent: Jan. 27, 2004

(54) APPARATUS AND METHOD FOR DETECTING AND IDENTIFYING INFECTIOUS AGENTS

(75) Inventors: Bruce J. Bryan, Beverly Hills, CA (US); Stephen Gaalema, Colorado Springs, CO (US); Randall B. Murphy, Irvington, NY (US)

(73) Assignee: Prolume, Ltd., Beverly Hills, CA (US)

( * ) Notice: Subject to any disclaimer, the term of this patent is extended or adjusted under 35 U.S.C. 154(b) by 31 days.

(21) Appl. No.: 10/126,777

(22) Filed: Apr. 19, 2002

(65) Prior Publication Data

US 2003/0113741 A1 Jun. 19, 2003

Related U.S. Application Data

(62) Division of application No. 08/990,103, filed on Dec. 12, 1997, now Pat. No. 6,458,547.
(60) Provisional application No. 60/037,675, filed on Feb. 11, 1997, and provisional application No. 60/033,745, filed on Dec. 12, 1996.

(51) Int. Cl.[7] ............ G01N 33/53; G01N 33/543; G01N 21/00; G01N 33/552; C12M 1/34
(52) U.S. Cl. ............ 435/7.1; 435/4; 435/6; 435/7.9; 435/7.92; 435/283.1; 435/288.7; 435/808; 435/973; 435/975; 436/164; 436/172; 436/518; 436/524; 436/527; 436/805; 422/57; 422/58; 422/68.1; 422/82.05; 422/82.08; 356/215; 356/222; 356/317; 427/8; 427/162; 427/167

(58) Field of Search ............ 435/4, 6, 7.1, 7.9, 435/7.92, 283.1, 288.7, 808, 973, 975; 436/164, 172, 518, 524, 527, 805; 422/58, 68.1, 82.05, 82.08, 57; 356/215, 222, 317; 427/8, 162, 167

(56) References Cited

U.S. PATENT DOCUMENTS 5,364,797 A * 11/1994 Olson et al. ............ 436/501

* cited by examiner

Primary Examiner—Long V. Le
Assistant Examiner—Kartic Padmanabhan
(74) Attorney, Agent, or Firm—Alan G. Towner, Esq.; Pietragallo, Bosick & Gordon

(57) ABSTRACT

Solid phase methods for the identification of an analyte in a biological medium, such as a body fluid, using bioluminescence are provided. A chip designed for performing the method and detecting the bioluminescence is also provided. Methods employing biomineralization for depositing silicon on a matrix support are also provided. A synthetic synapse is also provided.

1 Claim, 19 Drawing Sheets

COMPONENTS OF CHIP:

A: CCD SILICON CHARGE COUPLE DEVICE   (OTHER CCD'S CAN BE USED DEPENDENT UPON EMITTED LIGHT WAVELENGTH FROM LUCIFERASE)

REFLECTIVE ANTIBODY SURFACE/REACTION SURFACE
AN EXAMPLE WOULD BE A HEAT STABLE MYLAR REFLECTOR

[MICROSCOPIC VIEW]

ARRAY OF REACTIVE SURFACES TO FIT ON "CHIP"

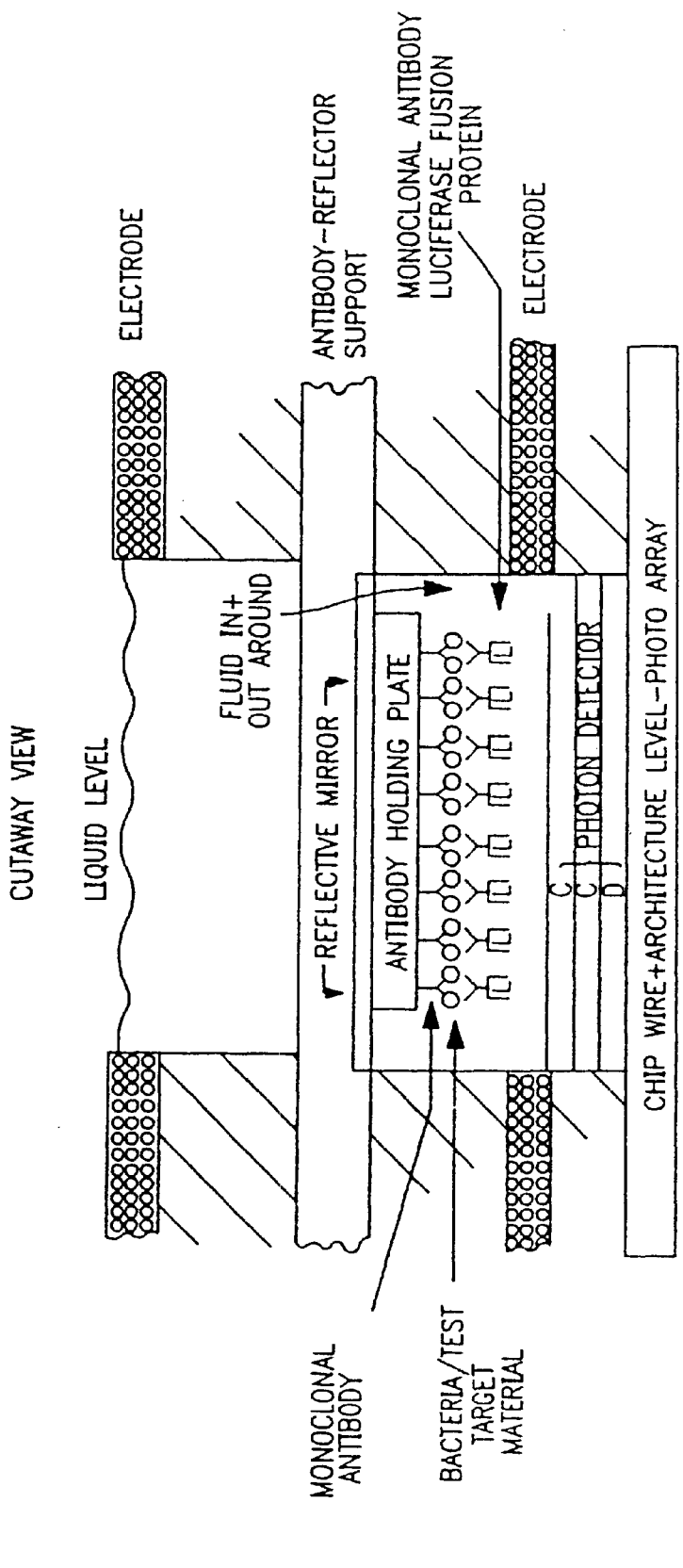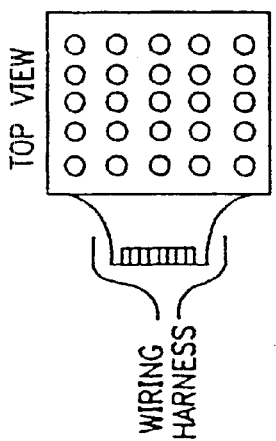
FIG. 11

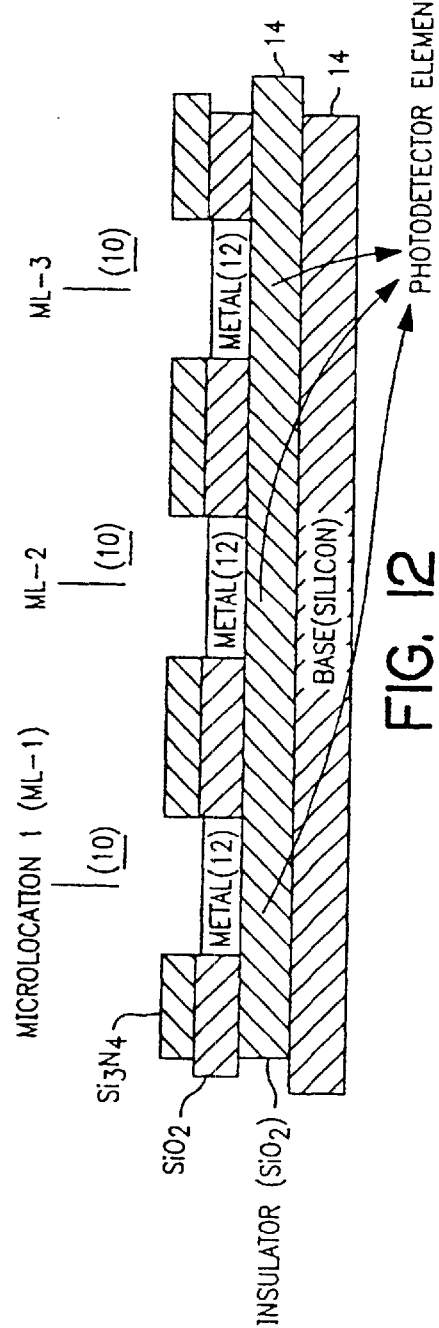
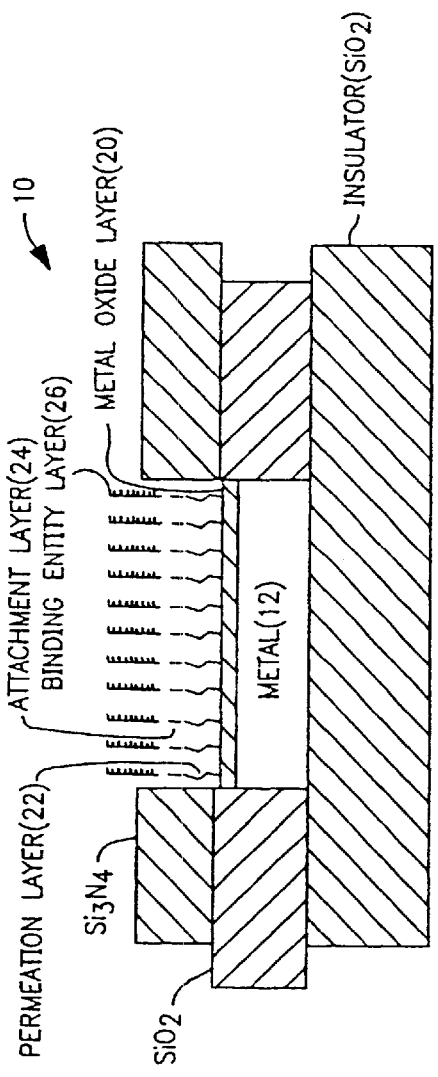

PLACEMENT OF SILICON SYNAPSE ELECTRODES (1) PLACEMENT OF ELECTRODES INTO THE CORRECT STEREOTAXIC LOCATIONS CAN BE ACHIEVED BY MRI LOCALIZATION.

(2) LASER MICROHOLES CAN BE DRILLED INTO THE SPINAL CORD WITH SUITABLE $CO_2$ OR OTHER LASER (3) PLACEMENT WOULD BE FROM SUPERFICIAL TO DEEP ALONG THE KNOWN PATHWAYS AND THERE COULD BE SEVERAL WIRES LEADING TO THE COMPUTER. RT/LT/LAT ↔ MED/VENT ↔ DORSAL AT FIRST 2 CHANNELS ON EACH SIDE BUT MANY MORE COULD BE PLACED (4) MUSCLE MOVEMENTS COULD BE INITIATED BY INSERTION OF PERMANENT ELECTRODES INTO VARIOUS MUSCLE BUNDLES (5) THE PATIENT WILL CONTROL THE OUTPUT BY THINKING ABOUT IT AND THEREBY RELEARNING MOTOR SKILLS, SUCH AS WALKING

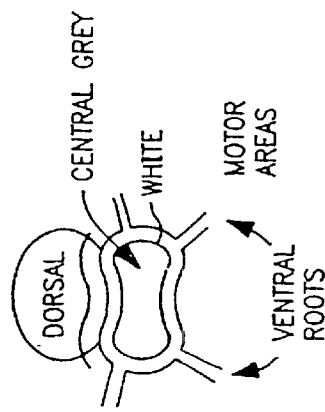

SPINAL CROSS-SECTION

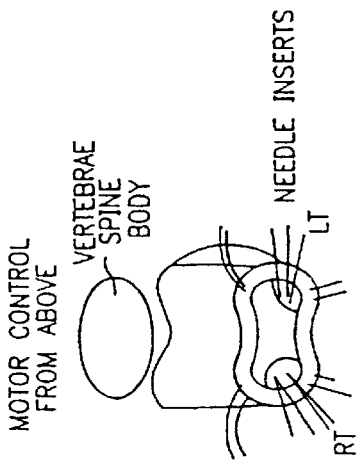

MOTOR CONTROL FROM ABOVE

FIG. 19

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
        (A) LENGTH: 1196 base pairs
        (B) TYPE: nucleic acid
        (C) STRANDEDNESS: single
        (D) TOPOLOGY: linear (ii) MOLECULE TYPE: cDNA (vi) ORIGINAL SOURCE:

(ix) FEATURE:
        (A) NAME/KEY: Coding Sequence
        (B) LOCATION: 1...942
        (D) OTHER INFORMATION: Renilla Reinformis Luciferase (x) PUBLICATION INFORMATION:
        (H) DOCUMENT NUMBER: 5,418,155

(xi) SEQUENCE DESCRIPTION: SEQ ID NO: 1:

```
AGC TTA AAG ATG ACT TCG AAA GTT TAT GAT CCA GAA CAA AGG AAA CGG      48
Ser Leu Lys Met Thr Ser Lys Val Tyr Asp Pro Glu Gln Arg Lys Arg
 1               5                  10                  15

ATG ATA ACT GGT CCG CAG TGG TGG GCC AGA TGT AAA CAA ATG AAT GTT      96
Met Ile Thr Gly Pro Gln Trp Trp Ala Arg Cys Lys Gln Met Asn Val
                20                  25                  30

CTT GAT TCA TTT ATT AAT TAT TAT GAT TCA GAA AAA CAT GCA GAA AAT     144
Leu Asp Ser Phe Ile Asn Tyr Tyr Asp Ser Glu Lys His Ala Glu Asn
                35                  40                  45

GCT GTT ATT TTT TTA CAT GGT AAC GCG GCC TCT TCT TAT TTA TGG CGA     192
Ala Val Ile Phe Leu His Gly Asn Ala Ala Ser Ser Tyr Leu Trp Arg
                50                  55                  60
```

```
CAT GTT GTG CCA CAT ATT GAG CCA GTA GCG CGG TGT ATT ATA CCA GAT       240
His Val Val Pro His Ile Glu Pro Val Ala Arg Cys Ile Ile Pro Asp
 65              70                  75                  80

CTT ATT GGT ATG GGC AAA TCA GGC AAA TCT GGT AAT GGT TCT TAT AGG       288
Leu Ile Gly Met Gly Lys Ser Gly Lys Ser Gly Asn Gly Ser Tyr Arg
                 85                  90                  95

TTA CTT GAT CAT TAC AAA TAT CTT ACT GCA TGG TTG AAC TTC TTA ATT       336
Leu Leu Asp His Tyr Lys Tyr Leu Thr Ala Trp Leu Asn Phe Leu Ile
                100                 105                 110

TAC CAA AGA AGA TCA TTT TTT GTC GGC CAT GAT TGG GGT GCT TGT TTG       384
Tyr Gln Arg Arg Ser Phe Phe Val Gly His Asp Trp Gly Ala Cys Leu
                115                 120                 125

GCA TTT CAT TAT AGC TAT GAG CAT CAA GAT AAG ATC AAA GCA ATA GTT       432
Ala Phe His Tyr Ser Tyr Glu His Gln Asp Lys Ile Lys Ala Ile Val
        130                 135                 140

CAC GCT GAA AGT GTA GTA GAT GTG ATT GAA TCA TGG GAT GAA TGG CCT       480
His Ala Glu Ser Val Val Asp Val Ile Glu Ser Trp Asp Glu Trp Pro
145                 150                 155                 160

GAT ATT GAA GAA GAT ATT GCG TTG ATC AAA TCT GAA GAA GGA GAA AAA       528
Asp Ile Glu Glu Asp Ile Ala Leu Ile Lys Ser Glu Glu Gly Glu Lys
                165                 170                 175

ATG GTT TTG GAG AAT AAC TTC TTC GTG GAA ACC ATG TTG CCA TCA AAA       576
Met Val Leu Glu Asn Asn Phe Phe Val Glu Thr Met Leu Pro Ser Lys
                180                 185                 190

ATC ATG AGA AAG TTA GAA CCA GAA GAA TTT GCA GCA TAT CTT GAA CCA       624
Ile Met Arg Lys Leu Glu Pro Glu Glu Phe Ala Ala Tyr Leu Glu Pro
        195                 200                 205

TTC AAA GAG AAA GGT GAA GTT CGT CGT CCA ACA TTA TCA TGG CCT CGT       672
Phe Lys Glu Lys Gly Glu Val Arg Arg Pro Thr Leu Ser Trp Pro Arg
210                 215                 220

GAA ATC CCG TTA GTA AAA GGT GGT AAA CCT GAC GTT GTA CAA ATT GTT       720
Glu Ile Pro Leu Val Lys Gly Gly Lys Pro Asp Val Val Gln Ile Val
225                 230                 235                 240

AGG AAT TAT AAT GCT TAT CTA CGT GCA AGT GAT GAT TTA CCA AAA ATG       768
Arg Asn Tyr Asn Ala Tyr Leu Arg Ala Ser Asp Asp Leu Pro Lys Met
                245                 250                 255

TTT ATT GAA TCG GAT CCA GGA TTC TTT TCC AAT GCT ATT GTT GAA GGC       816
Phe Ile Glu Ser Asp Pro Gly Phe Phe Ser Asn Ala Ile Val Glu Gly
                260                 265                 270

GCC AAG AAG TTT CCT AAT ACT GAA TTT GTC AAA GTA AAA GGT CTT CAT       864
Ala Lys Lys Phe Pro Asn Thr Glu Phe Val Lys Val Lys Gly Leu His
        275                 280                 285

TTT TCG CAA GAA GAT GCA CCT GAT GAA ATG GGA AAA TAT ATC AAA TCG       912
Phe Ser Gln Glu Asp Ala Pro Asp Glu Met Gly Lys Tyr Ile Lys Ser
        290                 295                 300

TTC GTT GAG CGA GTT CTC AAA AAT GAA CAA TAA TTACTTTGGT TTTTTATTTA     965
Phe Val Glu Arg Val Leu Lys Asn Glu Gln
305                 310

CATTTTTCCC GGGTTAATA ATATAAATGT CATTTTCAAC AATTTTATTT TAACTGAATA    1025

TTTCACAGGG AACATTCATA TATGTTGATT AATTTAGCTC GAACTTTACT CTGTCATATC    1085

ATTTTGGAAT ATTACCTCTT TCAATGAAAC TTTATAAACA GTGGTTCAAT TAATTAATAT    1145

ATATTATAAT TACATTTGTT ATGTAATAAA CTCGGTTTTA TTATAAAAAA A             1196
```

(2) INFORMATION FOR SEQ ID NO: 2:

(i) SEQUENCE CHARACTERISTICS:
        (A) LENGTH: 1822 base pairs
        (B) TYPE: nucleic acid
        (C) STRANDEDNESS: single (D) TOPOLOGY: linear (ii) MOLECULE TYPE: cDNA (ix) FEATURE:
            (A) NAME/KEY: Coding Sequence
            (B) LOCATION: 1...1665
            (D) OTHER INFORMATION: Cypridina hilgendorfii luciferase (x) PUBLICATION INFORMATION:
            (H) DOCUMENT NUMBER: EP 0 387 355 TORAY (xi) SEQUENCE DESCRIPTION: SEQ ID NO: 2:

```
ATG AAG CTA ATA ATT CTG TCT ATT ATA TTG GCC TAC TGT GTC ACA GTC        48
Met Lys Leu Ile Ile Leu Ser Ile Ile Leu Ala Tyr Cys Val Thr Val
 1               5                  10                  15

AAC TGC CAG GAT GCA TGT CCT GTA GAA GCT GAA GCA CCG TCA AGT ACA        96
Asn Cys Gln Asp Ala Cys Pro Val Glu Ala Glu Ala Pro Ser Ser Thr
             20                  25                  30

CCA ACA GTC CCA ACA TCT TGT GAA GCT AAA GAA GGA GAA TGT ATC GAT       144
Pro Thr Val Pro Thr Ser Cys Glu Ala Lys Glu Gly Glu Cys Ile Asp
         35                  40                  45

ACC AGA TGC GCA ACA TGT AAA CGA GAC ATA CTA TCA GAC GGA CTG TGT       192
Thr Arg Cys Ala Thr Cys Lys Arg Asp Ile Leu Ser Asp Gly Leu Cys
     50                  55                  60

GAA AAT AAA CCA GGG AAG ACA TGC TGT AGA ATG TGC CAG TAT GTA ATT       240
Glu Asn Lys Pro Gly Lys Thr Cys Cys Arg Met Cys Gln Tyr Val Ile
 65                  70                  75                  80

GAA TCC AGA GTA GAA GCT GCT GGA TAT TTT AGA ACG TTT TAC GCC AAA       288
Glu Ser Arg Val Glu Ala Ala Gly Tyr Phe Arg Thr Phe Tyr Ala Lys
                 85                  90                  95

AGA TTT AAT TTT CAG GAA CCT GGT AAA TAT GTG CTG GCT CGA GGA ACC       336
Arg Phe Asn Phe Gln Glu Pro Gly Lys Tyr Val Leu Ala Arg Gly Thr
             100                 105                 110

AAG GGT GGC GAC TGG TCT GTA ACC CTC ACC ATG GAG AAT CTA GAT GGA       384
Lys Gly Gly Asp Trp Ser Val Thr Leu Thr Met Glu Asn Leu Asp Gly
         115                 120                 125

CAG AAG GGA GCT GTA CTG ACT AAG ACA ACA CTG GAG GTA GTA GGA GAC       432
Gln Lys Gly Ala Val Leu Thr Lys Thr Thr Leu Glu Val Val Gly Asp
     130                 135                 140

GTA ATA GAC ATT ACT CAA GCT ACT GCA GAT CCT ATC ACA GTT AAC GGA       480
Val Ile Asp Ile Thr Gln Ala Thr Ala Asp Pro Ile Thr Val Asn Gly
145                 150                 155                 160

GGA GCT GAC CCA GTT ATC GCT AAC CCG TTC ACA ATT GGT GAG GTG ACC       528
Gly Ala Asp Pro Val Ile Ala Asn Pro Phe Thr Ile Gly Glu Val Thr
                 165                 170                 175

ATT GCT GTT GTC GAA ATA CCC GGC TTC AAT ATT ACA GTC ATC GAA TTC       576
Ile Ala Val Val Glu Ile Pro Gly Phe Asn Ile Thr Val Ile Glu Phe
             180                 185                 190

TTT AAA CTA ATC GTG ATA GAT ATT CTG GGA GGA AGA TCT GTG AGA ATT       624
Phe Lys Leu Ile Val Ile Asp Ile Leu Gly Gly Arg Ser Val Arg Ile
         195                 200                 205

GCT CCA GAC ACA GCA AAC AAA GGA CTG ATA TCT GGT ATC TGT GGT AAT       672
Ala Pro Asp Thr Ala Asn Lys Gly Leu Ile Ser Gly Ile Cys Gly Asn
     210                 215                 220

CTG GAG ATG AAT GAC GCT GAT GAC TTT ACT ACA GAC GCA GAT CAG CTG       720
Leu Glu Met Asn Asp Ala Asp Asp Phe Thr Thr Asp Ala Asp Gln Leu
225                 230                 235                 240

GCG ATC CAA CCC AAC ATA AAC AAA GAG TTC GAC GGC TGC CCA TTC TAC       768
Ala Ile Gln Pro Asn Ile Asn Lys Glu Phe Asp Gly Cys Pro Phe Tyr
                 245                 250                 255

GGG AAT CCT TCT GAT ATC GAA TAC TGC AAA GGT CTC ATG GAG CCA TAC       816
Gly Asn Pro Ser Asp Ile Glu Tyr Cys Lys Gly Leu Met Glu Pro Tyr
```

```
                Gly Asn Pro Ser Asp Ile Glu Tyr Cys Lys Gly Leu Met Glu Pro Tyr
                            260                 265                 270

AGA GCT GTA TGT CGT AAC AAT ATC AAC TTC TAC TAT TAC ACT CTG TCC                864
Arg Ala Val Cys Arg Asn Asn Ile Asn Phe Tyr Tyr Tyr Thr Leu Ser
            275                 280                 285

TGC GCC TTC GCT TAC TGT ATG GGA GGA GAA GAA AGA GCT AAA CAC GTC                912
Cys Ala Phe Ala Tyr Cys Met Gly Gly Glu Glu Arg Ala Lys His Val
        290                 295                 300

CTT TTC GAC TAT GTT GAG ACA TGC GCT GCA CCG GAA ACG AGA GGA ACG                960
Leu Phe Asp Tyr Val Glu Thr Cys Ala Ala Pro Glu Thr Arg Gly Thr
305                 310                 315                 320

TGT GTT TTA TCA GGA CAT ACT TTC TAT GAC ACA TTC GAC AAA GCC AGA               1008
Cys Val Leu Ser Gly His Thr Phe Tyr Asp Thr Phe Asp Lys Ala Arg
            325                 330                 335

TAT CAA TTC CAG GGC CCA TGC AAA GAG CTT CTG ATG GCC GCA GAC TGT               1056
Tyr Gln Phe Gln Gly Pro Cys Lys Glu Leu Leu Met Ala Ala Asp Cys
        340                 345                 350

TAC TGG AAC ACA TGG GAT GTA AAG GTT TCA CAT AGA GAT GTT GAG TCA               1104
Tyr Trp Asn Thr Trp Asp Val Lys Val Ser His Arg Asp Val Glu Ser
                355                 360                 365

TAC ACT GAG GTA GAG AAA GTA ACA ATC AGG AAA CAG TCA ACT GTA GTA               1152
Tyr Thr Glu Val Glu Lys Val Thr Ile Arg Lys Gln Ser Thr Val Val
        370                 375                 380

GAT TTG ATT GTG GAT GGC AAG CAG GTC AAG GTT GGA GGA GTG GAT GTA               1200
Asp Leu Ile Val Asp Gly Lys Gln Val Lys Val Gly Gly Val Asp Val
385                 390                 395                 400

TCT ATC CCG TAC AGT TCT GAG AAC ACA TCC ATA TAC TGG CAG GAT GGA               1248
Ser Ile Pro Tyr Ser Ser Glu Asn Thr Ser Ile Tyr Trp Gln Asp Gly
            405                 410                 415

GAC ATC CTG ACG ACG GCC ATC CTA CCT GAA GCT CTT GTC GTT AAG TTC               1296
Asp Ile Leu Thr Thr Ala Ile Leu Pro Glu Ala Leu Val Val Lys Phe
        420                 425                 430

AAC TTT AAG CAG CTC CTT GTA GTT CAT ATC AGA GAT CCA TTC GAT GGA               1344
Asn Phe Lys Gln Leu Leu Val Val His Ile Arg Asp Pro Phe Asp Gly
                435                 440                 445

AAG ACA TGC GGC ATA TGT GGT AAC TAT AAT CAA GAT TCA ACT GAT GAT               1392
Lys Thr Cys Gly Ile Cys Gly Asn Tyr Asn Gln Asp Ser Thr Asp Asp
        450                 455                 460

TTC TTT GAC GCA GAA GGA GCA TGC GCT CTG ACC CCC AAT CCC CCA GGA               1440
Phe Phe Asp Ala Glu Gly Ala Cys Ala Leu Thr Pro Asn Pro Pro Gly
465                 470                 475                 480

TGT ACA GAG GAG CAG AAA CCA GAA GCT GAG CGA CTC TGC AAT AGT CTA               1488
Cys Thr Glu Glu Gln Lys Pro Glu Ala Glu Arg Leu Cys Asn Ser Leu
            485                 490                 495

TTT GAT AGT TCT ATC GAC GAG AAA TGT AAT GTC TGC TAC AAG CCT GAC               1536
Phe Asp Ser Ser Ile Asp Glu Lys Cys Asn Val Cys Tyr Lys Pro Asp
        500                 505                 510

CGT ATT GCA CGA TGT ATG TAC GAG TAT TGC CTG AGG GGA CAG CAA GGA               1584
Arg Ile Ala Arg Cys Met Tyr Glu Tyr Cys Leu Arg Gly Gln Gln Gly
                515                 520                 525

TTC TGT GAC CAT GCT TGG GAG TTC AAA AAA GAA TGC TAC ATA AAG CAT               1632
Phe Cys Asp His Ala Trp Glu Phe Lys Lys Glu Cys Tyr Ile Lys His
        530                 535                 540

GGA GAC ACT CTA GAA GTA CCA CCT GAA TGC CAA TAA ATGAACAAAG                    1678
Gly Asp Thr Leu Glu Val Pro Pro Glu Cys Gln
545                 550                 555

ATACAGAAGC TAAGACTACT ACAGCAGAAG ATAAAAGAGA AGCTGTAGTT CTTCAAAAAC             1738

AGTATATTTT GATGTACTCA TTGTTTACTT ACATAAAAAT AAATTGTTAT TATCATAACG             1798
```

TAAAGAAAAA AAAAAAAAAA AAAA                                              1822

(2) INFORMATION FOR SEQ ID NO: 3:

(i) SEQUENCE CHARACTERISTICS:
        (A) LENGTH: 1644 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1644
        (D) OTHER INFORMATION: Luciola Cruciata Luciferase (Firefly)

(x) PUBLICATION INFORMATION:
        (H) DOCUMENT NUMBER: 4,968,613

(xi) SEQUENCE DESCRIPTION: SEQ ID NO: 3:

```
ATG GAA AAC ATG GAA AAC GAT GAA AAT ATT GTA GTT GGA CCT AAA CCG        48
Met Glu Asn Met Glu Asn Asp Glu Asn Ile Val Val Gly Pro Lys Pro
 1               5                  10                  15

TTT TAC CCT ATC GAA GAG GGA TCT GCT GGA ACA CAA TTA CGC AAA TAC        96
Phe Tyr Pro Ile Glu Glu Gly Ser Ala Gly Thr Gln Leu Arg Lys Tyr
                20                  25                  30

ATG GAG CGA TAT GCA AAA CTT GGC GCA ATT GCT TTT ACA AAT GCA GTT       144
Met Glu Arg Tyr Ala Lys Leu Gly Ala Ile Ala Phe Thr Asn Ala Val
            35                  40                  45

ACT GGT GTT GAT TAT TCT TAC GCC GAA TAC TTG GAG AAA TCA TGT TGT       192
Thr Gly Val Asp Tyr Ser Tyr Ala Glu Tyr Leu Glu Lys Ser Cys Cys
        50                  55                  60

CTA GGA AAA GCT TTG CAA AAT TAT GGT TTG GTT GTT GAT GGC AGA ATT       240
Leu Gly Lys Ala Leu Gln Asn Tyr Gly Leu Val Val Asp Gly Arg Ile
65                  70                  75                  80

GCG TTA TGC AGT GAA AAC TGT GAA GAA TTT TTT ATT CCT GTA ATA GCC       288
Ala Leu Cys Ser Glu Asn Cys Glu Glu Phe Phe Ile Pro Val Ile Ala
                85                  90                  95

GGA CTG TTT ATA GGT GTA GGT GTT GCA CCC ACT AAT GAG ATT TAC ACT       336
Gly Leu Phe Ile Gly Val Gly Val Ala Pro Thr Asn Glu Ile Tyr Thr
                100                 105                 110

TTA CGT GAA CTG GTT CAC AGT TTA GGT ATC TCT AAA CCA ACA ATT GTA       384
Leu Arg Glu Leu Val His Ser Leu Gly Ile Ser Lys Pro Thr Ile Val
            115                 120                 125

TTT AGT TCT AAA AAA GGC TTA GAT AAA GTT ATA ACA GTA CAG AAA ACA       432
Phe Ser Ser Lys Lys Gly Leu Asp Lys Val Ile Thr Val Gln Lys Thr
        130                 135                 140

GTA ACT ACT ATT AAA ACC ATT GTT ATA CTA GAT AGC AAA GTT GAT TAT       480
Val Thr Thr Ile Lys Thr Ile Val Ile Leu Asp Ser Lys Val Asp Tyr
145                 150                 155                 160

CGA GGA TAT CAA TGT CTG GAC ACC TTT ATA AAA AGA AAC ACT CCA CCA       528
Arg Gly Tyr Gln Cys Leu Asp Thr Phe Ile Lys Arg Asn Thr Pro Pro
                165                 170                 175

GGT TTT CAA GCA TCC AGT TTC AAA ACT GTG GAA GTT GAC CGT AAA GAA       576
Gly Phe Gln Ala Ser Ser Phe Lys Thr Val Glu Val Asp Arg Lys Glu
                180                 185                 190

CAA GTT GCT CTT ATA ATG AAC TCT TCG GGT TCT ACC GGT TTG CCA AAA       624
Gln Val Ala Leu Ile Met Asn Ser Ser Gly Ser Thr Gly Leu Pro Lys
            195                 200                 205

GGC GTA CAA CTT ACT CAC GAA AAT ACA GTC ACT AGA TTT TCT CAT GCT       672
Gly Val Gln Leu Thr His Glu Asn Thr Val Thr Arg Phe Ser His Ala
        210                 215                 220
```

```
AGA GAT CCG ATT TAT GGT AAC CAA GTT TCA CCA GGC ACC GCT GTT TTA      720
Arg Asp Pro Ile Tyr Gly Asn Gln Val Ser Pro Gly Thr Ala Val Leu
225                 230                 235                 240

ACT GTC GTT CCA TTC CAT CAT GGT TTT GGT ATG TTC ACT ACT CTA GGG      768
Thr Val Val Pro Phe His His Gly Phe Gly Met Phe Thr Thr Leu Gly
                245                 250                 255

TAT TTA ATT TGT GGT TTT CGT GTT GTA ATG TTA ACA AAA TTC GAT GAA      816
Tyr Leu Ile Cys Gly Phe Arg Val Val Met Leu Thr Lys Phe Asp Glu
            260                 265                 270

GAA ACA TTT TTA AAA ACT CTA CAA GAT TAT AAA TGT ACA AGT GTT ATT      864
Glu Thr Phe Leu Lys Thr Leu Gln Asp Tyr Lys Cys Thr Ser Val Ile
        275                 280                 285

CTT GTA CCG ACC TTG TTT GCA ATT CTC AAC AAA AGT GAA TTA CTC AAT      912
Leu Val Pro Thr Leu Phe Ala Ile Leu Asn Lys Ser Glu Leu Leu Asn
    290                 295                 300

AAA TAC GAT TTG TCA AAT TTA GTT GAG ATT GCA TCT GGC GGA GCA CCT      960
Lys Tyr Asp Leu Ser Asn Leu Val Glu Ile Ala Ser Gly Gly Ala Pro
305                 310                 315                 320

TTA TCA AAA GAA GTT GGT GAA GCT GTT GCT AGA CGC TTT AAT CTT CCC     1008
Leu Ser Lys Glu Val Gly Glu Ala Val Ala Arg Arg Phe Asn Leu Pro
                325                 330                 335

GGT GTT CGT CAA GGT TAT GGT TTA ACA GAA ACA ACA TCT GCC ATT ATT     1056
Gly Val Arg Gln Gly Tyr Gly Leu Thr Glu Thr Thr Ser Ala Ile Ile
            340                 345                 350

ATT ACA CCA GAA GGA GAC GAT AAA CCA GGA GCT TCT GGA AAA GTC GTG     1104
Ile Thr Pro Glu Gly Asp Asp Lys Pro Gly Ala Ser Gly Lys Val Val
        355                 360                 365

CCG TTG TTT AAA GCA AAA GTT ATT GAT CTT GAT ACC AAA AAA TCT TTA     1152
Pro Leu Phe Lys Ala Lys Val Ile Asp Leu Asp Thr Lys Lys Ser Leu
    370                 375                 380

GGT CCT AAC AGA CGT GGA GAA GTT TGT GTT AAA GGA CCT ATG CTT ATG     1200
Gly Pro Asn Arg Arg Gly Glu Val Cys Val Lys Gly Pro Met Leu Met
385                 390                 395                 400

AAA GGT TAT GTA AAT AAT CCA GAA GCA ACA AAA GAA CTT ATT GAC GAA     1248
Lys Gly Tyr Val Asn Asn Pro Glu Ala Thr Lys Glu Leu Ile Asp Glu
                405                 410                 415

GAA GGT TGG CTG CAC ACC GGA GAT ATT GGA TAT TAT GAT GAA GAA AAA     1296
Glu Gly Trp Leu His Thr Gly Asp Ile Gly Tyr Tyr Asp Glu Glu Lys
            420                 425                 430

CAT TTC TTT ATT GTC GAT CGT TTG AAG TCT TTA ATC AAA TAC AAA GGA     1344
His Phe Phe Ile Val Asp Arg Leu Lys Ser Leu Ile Lys Tyr Lys Gly
        435                 440                 445

TAC CAA GTA CCA CCT GCC GAA TTA GAA TCC GTT CTT TTG CAA CAT CCA     1392
Tyr Gln Val Pro Pro Ala Glu Leu Glu Ser Val Leu Leu Gln His Pro
    450                 455                 460

TCT ATC TTT GAT GCT GGT GTT GCC GGC GTT CCT GAT CCT GTA GCT GGC     1440
Ser Ile Phe Asp Ala Gly Val Ala Gly Val Pro Asp Pro Val Ala Gly
465                 470                 475                 480

GAG CTT CCA GGA GCC GTT GTT GTA CTG GAA AGC GGA AAA AAT ATG ACC     1488
Glu Leu Pro GLy Ala Val Val Val Leu Glu Ser Gly Lys Asn Met Thr
                485                 490                 495

GAA AAA GAA GTA ATG GAT TAT GTT GCA AGT CAA GTT TCA AAT GCA AAA     1536
Glu Lys Glu Val Met Asp Tyr Val Ala Ser Gln Val Ser Asn Ala Lys
            500                 505                 510

CGT TTA CGT GGT GGT GTT CGT TTT GTG GAT GAA GTA CCT AAA GGT CTT     1584
Arg Leu Arg Gly Gly Val Arg Phe Val Asp Glu Val Pro Lys Gly Leu
        515                 520                 525

ACT GGA AAA ATT GAC GGC AGA GCA ATT AGA GAA ATC CTT AAG AAA CCA     1632
Thr Gly Lys Ile Asp Gly Arg Ala Ile Arg Glu Ile Leu Lys Lys Pro
    530                 535                 540
```

```
GTT GCT AAG ATG                                                              1644
Val Ala Lys Met
545

(2) INFORMATION FOR SEQ ID NO: 4:

(i) SEQUENCE CHARACTERISTICS:
        (A) LENGTH: 1820 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1664
        (D) OTHER INFORMATION: Vargula (cypridina) luciferase (x) PUBLICATION INFORMATION:
        (A) AUTHORS:  Thompson et al.
        (C) JOURNAL:  Proc. Natl. Acad. Sci. U.S.A.
        (D) VOLUME:  86
        (F) PAGES:  1326-1332
        (G) DATE:  (1989)
        (H) DOCUMENT NUMBER: JP 3-30678 Osaka (Tsuji)

(xi) SEQUENCE DESCRIPTION: SEQ ID NO: 4:

ATG AAG ATA ATA ATT CTG TCT GTT ATA TTG GCC TAC TGT GTC ACC GAC        48
Met Lys Ile Ile Ile Leu Ser Val Ile Leu Ala Tyr Cys Val Thr Asp
 1               5                  10                  15

AAC TGT CAA GAT GCA TGT CCT GTA GAA GCG GAA CCG CCA TCA AGT ACA        96
Asn Cys Gln Asp Ala Cys Pro Val Glu Ala Glu Pro Pro Ser Ser Thr
                20                  25                  30

CCA ACA GTT CCA ACT TCT TGT GAA GCT AAA GAA GGA GAA TGT ATA GAT       144
Pro Thr Val Pro Thr Ser Cys Glu Ala Lys Glu Gly Glu Cys Ile Asp
            35                  40                  45

ACC AGA TGC GCA ACA TGT AAA CGA GAT ATA CTA TCA GAT GGA CTG TGT       192
Thr Arg Cys Ala Thr Cys Lys Arg Asp Ile Leu Ser Asp Gly Leu Cys
        50                  55                  60

GAA AAT AAA CCA GGG AAG ACA TGC TGT AGA ATG TGC CAG TAT GTG ATT       240
Glu Asn Lys Pro Gly Lys Thr Cys Cys Arg Met Cys Gln Tyr Val Ile
65                  70                  75                  80

GAA TGC AGA GTA GAA GCA GCT GGT TAT TTT AGA ACG TTT TAC GGC AAA       288
Glu Cys Arg Val Glu Ala Ala Gly Tyr Phe Arg Thr Phe Tyr Gly Lys
                85                  90                  95

AGA TTT AAT TTT CAG GAA CCT GGT AAA TAT GTG CTG GCT AGG GGA ACC       336
Arg Phe Asn Phe Gln Glu Pro Gly Lys Tyr Val Leu Ala Arg Gly Thr
               100                 105                 110

AAG GGT GGC GAT TGG TCT GTA ACC CTC ACC ATG GAG AAT CTA GAT GGA       384
Lys Gly Gly Asp Trp Ser Val Thr Leu Thr Met Glu Asn Leu Asp Gly
           115                 120                 125

CAG AAG GGA GCT GTG CTG ACT AAG ACA ACA CTG GAG GTT GCA GGA GAC       432
Gln Lys Gly Ala Val Leu Thr Lys Thr Thr Leu Glu Val Ala Gly Asp
       130                 135                 140

GTA ATA GAC ATT ACT CAA GCT ACT GCA GAT CCT ATC ACA GTT AAC GGA       480
Val Ile Asp Ile Thr Gln Ala Thr Ala Asp Pro Ile Thr Val Asn Gly
145                 150                 155                 160

GGA GCT GAC CCA GTT ATC GCT AAC CCG TTC ACA ATT GGT GAG GTG ACC       528
Gly Ala Asp Pro Val Ile Ala Asn Pro Phe Thr Ile Gly Glu Val Thr
                165                 170                 175

ATT GCT GTT GTT GAA ATA CCG GGC TTC AAT ATC ACA GTC ATC GAA TTC       576
Ile Ala Val Val Glu Ile Pro Gly Phe Asn Ile Thr Val Ile Glu Phe
               180                 185                 190
```

```
TTT AAA CTA ATC GTG ATT GAT ATT CTG GGA GGA AGA TCT GTC AGA ATT      624
Phe Lys Leu Ile Val Ile Asp Ile Leu Gly Gly Arg Ser Val Arg Ile
        195                 200                 205

GCT CCA GAC ACA GCA AAC AAA GGA CTG ATA TCT GGT ATC TGT GGT AAT      672
Ala Pro Asp Thr Ala Asn Lys Gly Leu Ile Ser Gly Ile Cys Gly Asn
210                 215                 220

CTG GAG ATG AAT GAC GCT GAT GAC TTT ACT ACA GAT GCA GAT CAG CTG      720
Leu Glu Met Asn Asp Ala Asp Asp Phe Thr Thr Asp Ala Asp Gln Leu
225                 230                 235                 240

GCG ATC CAA CCC AAC ATA AAC AAA GAG TTC GAC GGC TGC CCA TTC TAT      768
Ala Ile Gln Pro Asn Ile Asn Lys Glu Phe Asp Gly Cys Pro Phe Tyr
        245                 250                 255

GGC AAT CCT TCT GAT ATC GAA TAC TGC AAA GGT CTG ATG GAG CCA TAC      816
Gly Asn Pro Ser Asp Ile Glu Tyr Cys Lys Gly Leu Met Glu Pro Tyr
260                 265                 270

AGA GCT GTA TGT CGT AAC AAT ATC AAC TTC TAC TAT TAC ACT CTA TCC      864
Arg Ala Val Cys Arg Asn Asn Ile Asn Phe Tyr Tyr Tyr Thr Leu Ser
        275                 280                 285

TGT GCC TTC GCT TAC TGT ATG GGA GGA GAA GAA AGA GCT AAA CAC GTC      912
Cys Ala Phe Ala Tyr Cys Met Gly Gly Glu Glu Arg Ala Lys His Val
290                 295                 300

CTT TTC GAC TAT GTT GAG ACA TGC GCT GCG CCG GAA ACG AGA GGA ACG      960
Leu Phe Asp Tyr Val Glu Thr Cys Ala Ala Pro Glu Thr Arg Gly Thr
305                 310                 315                 320

TGT GTT TTA TCA GGA CAT ACT TTC TAT GAC ACA TTC GAC AAA GCA AGA     1008
Cys Val Leu Ser Gly His Thr Phe Tyr Asp Thr Phe Asp Lys Ala Arg
        325                 330                 335

TAT CAA TTC CAG GGC CCA TGC AAG GAG ATT CTG ATG GCC GCA GAC TGT     1056
Tyr Gln Phe Gln Gly Pro Cys Lys Glu Ile Leu Met Ala Ala Asp Cys
340                 345                 350

TAC TGG AAC ACA TGG GAT GTA AAG GTT TCA CAT AGA GAC GTC GAA TCA     1104
Tyr Trp Asn Thr Trp Asp Val Lys Val Ser His Arg Asp Val Glu Ser
        355                 360                 365

TAC ACT GAG GTA GAG AAA GTA ACA ATC AGG AAA CAG TCA ACT GTA GTA     1152
Tyr Thr Glu Val Glu Lys Val Thr Ile Arg Lys Gln Ser Thr Val Val
370                 375                 380

GAT CTC ATT GTG GAT GGC AAG CAG GTC AAG GTT GGA GGA GTG GAT GTA     1200
Asp Leu Ile Val Asp Gly Lys Gln Val Lys Val Gly Gly Val Asp Val
385                 390                 395                 400

TCT ATC CCG TAC AGC TCT GAG AAC ACT TCC ATA TAC TGG CAG GAT GGA     1248
Ser Ile Pro Tyr Ser Ser Glu Asn Thr Ser Ile Tyr Trp Gln Asp Gly
        405                 410                 415

GAC ATC CTG ACG ACG GCC ATC CTA CCT GAA GCT CTT GTC GTT AAG TTC     1296
Asp Ile Leu Thr Thr Ala Ile Leu Pro Glu Ala Leu Val Val Lys Phe
420                 425                 430

AAC TTT AAG CAG CTC CTT GTA GTT CAT ATC AGA GAT CCA TTC GAT GCA     1344
Asn Phe Lys Gln Leu Leu Val Val His Ile Arg Asp Pro Phe Asp Ala
        435                 440                 445

AAG ACA TGC GGC ATA TGT GGT AAC TAT AAT CAA GAT TCA ACT GAT GAT     1392
Lys Thr Cys Gly Ile Cys Gly Asn Tyr Asn Gln Asp Ser Thr Asp Asp
450                 455                 460

TTC TTT GAC GCA GAA GGA GCA TGC GCT CTA ACC CCC AAC CCC CCA GGA     1440
Phe Phe Asp Ala Glu Gly Ala Cys Ala Leu Thr Pro Asn Pro Pro Gly
465                 470                 475                 480

TGT ACA GAG GAA CAG AAA CCA GAA GCT GAG CGA CTT TGC AAT AAT CTC     1488
Cys Thr Glu Glu Gln Lys Pro Glu Ala Glu Arg Leu Cys Asn Asn Leu
        485                 490                 495

TTT GAT TCT TCT ATC GAC GAG AAA TGT AAT GTC TGC TAC AAG CCT GAC     1536
Phe Asp Ser Ser Ile Asp Glu Lys Cys Asn Val Cys Tyr Lys Pro Asp
500                 505                 510
```

```
CGG ATT GCC CGA TGT ATG TAC GAG TAT TGC CTG AGG GGA CAA CAA GGA    1584
Arg Ile Ala Arg Cys Met Tyr Glu Tyr Cys Leu Arg Gly Gln Gln Gly
            515                 520                 525

TTT TGT GAC CAT GCT TGG GAG TTC AAG AAA GAA TGC TAC ATA AAA CAT    1632
Phe Cys Asp His Ala Trp Glu Phe Lys Lys Glu Cys Tyr Ile Lys His
        530                 535                 540

GGA GAC ACT CTA GAA GTA CCA CCT GAA TGT CAA TAA ACGTACAAAG         1678
Gly Asp Thr Leu Glu Val Pro Pro Glu Cys Gln
545                 550                 555

ATACAGAAGC TAAGGCTACT ACAGCAGAAG ATAAAAAAGA AACTGTAGTT CCTTCAAAAA  1738

CCGTGTATTT TATGTACTCA TTGTTTAATT AGAGCAAAAT AAATTGTTAT TATCATAACT  1798

TAAACTAAAA AAAAAAAAA AA                                            1820

(2) INFORMATION FOR SEQ ID NO: 5:

(i) SEQUENCE CHARACTERISTICS:
        (A) LENGTH: 958 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(ix) FEATURE:
        (A) NAME/KEY: Coding Sequence
        (B) LOCATION: 115...702
        (D) OTHER INFORMATION: apoaequorin-encoding gene (x) PUBLICATION INFORMATION:
        (A) AUTHORS: Inouye et al.
        (C) JOURNAL: Proc. Natl. Acad. Sci. U.S.A.
        (D) VOLUME: 82
        (F) PAGES: 3154-3158
        (G) DATE: (1985)
        (H) DOCUMENT NUMBER: 5,093,240

(xi) SEQUENCE DESCRIPTION: SEQ ID NO: 5:

GGGGGGGGGG GGGGGGGGGG GGGGGGGGGG GGGAATGCAA TTCATCTTTG CATCAAAGAA      60

TTACATCAAA TCTCTAGTTG ATCAACTAAA TTGTCTCGAC AACAACAAGC AAAC ATG        117
                                                             Met
                                                             1

ACA AGC AAA CAA TAC TCA GTC AAG CTT ACA TCA GAC TTC GAC AAC CCA    165
Thr Ser Lys Gln Tyr Ser Val Lys Leu Thr Ser Asp Phe Asp Asn Pro
            5                   10                  15

AGA TGG ATT GGA CGA CAC AAG CAT ATG TTC AAT TTC CTT GAT GTC AAC    213
Arg Trp Ile Gly Arg His Lys His Met Phe Asn Phe Leu Asp Val Asn
        20                  25                  30

CAC AAT GGA AAA ATC TCT CTT GAC GAG ATG GTC TAC AAG GCA TCT GAT    261
His Asn Gly Lys Ile Ser Leu Asp Glu Met Val Tyr Lys Ala Ser Asp
    35                  40                  45

ATT GTC ATC AAT AAC CTT GGA GCA ACA CCT GAG CAA GCC AAA CGA CAC    309
Ile Val Ile Asn Asn Leu Gly Ala Thr Pro Glu Gln Ala Lys Arg His
50                  55                  60                  65

AAA GAT GCT GTA GAA GCC TTC TTC GGA GGA GCT GGA ATG AAA TAT GGT    357
Lys Asp Ala Val Glu Ala Phe Phe Gly Gly Ala Gly Met Lys Tyr Gly
            70                  75                  80
```

```
GTG GAA ACT GAT TGG CCT GCA TAT ATT GAA GGA TGG AAA AAA TTG GCT        405
Val Glu Thr Asp Trp Pro Ala Tyr Ile Glu Gly Trp Lys Lys Leu Ala
            85                  90                  95

ACT GAT GAA TTG GAG AAA TAC GCC AAA AAC GAA CCA ACG CTC ATC CGT        453
Thr Asp Glu Leu Glu Lys Tyr Ala Lys Asn Glu Pro Thr Leu Ile Arg
            100                 105                 110

ATA TGG GGT GAT GCT TTG TTT GAT ATC GTT GAC AAA GAT CAA AAT GGA        501
Ile Trp Gly Asp Ala Leu Phe Asp Ile Val Asp Lys Asp Gln Asn Gly
    115                 120                 125

GCC ATT ACA CTG GAT GAA TGG AAA GCA TAC ACC AAA GCT GCT GGT ATC        549
Ala Ile Thr Leu Asp Glu Trp Lys Ala Tyr Thr Lys Ala Ala Gly Ile
130                 135                 140                 145

ATC CAA TCA TCA GAA GAT TGC GAG GAA ACA TTC AGA GTG TGC GAT ATT        597
Ile Gln Ser Ser Glu Asp Cys Glu Glu Thr Phe Arg Val Cys Asp Ile
                150                 155                 160

GAT GAA AGT GGA CAA CTC GAT GTT GAT GAG ATG ACA AGA CAA CAT TTA        645
Asp Glu Ser Gly Gln Leu Asp Val Asp Glu Met Thr Arg Gln His Leu
            165                 170                 175

GGA TTT TGG TAC ACC ATG GAT CCT GCT TGC GAA AAG CTC TAC GGT GGA        693
Gly Phe Trp Tyr Thr Met Asp Pro Ala Cys Glu Lys Leu Tyr Gly Gly
        180                 185                 190

GCT GTC CCC TAAGAAGCTC TACGGTGGTG  ATGCACCCTA GGAAGATGAT GTGATTTTGA   752
Ala Val Pro
    195

ATAAAACACT GATGAATTCA ATCAAAATTT TCCAAATTTT TGAACGATTT CAATCGTTTG      812

TGTTGATTTT TGTAATTAGG AACAGATTAA ATCGAATGAT TAGTTGTTTT TTTAATCAAC      872

AGAACTTACA AATCGAAAAA GTAAAAAAAA AAAAAAAAAA AAAAAAAAAA AAAAAAAAAA      932

AAAAAAAAAA AAAAAAAAA AAAAA                                            958

(2) INFORMATION FOR SEQ ID NO: 6:

(i) SEQUENCE CHARACTERISTICS:
        (A) LENGTH: 591 base pairs
        (B) TYPE: nucleic acid
        (C) STRANDEDNESS: Biochemistry
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(ix) FEATURE:
        (A) NAME/KEY: Coding Sequence
        (B) LOCATION: 1...588
        (D) OTHER INFORMATION: Recombinant Aequorin AEQ1

(x) PUBLICATION INFORMATION:
        (A) AUTHORS: Prasher et al.
        (B) TITLE: Sequence Comparisons of Complementary
            DNAs Encoding Aequorin Isotypes (xi) SEQUENCE DESCRIPTION: SEQ ID NO: 6:

ATG ACC AGC GAA CAA TAC TCA GTC AAG CTT ACA CCA GAC TTC GAC AAC         48
Met Thr Ser Glu Gln Tyr Ser Val Lys Leu Thr Pro Asp Phe Asp Asn
1                   5                   10                  15

CCA AAA TGG ATT GGA CGA CAC AAG CAC ATG TTT AAT TTT CTT GAT GTC         96
Pro Lys Trp Ile Gly Arg His Lys His Met Phe Asn Phe Leu Asp Val
            20                  25                  30
```

```
AAC CAC AAT GGA AGG ATC TCT CTT GAC GAG ATG GTC TAC AAG GCG TCC         144
Asn His Asn Gly Arg Ile Ser Leu Asp Glu Met Val Tyr Lys Ala Ser
        35                  40                  45

GAT ATT GTT ATA AAC AAT CTT GGA GCA ACA CCT GAA CAA GCC AAA CGT         192
Asp Ile Val Ile Asn Asn Leu Gly Ala Thr Pro Glu Gln Ala Lys Arg
    50                  55                  60

CAC AAA GAT GCT GTA GAA GCC TTC TTC GGA GGA GCT GGA ATG AAA TAT         240
His Lys Asp Ala Val Glu Ala Phe Phe Gly Gly Ala Gly Met Lys Tyr
65                  70                  75                  80

GGT GTA GAA ACT GAA TGG CCT GAA TAC ATC GAA GGA TGG AAA AGA CTG         288
Gly Val Glu Thr Glu Trp Pro Glu Tyr Ile Glu Gly Trp Lys Arg Leu
                85                  90                  95

GCT TCC GAG GAA TTG AAA AGG TAT TCA AAA AAC CAA ATC ACA CTT ATT         336
Ala Ser Glu Glu Leu Lys Arg Tyr Ser Lys Asn Gln Ile Thr Leu Ile
            100                 105                 110

CGT TTA TGG GGT GAT GCA TTG TTC GAT ATC ATT GAC AAA GAC CAA AAT         384
Arg Leu Trp Gly Asp Ala Leu Phe Asp Ile Ile Asp Lys Asp Gln Asn
        115                 120                 125

GGA GCT ATT TCA CTG GAT GAA TGG AAA GCA TAC ACC AAA TCT GAT GGC         432
Gly Ala Ile Ser Leu Asp Glu Trp Lys Ala Tyr Thr Lys Ser Asp Gly
    130                 135                 140

ATC ATC CAA TCG TCA GAA GAT TGC GAG GAA ACA TTC AGA GTG TGC GAT         480
Ile Ile Gln Ser Ser Glu Asp Cys Glu Glu Thr Phe Arg Val Cys Asp
145                 150                 155                 160

ATT GAT GAA AGT GGA CAG CTC GAT GTT GAT GAG ATG ACA AGA CAA CAT         528
Ile Asp Glu Ser Gly Gln Leu Asp Val Asp Glu Met Thr Arg Gln His
                165                 170                 175

TTA GGA TTT TGG TAC ACC ATG GAT CCT GCT TGC GAA AAG CTC TAC GGT         576
Leu Gly Phe Trp Tyr Thr Met Asp Pro Ala Cys Glu Lys Leu Tyr Gly
            180                 185                 190

GGA GCT GTC CCC TAA                                                     591
Gly Ala Val Pro *
        195

(2) INFORMATION FOR SEQ ID NO: Recombinant Aequorin AEQ2

(i) SEQUENCE CHARACTERISTICS:
        (A) LENGTH: 591 base pairs
        (B) TYPE: nucleic acid
        (C) STRANDEDNESS: Biochemistry
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(ix) FEATURE:
        (A) NAME/KEY: Coding Sequence
        (B) LOCATION: 1...588

(x) PUBLICATION INFORMATION:
        (A) AUTHORS: Prasher et al.
        (B) TITLE: Sequence Comparisons of Complementary
            DNAs Encoding Aequorin Isotypes (xi) SEQUENCE DESCRIPTION: SEQ ID NO: 7:

ATG ACC AGC GAA CAA TAC TCA GTC AAG CTT ACA TCA GAC TTC GAC AAC          48
Met Thr Ser Glu Gln Tyr Ser Val Lys Leu Thr Ser Asp Phe Asp Asn
1               5                   10                  15

CCA AGA TGG ATT GGA CGA CAC AAG CAT ATG TTC AAT TTC CTT GAT GTC          96
```

```
Pro Arg Trp Ile Gly Arg His Lys His Met Phe Asn Phe Leu Asp Val
         20                  25                  30

AAC CAC AAT GGA AAA ATC TCT CTT GAC GAG ATG GTC TAC AAG GCA TCT    144
Asn His Asn Gly Lys Ile Ser Leu Asp Glu Met Val Tyr Lys Ala Ser
             35                  40                  45

GAT ATT GTC ATC AAT AAC CTT GGA GCA ACA CCT GAG CAA GCC AAA CGA    192
Asp Ile Val Ile Asn Asn Leu Gly Ala Thr Pro Glu Gln Ala Lys Arg
     50                  55                  60

CAC AAA GAT GCT GTA GAA GCC TTC TTC GGA GGA GCT GGA ATG AAA TAT    240
His Lys Asp Ala Val Glu Ala Phe Phe Gly Gly Ala Gly Met Lys Tyr
 65                  70                  75                  80

GGT GTG GAA ACT GAT TGG CCT GCA TAT ATT GAA GGA TGG AAA AAA TTG    288
Gly Val Glu Thr Asp Trp Pro Ala Tyr Ile Glu Gly Trp Lys Lys Leu
                 85                  90                  95

GCT ACT GAT GAA TTG GAG AAA TAC GCC AAA AAC GAA CCA ACG CTC ATC    336
Ala Thr Asp Glu Leu Glu Lys Tyr Ala Lys Asn Glu Pro Thr Leu Ile
            100                 105                 110

CGT ATA TGG GGT GAT GCT TTG TTC GAT ATC GTT GAC AAA GAT CAA AAT    384
Arg Ile Trp Gly Asp Ala Leu Phe Asp Ile Val Asp Lys Asp Gln Asn
        115                 120                 125

GGA GCC ATT ACA CTG GAT GAA TGG AAA GCA TAC ACC AAA GCT GCT GGT    432
Gly Ala Ile Thr Leu Asp Glu Trp Lys Ala Tyr Thr Lys Ala Ala Gly
    130                 135                 140

ATC ATC CAA TCA TCA GAA GAT TGC GAG GAA ACA TTC AGA GTG TGC GAT    480
Ile Ile Gln Ser Ser Glu Asp Cys Glu Glu Thr Phe Arg Val Cys Asp
145                 150                 155                 160

ATT GAT GAA AGT GGA CAA CTC GAT GTT GAT GAG ATG ACA AGA CAA CAT    528
Ile Asp Glu Ser Gly Gln Leu Asp Val Asp Glu Met Thr Arg Gln His
                    165                 170                 175

TTA GGA TTT TGG TAC ACC ATG GAT CCT GCT TGC GAA AAG CTC TAC GGT    576
Leu Gly Phe Trp Tyr Thr Met Asp Pro Ala Cys Glu Lys Leu Tyr Gly
                180                 185                 190

GGA GCT GTC CCC TAA                                                591
Gly Ala Val Pro *
        195
```

(2) INFORMATION FOR SEQ ID NO: 8:

(i) SEQUENCE CHARACTERISTICS:
        (A) LENGTH: 591 base pairs
        (B) TYPE: nucleic acid
        (C) STRANDEDNESS: Biochemistry
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(ix) FEATURE:
        (A) NAME/KEY: Coding Sequence
        (B) LOCATION: 1...588
        (D) OTHER INFORMATION: Recombinant Aequorin AEQ3

(x) PUBLICATION INFORMATION:
        (A) AUTHORS: Prasher et al.
        (B) TITLE: Sequence Comparisons of Complementary
            DNAs Encoding Aequorin Isotypes (xi) SEQUENCE DESCRIPTION: SEQ ID NO: 8:

```
ATG ACC AGC GAA CAA TAC TCA GTC AAG CTT ACA TCA GAC TTC GAC AAC     48
```

```
Met Thr Ser Glu Gln Tyr Ser Val Lys Leu Thr Ser Asp Phe Asp Asn
 1               5                  10                 15

CCA AGA TGG ATT GGA CGA CAC AAG CAT ATG TTC AAT TTC CTT GAT GTC        96
Pro Arg Trp Ile Gly Arg His Lys His Met Phe Asn Phe Leu Asp Val
             20                  25                  30

AAC CAC AAT GGA AAA ATC TCT CTT GAC GAG ATG GTC TAC AAG GCA TCT       144
Asn His Asn Gly Lys Ile Ser Leu Asp Glu Met Val Tyr Lys Ala Ser
             35                  40                  45

GAT ATT GTC ATC AAT AAC CTT GGA GCA ACA CCT GAG CAA GCC AAA CGA       192
Asp Ile Val Ile Asn Asn Leu Gly Ala Thr Pro Glu Gln Ala Lys Arg
 50                  55                  60

CAC AAA GAT GCT GTA GGA GAC TTC TTC GGA GGA GCT GGA ATG AAA TAT       240
His Lys Asp Ala Val Gly Asp Phe Phe Gly Gly Ala Gly Met Lys Tyr
 65                  70                  75                  80

GGT GTG GAA ACT GAT TGG CCT GCA TAC ATT GAA GGA TGG AAA AAA TTG       288
Gly Val Glu Thr Asp Trp Pro Ala Tyr Ile Glu Gly Trp Lys Lys Leu
                 85                  90                  95

GCT ACT GAT GAA TTG GAG AAA TAC GCC AAA AAC GAA CCA ACG CTC ATC       336
Ala Thr Asp Glu Leu Glu Lys Tyr Ala Lys Asn Glu Pro Thr Leu Ile
                100                 105                 110

CGT ATA TGG GGT GAT GCT TTG TTC GAT ATC GTT GAC AAA GAT CAA AAT       384
Arg Ile Trp Gly Asp Ala Leu Phe Asp Ile Val Asp Lys Asp Gln Asn
            115                 120                 125

GGA GCC ATT ACA CTG GAT GAA TGG AAA GCA TAC ACC AAA GCT GCT GGT       432
Gly Ala Ile Thr Leu Asp Glu Trp Lys Ala Tyr Thr Lys Ala Ala Gly
130                 135                 140

ATC ATC CAA TCA TCA GAA GAT TGC GAG GAA ACA TTC AGA GTG TGC GAT       480
Ile Ile Gln Ser Ser Glu Asp Cys Glu Glu Thr Phe Arg Val Cys Asp
145                 150                 155                 160

ATT GAT GAA AAT GGA CAA CTC GAT GTT GAT GAG ATG ACA AGA CAA CAT       528
Ile Asp Glu Asn Gly Gln Leu Asp Val Asp Glu Met Thr Arg Gln His
                165                 170                 175

TTA GGA TTT TGG TAC ACC ATG GAT CCT GCT TGC GAA AAG CTC TAC GGT       576
Leu Gly Phe Trp Tyr Thr Met Asp Pro Ala Cys Glu Lys Leu Tyr Gly
            180                 185                 190

GGA GCT GTC CCC TAA                                                   591
Gly Ala Val Pro  *
            195
```

(2) INFORMATION FOR SEQ ID NO: 9:

(i) SEQUENCE CHARACTERISTICS:
        (A) LENGTH: 567 base pairs
        (B) TYPE: nucleic acid
        (C) STRANDEDNESS: single
        (D) TOPOLOGY: Aequorin photoprotein (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(ix) FEATURE:
        (A) NAME/KEY: Coding Sequence
        (B) LOCATION: 1...567

(x) PUBLICATION INFORMATION:
        (A) AUTHORS: Charbonneau et al.
        (B) TITLE: Amino acid sequence of the calcium-dependent
            photoprotein aequorin
        (C) JOURNAL: Am. Chem. Soc.

(D) VOLUME: 24
(E) ISSUE: 24
(F) PAGES: 6762-6771
(G) DATE: 1985

(xi) SEQUENCE DESCRIPTION: SEQ ID NO: 9:

| | | | | | | | | | | | | | | | | |
|---|---|---|---|---|---|---|---|---|---|---|---|---|---|---|---|---|
| GTC | AAG | CTT | ACA | CCA | GAC | TTC | GAC | AAC | CCA | AAA | TGG | ATT | GGA | CGA | CAC | 48 |
| Val | Lys | Leu | Thr | Pro | Asp | Phe | Asp | Asn | Pro | Lys | Trp | Ile | Gly | Arg | His | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| AAG | CAC | ATG | TTT | AAT | TTT | CTT | GAT | GTC | AAC | CAC | AAT | GGA | AGG | ATC | TCT | 96 |
| Lys | His | Met | Phe | Asn | Phe | Leu | Asp | Val | Asn | His | Asn | Gly | Arg | Ile | Ser | |
| | | | 20 | | | | | 25 | | | | | 30 | | | |

| | | | | | | | | | | | | | | | | |
|---|---|---|---|---|---|---|---|---|---|---|---|---|---|---|---|---|
| CTT | GAC | GAG | ATG | GTC | TAC | AAG | GCG | TCC | GAT | ATT | GTT | ATA | AAC | AAT | CTT | 144 |
| Leu | Asp | Glu | Met | Val | Tyr | Lys | Ala | Ser | Asp | Ile | Val | Ile | Asn | Asn | Leu | |
| | | | 35 | | | | 40 | | | | | 45 | | | | |

| | | | | | | | | | | | | | | | | |
|---|---|---|---|---|---|---|---|---|---|---|---|---|---|---|---|---|
| GGA | GCA | ACA | CCT | GAA | CAA | GCC | AAA | CGT | CAC | AAA | GAT | GCT | GTA | GAA | GCC | 192 |
| Gly | Ala | Thr | Pro | Glu | Gln | Ala | Lys | Arg | His | Lys | Asp | Ala | Val | Glu | Ala | |
| | 50 | | | | | 55 | | | | | 60 | | | | | |

| | | | | | | | | | | | | | | | | |
|---|---|---|---|---|---|---|---|---|---|---|---|---|---|---|---|---|
| TTC | TTC | GGA | GGA | GCT | GCA | ATG | AAA | TAT | GGT | GTA | GAA | ACT | GAA | TGG | CCT | 240 |
| Phe | Phe | Gly | Gly | Ala | Ala | Met | Lys | Tyr | Gly | Val | Glu | Thr | Glu | Trp | Pro | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| GAA | TAC | ATC | GAA | GGA | TGG | AAA | AGA | CTG | GCT | TCC | GAG | GAA | TTG | AAA | AGG | 288 |
| Glu | Tyr | Ile | Glu | Gly | Trp | Lys | Arg | Leu | Ala | Ser | Glu | Glu | Leu | Lys | Arg | |
| | | | | 85 | | | | | 90 | | | | | 95 | | |

| | | | | | | | | | | | | | | | | |
|---|---|---|---|---|---|---|---|---|---|---|---|---|---|---|---|---|
| TAT | TCA | AAA | AAC | CAA | ATC | ACA | CTT | ATT | CGT | TTA | TGG | GGT | GAT | GCA | TTG | 336 |
| Tyr | Ser | Lys | Asn | Gln | Ile | Thr | Leu | Ile | Arg | Leu | Trp | Gly | Asp | Ala | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| TTC | GAT | ATC | ATT | GAC | AAA | GAC | CAA | AAT | GGA | GCT | ATT | TCA | CTG | GAT | GAA | 384 |
| Phe | Asp | Ile | Ile | Asp | Lys | Asp | Gln | Asn | Gly | Ala | Ile | Ser | Leu | Asp | Glu | |
| | | | 115 | | | | | 120 | | | | | 125 | | | |

| | | | | | | | | | | | | | | | | |
|---|---|---|---|---|---|---|---|---|---|---|---|---|---|---|---|---|
| TGG | AAA | GCA | TAC | ACC | AAA | TCT | GCT | GGC | ATC | ATC | CAA | TCG | TCA | GAA | GAT | 432 |
| Trp | Lys | Ala | Tyr | Thr | Lys | Ser | Ala | Gly | Ile | Ile | Gln | Ser | Ser | Glu | Asp | |
| | 130 | | | | | 135 | | | | | 140 | | | | | |

| | | | | | | | | | | | | | | | | |
|---|---|---|---|---|---|---|---|---|---|---|---|---|---|---|---|---|
| TGC | GAG | GAA | ACA | TTC | AGA | GTG | TGC | GAT | ATT | GAT | GAA | AGT | GGA | CAG | CTC | 480 |
| Cys | Glu | Glu | Thr | Phe | Arg | Val | Cys | Asp | Ile | Asp | Glu | Ser | Gly | Gln | Leu | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| GAT | GTT | GAT | GAG | ATG | ACA | AGA | CAA | CAT | TTA | GGA | TTT | TGG | TAC | ACC | ATG | 528 |
| Asp | Val | Asp | Glu | Met | Thr | Arg | Gln | His | Leu | Gly | Phe | Trp | Tyr | Thr | Met | |
| | | | | 165 | | | | | 170 | | | | | 175 | | |

| | | | | | | | | | | | |
|---|---|---|---|---|---|---|---|---|---|---|---|
| GAT | CCT | GCT | TGC | GAA | AAG | CTC | TAC | GGT | GGA | GCT | GTC | CCC | 567 |
| Asp | Pro | Ala | Cys | Glu | Lys | Leu | Tyr | Gly | Gly | Ala | Val | Pro | |
| | | | 180 | | | | | 185 | | | | | |

(2) INFORMATION FOR SEQ ID NO: 10:

(i) SEQUENCE CHARACTERISTICS:
        (A) LENGTH: 588 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(ix) FEATURE:
        (A) NAME/KEY: Coding Sequence
        (B) LOCATION: 1...588
        (D) OTHER INFORMATION: Aequorin mutant w/increased
           bioluminescence activity (x) PUBLICATION INFORMATION:
    (H) DOCUMENT NUMBER: 5,360,728
    (K) RELEVANT RESIDUES IN SEQ ID NO: 10: Asp 124 changed to Ser (xi) SEQUENCE DESCRIPTION: SEQ ID NO: 10:

```
ATG ACC AGC GAA CAA TAC TCA GTC AAG CTT ACA CCA GAC TTC GAC AAC      48
Met Thr Ser Glu Gln Tyr Ser Val Lys Leu Thr Pro Asp Phe Asp Asn
 1               5                  10                  15

CCA AAA TGG ATT GGA CGA CAC AAG CAC ATG TTT AAT TTT CTT GAT GTC      96
Pro Lys Trp Ile Gly Arg His Lys His Met Phe Asn Phe Leu Asp Val
            20                  25                  30

AAC CAC AAT GGA AGG ATC TCT CTT GAC GAG ATG GTC TAC AAG GCG TCC     144
Asn His Asn Gly Arg Ile Ser Leu Asp Glu Met Val Tyr Lys Ala Ser
        35                  40                  45

GAT ATT GTT ATA AAC AAT CTT GGA GCA ACA CCT GAA CAA GCC AAA CGT     192
Asp Ile Val Ile Asn Asn Leu Gly Ala Thr Pro Glu Gln Ala Lys Arg
    50                  55                  60

CAC AAA GAT GCT GTA GAA GCC TTC TTC GGA GGA GCT GCA ATG AAA TAT     240
His Lys Asp Ala Val Glu Ala Phe Phe Gly Gly Ala Ala Met Lys Tyr
 65                 70                  75                  80

GGT GTA GAA ACT GAA TGG CCT GAA TAC ATC GAA GGA TGG AAA AGA CTG     288
Gly Val Glu Thr Glu Trp Pro Glu Tyr Ile Glu Gly Trp Lys Arg Leu
                85                  90                  95

GCT TCC GAG GAA TTG AAA AGG TAT TCA AAA AAC CAA ATC ACA CTT ATT     336
Ala Ser Glu Glu Leu Lys Arg Tyr Ser Lys Asn Gln Ile Thr Leu Ile
            100                 105                 110

CGT TTA TGG GGT GAT GCA TTG TTC GAT ATC ATT TCC AAA GAC CAA AAT     384
Arg Leu Trp Gly Asp Ala Leu Phe Asp Ile Ile Ser Lys Asp Gln Asn
        115                 120                 125

GGA GCT ATT TCA CTG GAT GAA TGG AAA GCA TAC ACC AAA TCT GCT GGC     432
Gly Ala Ile Ser Leu Asp Glu Trp Lys Ala Tyr Thr Lys Ser Ala Gly
    130                 135                 140

ATC ATC CAA TCG TCA GAA GAT TGC GAG GAA ACA TTC AGA GTG TGC GAT     480
Ile Ile Gln Ser Ser Glu Asp Cys Glu Glu Thr Phe Arg Val Cys Asp
145                 150                 155                 160

ATT GAT GAA AGT GGA CAG CTC GAT GTT GAT GAG ATG ACA AGA CAA CAT     528
Ile Asp Glu Ser Gly Gln Leu Asp Val Asp Glu Met Thr Arg Gln His
                165                 170                 175

TTA GGA TTT TGG TAC ACC ATG GAT CCT GCT TGC GAA AAG CTC TAC GGT     576
Leu Gly Phe Trp Tyr Thr Met Asp Pro Ala Cys Glu Lys Leu Tyr Gly
            180                 185                 190

GGA GCT GTC CCC                                                     588
Gly Ala Val Pro
        195
```

(2) INFORMATION FOR SEQ ID NO: 11:

(i) SEQUENCE CHARACTERISTICS:
        (A) LENGTH: 588 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(ix) FEATURE:

(A) NAME/KEY: Coding Sequence
        (B) LOCATION: 1...588
        (D) OTHER INFORMATION: Recombinant site-directed Aequorin
            mutant w/increased biolum. activity (x) PUBLICATION INFORMATION:
        (H) DOCUMENT NUMBER: 5,360,728
        (K) RELEVANT RESIDUES IN SEQ ID NO: 11: Glu 135 changed to Ser (xi) SEQUENCE DESCRIPTION: SEQ ID NO: 11:

```
ATG ACC AGC GAA CAA TAC TCA GTC AAG CTT ACA CCA GAC TTC GAC AAC         48
Met Thr Ser Glu Gln Tyr Ser Val Lys Leu Thr Pro Asp Phe Asp Asn
 1               5                  10                  15

CCA AAA TGG ATT GGA CGA CAC AAG CAC ATG TTT AAT TTT CTT GAT GTC         96
Pro Lys Trp Ile Gly Arg His Lys His Met Phe Asn Phe Leu Asp Val
            20                  25                  30

AAC CAC AAT GGA AGG ATC TCT CTT GAC GAG ATG GTC TAC AAG GCG TCC        144
Asn His Asn Gly Arg Ile Ser Leu Asp Glu Met Val Tyr Lys Ala Ser
        35                  40                  45

GAT ATT GTT ATA AAC AAT CTT GGA GCA ACA CCT GAA CAA GCC AAA CGT        192
Asp Ile Val Ile Asn Asn Leu Gly Ala Thr Pro Glu Gln Ala Lys Arg
 50                  55                  60

CAC AAA GAT GCT GTA GAA GCC TTC TTC GGA GGA GCT GCA ATG AAA TAT        240
His Lys Asp Ala Val Glu Ala Phe Phe Gly Gly Ala Ala Met Lys Tyr
 65                  70                  75                  80

GGT GTA GAA ACT GAA TGG CCT GAA TAC ATC GAA GGA TGG AAA AGA CTG        288
Gly Val Glu Thr Glu Trp Pro Glu Tyr Ile Glu Gly Trp Lys Arg Leu
                85                  90                  95

GCT TCC GAG GAA TTG AAA AGG TAT TCA AAA AAC CAA ATC ACA CTT ATT        336
Ala Ser Glu Glu Leu Lys Arg Tyr Ser Lys Asn Gln Ile Thr Leu Ile
            100                 105                 110

CGT TTA TGG GGT GAT GCA TTG TTC GAT ATC ATT TCC AAA GAC CAA AAT        384
Arg Leu Trp Gly Asp Ala Leu Phe Asp Ile Ile Ser Lys Asp Gln Asn
        115                 120                 125

GGA GCT ATT TCA CTG GAT TCA TGG AAA GCA TAC ACC AAA TCT GCT GGC        432
Gly Ala Ile Ser Leu Asp Ser Trp Lys Ala Tyr Thr Lys Ser Ala Gly
130                 135                 140

ATC ATC CAA TCG TCA GAA GAT TGC GAG GAA ACA TTC AGA GTG TGC GAT        480
Ile Ile Gln Ser Ser Glu Asp Cys Glu Glu Thr Phe Arg Val Cys Asp
145                 150                 155                 160

ATT GAT GAA AGT GGA CAG CTC GAT GTT GAT GAG ATG ACA AGA CAA CAT        528
Ile Asp Glu Ser Gly Gln Leu Asp Val Asp Glu Met Thr Arg Gln His
                165                 170                 175

TTA GGA TTT TGG TAC ACC ATG GAT CCT GCT TGC GAA AAG CTC TAC GGT        576
Leu Gly Phe Trp Tyr Thr Met Asp Pro Ala Cys Glu Lys Leu Tyr Gly
            180                 185                 190

GGA GCT GTC CCC                                                        588
Gly Ala Val Pro
        195
```

(2) INFORMATION FOR SEQ ID NO: 12:

(i) SEQUENCE CHARACTERISTICS:
        (A) LENGTH: 588 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(ix) FEATURE:
        (A) NAME/KEY: Coding Sequence
        (B) LOCATION: 1...588
        (D) OTHER INFORMATION: Recombinant site-directed
            Aequorin mutant w/increased biolum. activity (x) PUBLICATION INFORMATION:
        (H) DOCUMENT NUMBER: 5,360,728

(xi) SEQUENCE DESCRIPTION: SEQ ID NO: 12:

```
ATG ACC AGC GAA CAA TAC TCA GTC AAG CTT ACA CCA GAC TTC GAC AAC      48
Met Thr Ser Glu Gln Tyr Ser Val Lys Leu Thr Pro Asp Phe Asp Asn
 1               5                  10                  15

CCA AAA TGG ATT GGA CGA CAC AAG CAC ATG TTT AAT TTT CTT GAT GTC      96
Pro Lys Trp Ile Gly Arg His Lys His Met Phe Asn Phe Leu Asp Val
             20                  25                  30

AAC CAC AAT GGA AGG ATC TCT CTT GAC GAG ATG GTC TAC AAG GCG TCC     144
Asn His Asn Gly Arg Ile Ser Leu Asp Glu Met Val Tyr Lys Ala Ser
         35                  40                  45

GAT ATT GTT ATA AAC AAT CTT GGA GCA ACA CCT GAA CAA GCC AAA CGT     192
Asp Ile Val Ile Asn Asn Leu Gly Ala Thr Pro Glu Gln Ala Lys Arg
 50                  55                  60

CAC AAA GAT GCT GTA GAA GCC TTC TTC GGA GGA GCT GCA ATG AAA TAT     240
His Lys Asp Ala Val Glu Ala Phe Phe Gly Gly Ala Ala Met Lys Tyr
 65                  70                  75                  80

GGT GTA GAA ACT GAA TGG CCT GAA TAC ATC GAA GGA TGG AAA AGA CTG     288
Gly Val Glu Thr Glu Trp Pro Glu Tyr Ile Glu Gly Trp Lys Arg Leu
             85                  90                  95

GCT TCC GAG GAA TTG AAA AGG TAT TCA AAA AAC CAA ATC ACA CTT ATT     336
Ala Ser Glu Glu Leu Lys Arg Tyr Ser Lys Asn Gln Ile Thr Leu Ile
            100                 105                 110

CGT TTA TGG GGT GAT GCA TTG TTC GAT ATC ATT TCC AAA GAC CAA AAT     384
Arg Leu Trp Gly Asp Ala Leu Phe Asp Ile Ile Ser Lys Asp Gln Asn
        115                 120                 125

GCA GCT ATT TCA CTG GAT GAA TGG AAA GCA TAC ACC AAA TCT GCT GGC     432
Ala Ala Ile Ser Leu Asp Glu Trp Lys Ala Tyr Thr Lys Ser Ala Gly
130                 135                 140

ATC ATC CAA TCG TCA GAA GAT TGC GAG GAA ACA TTC AGA GTG TGC GAT     480
Ile Ile Gln Ser Ser Glu Asp Cys Glu Glu Thr Phe Arg Val Cys Asp
145                 150                 155                 160

ATT GAT GAA AGT GGA CAG CTC GAT GTT GAT GAG ATG ACA AGA CAA CAT     528
Ile Asp Glu Ser Gly Gln Leu Asp Val Asp Glu Met Thr Arg Gln His
                165                 170                 175

TTA GGA TTT TGG TAC ACC ATG GAT CCT GCT TGC GAA AAG CTC TAC GGT     576
Leu Gly Phe Trp Tyr Thr Met Asp Pro Ala Cys Glu Lys Leu Tyr Gly
            180                 185                 190

GGA GCT GTC CCC                                                      588
Gly Ala Val Pro
        195
```

(2) INFORMATION FOR SEQ ID NO: 13:

(i) SEQUENCE CHARACTERISTICS:
        (A) LENGTH: 567 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence (B) LOCATION: 1...567
(D) OTHER INFORMATION: Recombinant apoaequorin (AQUALITE )

(xi) SEQUENCE DESCRIPTION: SEQ ID NO: 13:

```
GTC AAG CTT ACA CCA GAC TTC GAC AAC CCA AAA TGG ATT GGA CGA CAC      48
Val Lys Leu Thr Pro Asp Phe Asp Asn Pro Lys Trp Ile Gly Arg His
1               5                  10                  15

AAG CAC ATG TTT AAT TTT CTT GAT GTC AAC CAC AAT GGA AGG ATC TCT      96
Lys His Met Phe Asn Phe Leu Asp Val Asn His Asn Gly Arg Ile Ser
                20                  25                  30

CTT GAC GAG ATG GTC TAC AAG GCG TCC GAT ATT GTT ATA AAC AAT CTT     144
Leu Asp Glu Met Val Tyr Lys Ala Ser Asp Ile Val Ile Asn Asn Leu
            35                  40                  45

GGA GCA ACA CCT GAA CAA GCC AAA CGT CAC AAA GAT GCT GTA GAA GCC     192
Gly Ala Thr Pro Glu Gln Ala Lys Arg His Lys Asp Ala Val Glu Ala
        50                  55                  60

TTC TTC GGA GGA GCT GGA ATG AAA TAT GGT GTA GAA ACT GAA TGG CCT     240
Phe Phe Gly Gly Ala Gly Met Lys Tyr Gly Val Glu Thr Glu Trp Pro
65                  70                  75                  80

GAA TAC ATC GAA GGA TGG AAA AAA CTG GCT TCC GAG GAA TTG AAA AGG     288
Glu Tyr Ile Glu Gly Trp Lys Lys Leu Ala Ser Glu Glu Leu Lys Arg
                85                  90                  95

TAT TCA AAA AAC CAA ATC ACA CTT ATT CGT TTA TGG GGT GAT GCA TTG     336
Tyr Ser Lys Asn Gln Ile Thr Leu Ile Arg Leu Trp Gly Asp Ala Leu
                100                 105                 110

TTC GAT ATC ATT GAC AAA GAC CAA AAT GGA GCT ATT CTG TCA GAT GAA     384
Phe Asp Ile Ile Asp Lys Asp Gln Asn Gly Ala Ile Leu Ser Asp Glu
            115                 120                 125

TGG AAA GCA TAC ACC AAA TCT GAT GGC ATC ATC CAA TCG TCA GAA GAT     432
Trp Lys Ala Tyr Thr Lys Ser Asp Gly Ile Ile Gln Ser Ser Glu Asp
        130                 135                 140

TGC GAG GAA ACA TTC AGA GTG TGC GAT ATT GAT GAA AGT GGA CAG CTC     480
Cys Glu Glu Thr Phe Arg Val Cys Asp Ile Asp Glu Ser Gly Gln Leu
145                 150                 155                 160

GAT GTT GAT GAG ATG ACA AGA CAA CAT TTA GGA TTT TGG TAC ACC ATG     528
Asp Val Asp Glu Met Thr Arg Gln His Leu Gly Phe Trp Tyr Thr Met
                165                 170                 175

GAT CCT GCT TGC GAA AAG CTC TAC GGT GGA GCT GTC CCC                 567
Asp Pro Ala Cys Glu Lys Leu Tyr Gly Gly Ala Val Pro
                180                 185
```

(2) INFORMATION FOR SEQ ID NO: 14:

(i) SEQUENCE CHARACTERISTICS:
        (A) LENGTH: 236 amino acids
        (B) TYPE: amino acid
        (D) TOPOLOGY: linear (ii) MOLECULE TYPE: protein (ix) FEATURE:
        (D) OTHER INFORMATION: Vibrio fisheri Flavin reductase (x) PUBLICATION INFORMATION:
        (H) DOCUMENT NUMBER: 5,484,723

(xi) SEQUENCE DESCRIPTION: SEQ ID NO: 14:

```
Met Pro Ile Asn Cys Lys Val Lys Ser Ile Glu Pro Leu Ala Cys Asn
1               5                  10                  15

Thr Phe Arg Ile Leu Leu His Pro Glu Gln Pro Val Ala Phe Lys Ala
                20                  25                  30

Gly Gln Tyr Leu Thr Val Val Met Gly Glu Lys Asp Lys Arg Pro Phe
            35                  40                  45
```

-continued

```
Ser Ile Ala Ser Ser Pro Cys Arg His Glu Gly Glu Ile Glu Leu His
    50                  55                  60
Ile Gly Ala Ala Glu His Asn Ala Tyr Ala Gly Glu Val Val Glu Ser
 65                  70                  75                  80
Met Lys Ser Ala Leu Glu Thr Gly Gly Asp Ile Leu Ile Asp Ala Pro
                 85                  90                  95
His Gly Glu Ala Trp Ile Arg Glu Asp Ser Asp Arg Ser Met Leu Leu
                100                 105                 110
Ile Ala Gly Gly Thr Gly Phe Ser Tyr Val Arg Ser Ile Leu Asp His
            115                 120                 125
Cys Ile Ser Gln Gln Ile Gln Lys Pro Ile Tyr Leu Tyr Trp Gly Gly
130                 135                 140
Arg Asp Glu Cys Gln Leu Tyr Ala Lys Ala Glu Leu Glu Ser Ile Ala
145                 150                 155                 160
Gln Ala His Ser His Ile Thr Phe Val Pro Val Val Glu Lys Ser Glu
                165                 170                 175
Gly Trp Thr Gly Lys Thr Gly Asn Val Leu Glu Ala Val Lys Ala Asp
            180                 185                 190
Phe Asn Ser Leu Ala Asp Met Asp Ile Tyr Ile Ala Gly Arg Phe Glu
            195                 200                 205
Met Ala Gly Ala Ala Arg Glu Gln Phe Thr Thr Glu Lys Gln Ala Lys
    210                 215                 220
Lys Glu Gln Leu Phe Gly Asp Ala Phe Ala Phe Ile
225                 230                 235
```

APPARATUS AND METHOD FOR DETECTING AND IDENTIFYING INFECTIOUS AGENTS

RELATED APPLICATIONS

This application is a divisional of application Ser. No. 08/990,103 filed Dec. 12, 1997 now U.S. Pat. No. 6,458,547. This application claims priority under 35 U.S.C. §119(e) to U.S. Provisional application Ser. No. 60/037,675, filed Feb. 11, 1997 and to U.S. Provisional application Ser. No. 60/033,745, filed Dec. 12, 1996.

Certain subject matter in this application is related to subject matter in U.S. application Ser. No. 08/757,046, filed Nov. 25, 1996, to Bruce Bryan entitled "BIOLUMINESCENT NOVELTY ITEMS" (B), and to U.S. application Ser. No. 08/597,274, filed Feb. 6, 1996, to Bruce Bryan, entitled "BIOLUMINESCENT NOVELTY ITEMS". This application is also related to U.S. application Ser. No. 08/908,909, filed Aug. 8, 1997, to Bruce Bryan entitled "DETECTION AND VISUALIZATION OF NEOPLASMS AND OTHER TISSUES" and to U.S. Provisional application Serial No. 60/023,374, filed Aug. 8, 1996, entitled "DETECTION AND VISUALIZATION OF NEOPLASMS AND OTHER TISSUES", and also to published International PCT application No. WO 97/29,319.

The subject matter of each of the above noted U.S. applications, provisional applications and International application is herein incorporated by reference in its entirety.

FIELD OF INVENTION

The present invention relates to methods for the identification of an analyte in a biological medium using bioluminescence. More particularly, a method is provided for diagnosing diseases employing a solid phase methodology and a luciferase-luciferin bioluminescence generating system. Methods employing biomineralization for depositing silicon on a matrix support are also provided herein.

BACKGROUND OF THE INVENTION

Bioluminescence

Luminescence is a phenomenon in which energy is specifically channeled to a molecule to produce an excited state. Return to a lower energy state is accompanied by release of a photon (hγ). Luminescence includes fluorescence, phosphorescence, chemiluminescence and bioluminescence. Bioluminescence is the process by which living organisms emit light that is visible to other organisms. Luminescence may be represented as follows:

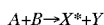

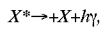

where X* is an electronically excited molecule and hγ represents light emission upon return of X* to a lower energy state. Where the luminescence is bioluminescence, creation of the excited state derives from an enzyme catalyzed reaction. The color of the emitted light in a bioluminescent (or chemiluminescent or other luminescent) reaction is characteristic of the excited molecule, and is independent from its source of excitation and temperature.

An essential condition for bioluminescence is the use of molecular oxygen, either bound or free in the presence of a luciferase. Luciferases, are oxygenases, that act on a substrate, luciferin, in the presence of molecular oxygen and transform the substrate to an excited state. Upon return to a lower energy level, energy is released in the form of light [for reviews see, e.g., McElroy et al. (1966) in *Molecular Architecture in Cell Physiology*, Hayashi et al., eds., Prentice-Hall, Inc., Englewood Cliffs, N.J., pp.63–80; WNard et al., Chapter 7 in *Chemi-and Bioluminescence*, Burr, ed., Marcel Dekker, Inc. NY, pp.321–358; Hastings, J. W. in (1995) *Cell Physiology:Source Book*, N. Sperelakis (ed.), Academic Press, pp 665–681; *Luminescence, Narcosis and Life in the Deep Sea*, Johnson, Vantage Press, NY, see, esp. pp. 50–56].

Though rare overall, bioluminescence is more common in marine organisms than in terrestrial organisms. Bioluminescence has developed from as many as thirty evolutionarily distinct origins and, thus, is manifested in a variety of ways so that the biochemical and physiological mechanisms responsible for bioluminescence in different organisms are distinct. Bioluminescent species span many genera and include microscopic organisms, such as bacteria [primarily marine bacteria including Vibrio species], fungi, algae and dinoflagellates, to marine organisms, including arthropods, mollusks, echinoderms, and chordates, and terrestrial organism including annelid worms and insects.

Bioluminescence, as well as other types of chemiluminescence, is used for quantitative determinations of specific substances in biology and medicine. For example, luciferase genes have been cloned and exploited as reporter genes in numerous assays, for many purposes. Since the different luciferase systems have different specific requirements, they may be used to detect and quantify a variety of substances. The majority of commercial bioluminescence applications are based on firefly [*Photinus pyralis*] luciferase. One of the first and still widely used assays involves the use of firefly luciferase to detect the presence of ATP. It is also used to detect and quantify other substrates or co-factors in the reaction. Any reaction that produces or utilizes NAD(H), NADP(H) or long chain aldehyde, either directly or indirectly, can be coupled to the light-emitting reaction of bacterial luciferase.

Another luciferase system that has been used commercially for analytical purposes is the Aequorin system. The purified jellyfish photoprotein, aequorin, is used to detect and quantify intracellular $Ca^{2+}$ and its changes under various experimental conditions. The Aequorin photoprotein is relatively small [~20 kDa], nontoxic, and can be injected into cells in quantities adequate to detect calcium over a large concentration range [$3 \times 10^{-7}$ to $10^{-4}$ M].

Because of their analytical utility, many luciferases and substrates have been studied and well-characterized and are commercially available [e.g., firefly luciferase is available from Sigma, St. Louis, Mo., and Boehringer Mannheim Biochemicals, Indianapolis, Ind.; recombinantly produced firefly luciferase and other reagents based on this gene or for use with this protein are available from Promega Corporation, Madison, Wis.; the aequorin photoprotein luciferase from jellyfish and luciferase from Renilla are commercially available from Sealite Sciences, Bogart, Ga.; coelenterazine, the naturally-occurring substrate for these luciferases, is available from Molecular Probes, Eugene, Oreg.]. These luciferases and related reagents are used as reagents for diagnostics, quality control, environmental testing and other such analyses.

Chips, Arrays and Microelectronics

Microelectronics, chip arrays and other solid phase spacially addressable arrays have been been developed for use in diagnostics and other applications. At present, methods for detection of positive results are inadequate or inconvenient. There exists a need for improved, particularly more rapid detection methods.

Therefore, it is an object herein to provide detection means and methods.

SUMMARY OF THE INVENTION

A method is provided for diagnosing diseases, particularly infectious diseases, using chip methodology and a luciferase-luciferin bioluminescence generating :system. A chip device for practicing the methods is also provided herein. The chip includes an integrated photodetector that detects the photons emitted by the bioluminescence generating system. The method may be practiced with any suitable chip device, including self-addressable and non-self addressable formats, that is modified as described herein for detection of generated photons by the bioluminescence generating systems. The chip device provided herein is adaptable for use in an array format for the detection and identification of infectious agents in biological specimens.

To prepare the chip, a suitable matrix for chip production is selected, the chip is fabricated by suitably derivatizing the matrix for linkage of macromolecules, and including linkage of photodiodes, photomultipliers CCD (charge coupled device) or other suitable detector, for measuring light production; attaching an appropriate macromolecule, such as a biological molecule or anti-ligand, e.g., a receptor, such as an antibody, to the chip, preferably to an assigned location thereon. Photodiodes are presently among the preferred detectors, and specified herein. It is understood, however, that other suitable detectors may be substituted therefor.

In one embodiment, the chip is made using an integrated circuit with an array, such as an X–Y array, of photodetectors. The surface of circuit is treated to render it inert to conditions of the diagnostic assays for which the chip is intended, and is adapted, such as by derivatization for linking molecules, such as antibodies. A selected antibody or panel of antibodies, such as an antibody specific for particularly bacterial antigen, is affixed to the surface of the chip above each photodetector. After contacting the chip with a test sample, the chip is contacted a second antibody linked to a component of a bioluminescence generating system, such as a luciferase or luciferin, specific for the antigen. The remaining components of the bioluminescence generating reaction are added, and, if any of the antibodies linked to a component of a bioluminescence generating system are present on the chip, light will be generated and detected by the adjacent photodetector. The photodetector is operatively linked to a computer, which is programmed with information identifying the linked antibodies, records the event, and thereby identifies antigens present in the test sample.

The chip is employed in any desired assay, such as an assay for infectious disease or antibiotic sensitivity, by, for example, linking an antibody or a panel of antibodies, to the surface, contacting the chip with a test sample of a body fluid, such as urine, blood and cerebral spinal fluid (CFS), for a sufficient time, depending upon assay format, such as to bind the a target in the sample; washing the chip and then incubating with a secondary antibody conjugated to a luciferase or an antibody:luciferase fusion protein; initiating the bioluminescent reaction; detecting light emitted at each location bound with a target through the photodiode in the chip; transferring the electronic signal from the chip to a computer for analysis.

In one embodiment, the chip is a nonself-addressable, microelectronic device for detecting photons of light emitted by light-emitting chemical reactions. The device includes a substrate, an array of loci, herein designated micro-locations, defined thereon, and an independent photodetector optically coupled to each micro-location. Each micro-location holds a separate chemical reactant that will emit photons of light when a reaction takes place thereat. Each photodetector generates a sensed signal responsive to the photons emitted at the corresponding micro-location when the reaction takes place thereat, and each photodetector is independent from the other photodetectors. The device also includes an electronic circuit that reads the sensed signal generated by each photodetector and generates output data signals therefrom. The output data signals are indicative of the light emitted at each micro-location.

In another embodiment, a microelectronic device for detecting and identifying analytes in a fluid sample using light-emitting reactions is provided. The device includes a substrate, an array of micro-locations defined thereon for receiving the fluid sample to be analyzed, a separate targeting agent attached to an attachment layer of each micro-location, and an independent photodetector optically coupled to each micro-location. Each targeting agent is, preferably, specific for binding a selected analyte that may be present in the received sample. Each photodetector generates a sensed signal responsive to photons of light emitted at the corresponding micro-location when the selected analyte bound thereto is exposed to a secondary binding agent also specific for binding the selected analyte or the targeting agent-selected analyte complex and linked to one or more components of a light-emitting reaction. The chip is then reacted with the remaining components to emit the photons when the selected analyte is present. An electronic circuit reads the sensed signal generated by each photodetector and generates output data signals therefrom that are indicative of the light emitted at each micro-location.

In yet another embodiment, a microelectronic device for detecting and identifying analytes in a biological sample using luciferase-luciferin bio- luminescence is provided. The device includes a substrate, an array of micro-locations defined thereon for receiving the sample to be analyzed, a separate anti-ligand, such as a receptor antibody, attached to an attachment layer of each micro-location, and an independent photodetector optically coupled to each micro-location. Each receptor antibody is specific for binding a selected analyte that may be present in the received sample. Each photodetector generates a sensed signal responsive to bioluminescence emitted at the corresponding micro-location when the selected analyte bound to the corresponding receptor antibody is exposed to a secondary antibody also specific to the selected analyte or to the receptor antibody-selected analyte complex and linked to one or more components of a luciferase-luciferin reaction, and is then reacted with the remaining components to generate the bioluminescence when the selected analyte is present. An electronic circuit reads the sensed signal from each photodetector and generates output data signals therefrom. The output data signals are indicative of the bioluminescence emitted at each micro-location by the reaction.

In another embodiment, a method of detecting and identifying analytes in a biological sample using luciferase-luciferin bioluminescence is provided. The method includes providing a microelectronic device having a surface with an array of micro-locations defined thereon, derivatizing the surface to permit or enhance the attachment of a receptor antibody or plurality of antibodies thereto at each micro-location, and attaching a specific receptor antibody or plurality thereof to the surface at each micro-location. The selected antibody is specific for binding to a selected analyte that may be present in the sample. The method also includes applying the sample to the surface such that the selected analytes will bind to the receptor antibody attached to the surface at each micro-location, washing the sample from the surface after waiting a sufficient period of time for the selected analytes to bind with the receptor antibody at each micro-location, exposing the surface to a secondary antibody specific to bind the selected analyte already bound to the receptor antibody at each micro-location when the selected analyte is present, the secondary antibody linked to one of a luciferase and a luciferin, and initiating the reaction by applying the other of the luciferase and luciferin to the surface. The method also includes detecting photons of light emitted by the reaction using a photodetector optically coupled to each micro-location, each photodetector generating a sensed signal representative of the bio-luminescent activity thereat, reading the sensed signal from each photodetector and generating output data signals therefrom indicative of the bioluminescence emitted at each micro-location by the reaction.

In a further embodiment, a system for detecting and identifying analytes in a biological sample using luciferase-luciferin bioluminescence is provided. The system includes: a microelectronic device including an array of micro-locations for receiving the sample; a separate receptor antibody attached to an attachment layer of each micro-location, each receptor antibody is specific for a selected analyte that may be present in the received sample; a photodetector that generates a sensed signal responsive to bioluminescence emitted at the corresponding micro-location when the selected analyte bound to the corresponding receptor antibody is exposed to a secondary antibody also specific to the selected analyte and linked to one of a luciferase and a luciferin, and is then reacted with the other of the luciferase and luciferin to generate the bioluminescence when the selected analyte is present, and an electronic circuit which reads the sensed signal from each photodetector and generates output data signals therefrom indicative of the bioluminescence emitted at each micro-location by the reaction. The system includes a processing instrument including an input interface circuit for receiving the output data signals indicative of the bio-luminescence emitted at each micro-location, a memory circuit for storing a data acquisition array having a location associated with each micro-location, an output device for generating visible indicia in response to an output device signal and a processing circuit. The processing circuit reads the output data signals received by the input interface circuit, correlates these signals with the corresponding micro-locations, integrates the correlated output data signals for a desired time period by accumulating them in the data acquisition array, and generates the output device signal which, when applied to the output device, causes the output device to generate visible indicia related to the presence of the selected analytes.

In other embodiments, the chip is self-addressable. When using self-addressable-chips in the method, presently preferred are those adaptable to microelectronic self addressable, self-assembling chips and systems, such as those described in International PCT application Nos. WO 95/12808; WO 96/01836 and WO 96/07917 and also in arrays, such as those described in U.S. Pat. No. 5,451,683, which are each herein incorporated by reference. The self-addressable chips are such that each individual well may be addressed one at a time in the presence of the rest by changing the charge at a single microlocation and then sending the analytes or reagents via free flow electrophoresis throughout, but assembly occurs only at that location after the chip has been assembled. These devices are modified for use in the methods herein by replacing the disclosed detection means with the luciferase/luciferin systems.

In another embodiment provided herein, electrodes, an anode and cathode, are located at the bottom and top of each well, respectively, to allow for the delivery of analytes and reagents by free flow electrophoresis. The antibodies are attached to each location on a MYLAR (oriented polyethylene terephthalate) layer prior to assembling the chip (using, for example, a dot matrix printer). Thus, it is nonself-addressable in that is has a plurality of individual wells each containing a photodiode incorporated into the semiconductor layer at the bottom of each well.

In practice, for example, specific anti-ligands, ea., antibodies, may be attached directly to the matrix of the chip or to a middle reflective support matrix, such as heat stable MYLAR, positioned in the center of each well. The sample is contacted with the chip, washed and a plurality of secondary antibody-luciferase conjugates or protein fusions are added. The wells are washed and the remaining components of the bioluminescent reaction are added to initiate the reaction. Light produced in a well is detected by the photodiode, photomultiplier, CCD (charge coupled device) or other suitable detector in the semiconductor layer and the signal is relayed to a processing unit, typically a computer. The processing unit displays the well or wells that are positive. Each well corresponds to a particular ligand, thereby permitting identification of the infectious agents. All steps may be automated.

The design, fabrication, and uses of nonself-addressable and programmable, self-addressable and self-assembling microelectronic systems and devices which actively carry out controlled multi-step and multiplex reactions in microscopic formats for detecting the electromagnetic emissions of a bioluminescent reaction are provided herein. The reactions include, but are not limited to, most molecular biological procedures, such as nucleic acid and protein nucleic acid hybridizations, antibody/antigen reactions, and related clinical diagnostics.

The resulting chips, which includes a silicon matrix and photodiodes or other light detecting means, are provided. The silicon may be deposited using enzymatic deposition, similar to the enzymatic deposition by radiolarains and diatoms. Also provided are chips in which the absorption of silica or derivatives thereof is advantageously employed as a detection means. Such silica has an absorption maxima at about 705 nm, which is the wavelength emitted by Aristostomias bioluminescence generating system. Enzymatic methods for depositing silicon on the surface of a matrix are also provided herein.

Also provided herein is a synthetic synapse. A suitable enzyme, particularly, acetylcholine esterase is fused to a luciferase, such as by recombinant expression. The luciferase is either in an inactive or active conformation. Suitable mutations in either protein may be selected to insure that luciferase can undergo appropriate conformational changes as described herein. The resulting fusion is attached to a chip, such as a chip provided herein. Upon binding of the ligand to the enzyme, such as the binding of acetylcholine to the esterase, the linked luciferase is, if previously inactive, is activated by the binding, or if previously active, is inactivated by the binding. In the presence of the remaining components of a bioluminescence generating system, light is produced (or is quenched), which change is detected by the photodiodes associated with the chip. This detection generates an signal that is processed, such as by a computer, and is transmitted by appropriate means, such as fiber, to an electrode, which is attached to any desired device or effector, particularly a muscle. Upon receipt of the signal, work, such as a muscle twitch, occurs.

BRIEF DESCRIPTION OF THE DRAWINGS

FIG. 11 is a cross-section of an individual well indicating the relative positions of the CCD, reflective mirror layer and the cathode and anode. Antibodies attached to the middle reflective layer hang inverted above the photodiode. Bound antigen is detected using an antibody-luciferase fusion protein, and light generated from the bioluminescent reaction is detected by the photodiode and relayed to a processing unit for identification.

FIG. 12 is the cross-section of three self-addressable micro-locations fabricated using microlithographic techniques [see, International PCT application No. WO 96/01836]. Included are arrows denoting the positioning of photodiodes.

FIG. 13 is the cross-section of a microlithographically fabricated micro-location; antibodies or other receptors are linked to the attachment layer.

FIG. 19 depicts the methodology for the placement of silicon-synapses and electrodes in the human spinal cord to bypass a permanent spinal cord lesion.

DETAILED DESCRIPTION OF PREFERRED EMBODIMENTS

TABLE OF CONTENTS

Figure 1:
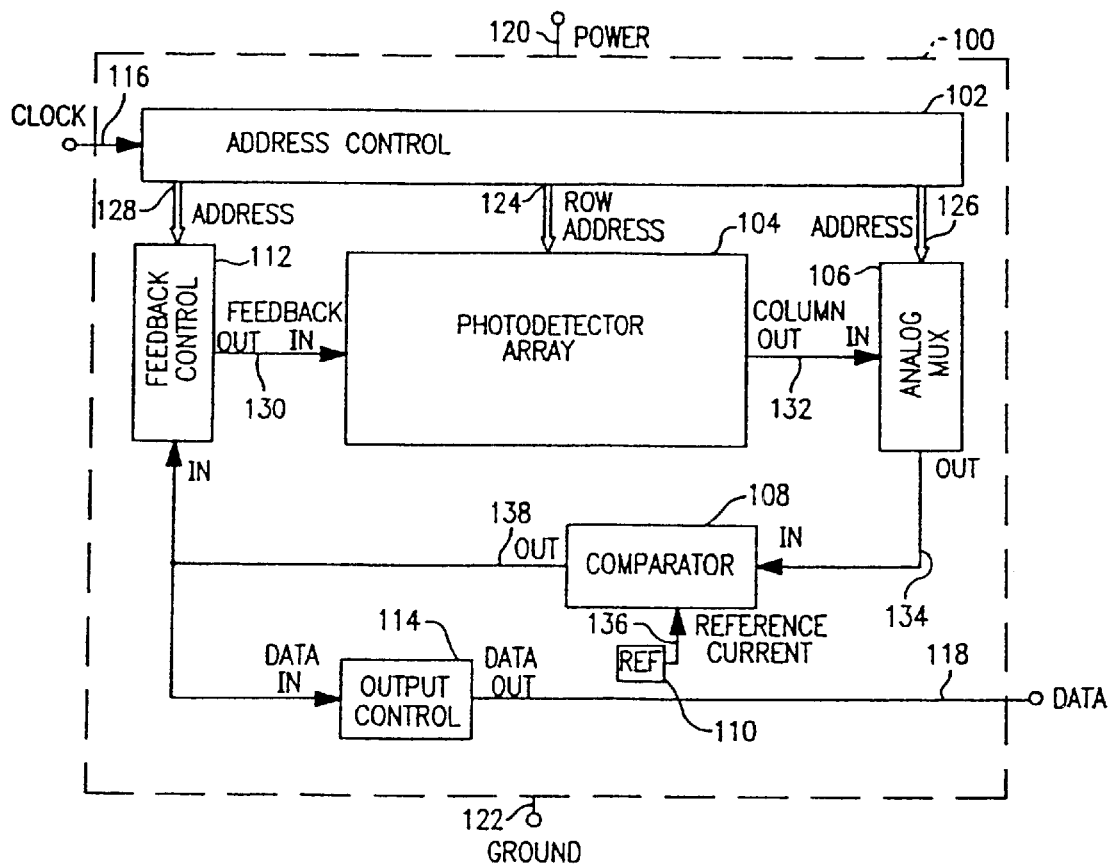
FIG. 1 is a schematic block diagram of a microelectronic device for detecting and identifying analytes in a biological sample using bioluminescence, the microelectronic device including an array of micro-locations and a photodetector optically coupled to each micro-location for detecting the bioluminescence emitted at the corresponding micro-location.

| | | | |
|---|---|---|---|
| A. | Definitions | | |
| B. | Bioluminescence generating systems | | |
| | 1. | General description | |
| | | a. | Luciferases |
| | | b. | Luciferins |
| | | c. | Activators |
| | | d. | Reactions |
| | 2. | Ctenophore and coelenterate systems | |
| | | a. | The aequorin system |
| | | | (1) Aequorin photoprotein |
| | | | (2) Luciferin |
| | | b. | The Renilla system |
| | 3. | Crustacean, particular Cyrpidina [Vargula], systems | |
| | | a. | Vargula luciferase |
| | | | (1) Purification from Cypridina |
| | | | (2) Preparation by Recombinant Methods |
| | | b. | Vargula luciferin |
| | | c. | Reaction |
| | 4. | Insect bioluminescence generating systems including fireflies, click beetles, and other insect systems | |
| | | a. | Luciferase |
| | | b. | Luciferin |
| | | c. | Reaction |
| | 5. | Bacterial systems | |
| | | a. | Luciferases |
| | | b. | Luciferins |
| | | c. | Reactions |
| | 6. | Other systems | |
| | | a. | Dinoflagellate bioluminescence generating systems |
| | | b. | Systems from molluscs, such as Latia and Pholas |
| | | c. | Earthworms and other annelids |
| | | d. | Glow worms |
| | | e. | Marine polycheate worm systems |
| | | f. | South American railway beetle |
| | 7. | Fluorescent proteins | |
| | | a. | Green and blue fluorescent proteins |
| | | b. | Phycobiliproteins |
| C. | Design and Fabrication of Chips | | |
| | 1. | Nonself-addressable chips | |
| | 2. | Self-addressable chips | |
| | | a. | Matrix materials |
| | | b. | Fabrication procedures |
| | | | i. Microlithography |
| | | | ii. Micromachining |
| | | c. | Self addressing of chips |

-continued

TABLE OF CONTENTS

3.    Attachment of biological molecules to chips
         a.    Derivatization of silica substrates
         b.    Attachment of biological molecules
  D.   Formation of luciferase conjugates
      1.    Linkers
      2.    Luciferase fusion proteins
      3.    Nucleic acid and peptide nucleic acid conjugates
  E.   Radiolarians and diatoms for deposition of silicon on matrices
  F.   Methods employing the chip A. Definitions Unless defined otherwise, all technical and scientific terms used herein have the same meaning as is commonly understood by one of skill in the art to which this invention belongs. All patents and publications referred to herein are incorporated by reference herein.

As used herein, chemiluminescence refers to a chemical reaction in which energy is specifically channeled to a molecule causing it to become electronically excited and subsequently to release a photon thereby emitting visible light. Temperature does not contribute to this channeled energy. Thus, chemiluminescence involves the direct conversion of chemical energy to light energy. Bioluminescence refers to the subset of chemiluminescence reactions that involve luciferins and luciferases (or the photoproteins). Bioluminescence does not herein include phosphorescence.

As used herein, bioluminescence, which is a type of chemi-luminescence, refers to the emission of light by biological molecules, particularly proteins. The essential condition for bioluminescence is molecular oxygen, either bound or free in the presence of an oxygenase, a luciferase, which acts on a substrate, a luciferin. Bioluminescence is generated by an enzyme or other protein [luciferase] that is an oxygenase that acts on a substrate luciferin [a bioluminescence substrate] in the presence of molecular oxygen and transforms the substrate to an excited state, which upon return to a lower energy level releases the energy in the form of light.

As used herein, the substrates and enzymes for producing bioluminescence are generically referred to as luciferin and luciferase, respectively. When reference is made to a particular species thereof, for clarity, each generic term is used with the name of the organism from which it derives, for example, bacterial luciferin or firefly luciferase.

As used herein, luciferase refers to oxygenases that catalyze a light emitting reaction. For instance, bacterial luciferases catalyze the oxidation of flavin mononucleotide [FMN] and aliphatic aldehydes, which reaction produces light. Another class of luciferases, found among marine arthropods, catalyzes the oxidation of Cypridina [Vargula] luciferin, and another class of luciferases catalyzes the oxidation-of Coleoptera luciferin.

Thus, luciferase refers to an enzyme or photoprotein that catalyzes a bioluminescent reaction [a reaction that produces bioluminescence]. The luciferases, such as firefly and Renilla luciferases, that are enzymes which act catalytically and are unchanged during the bioluminescence generating reaction. The luciferase photoproteins, such as the aequorin and obelin photoproteins to which luciferin is non-covalently bound, are changed, such as by release of the luciferin, during bioluminescence generating reaction. The luciferase is a protein that occurs naturally in an organism or a variant or mutant thereof, such as a variant produced by mutagenesis that has one or more properties, such as thermal or pH stability, that differ from the naturally-occurring protein. Luciferases and modified mutant or variant forms thereof are well known.

Thus, reference, for example, to "Renilla luciferase" means an enzyme isolated from member of the genus Renilla or an equivalent molecule obtained from any other source, such as from another Anthozoa, or that has been prepared synthetically.

The luciferases and luciferin and activators thereof are referred to as bioluminescence generating reagents or components. Typically, a subset of these reagents will be provided during the assay or otherwise immobilized at particular locations on the surface of the chip. Bioluminescence will be produced upon contacting the chip surface with the remaining reagents and the light produced is detected by the photodiodes at those locations of the array where a specific target has been detected by the immobilized anti ligand. Thus, as used herein, the component luciferases, luciferins, and other factors, such as $O_2$, $Mg^{2+}$, $Ca^{2+}$ are also referred to as bioluminescence generating reagents [or agents or components].

As used herein, "not strictly catalytically" means that the photoprotein acts as a catalyst to promote the oxidation of the substrate, but it is changed in the reaction, since the bound substrate is oxidized and bound molecular oxygen is used in the reaction. Such photoproteins are regenerated by addition of the substrate and molecular oxygen under appropriate conditions known to those of skill in this art.

As used herein, bioluminescence substrate refers to the compound that is oxidized in the presence of a luciferase, and any necessary activators, and generates light. These substrates are referred to as luciferins, which are substrates that undergo oxidation in a bioluminescence reaction. These bioluminescence substrates include any luciferin or analog thereof or any synthetic compound with which a luciferase interacts to generate light. Preferred substrates are those that are oxidized in the presence of a luciferase or protein in a light-generating reaction. Bioluminescence substrates, thus, include those compounds that those of skill in the art recognize as luciferins. Luciferins, for example, include firefly luciferin, Cypridina [also known as Vargula] luciferin [coelenterazine], bacterial luciferin, as well as synthetic analogs of these substrates or other compounds that are oxidized in the presence of a luciferase in a reaction the produces bioluminescence.

As used herein, capable of conversion into a bioluminescence substrate means susceptible to chemical reaction, such as oxidation or reduction, that yields a bioluminescence substrate. For example, the luminescence producing reaction of bioluminescent bacteria involves the reduction of a flavin mononucleotide group (FMN) to reduced flavin mononucleotide ($FMNH_2$) by a flavin reductase enzyme. The reduced flavin mononucleotide [substrate] then reacts with oxygen [an activator] and bacterial luciferase to form an intermediate peroxy flavin that undergoes further reaction, in the presence of a long-chain aldehyde, to generate light. With respect to this reaction, the reduced flavin and the long chain aldehyde are substrates.

As used herein, bioluminescence system [or bioluminescence generating system] refers to the set of reagents required for a bioluminescence-producing reaction. Thus, the particular luciferase, luciferin and other substrates, solvents and other reagents that may be required to complete a bioluminescent reaction form a bioluminescence system. Therefore, a bioluminescence system (or equivalently a bioluminescence generating system) refers to any set of reagents that, under appropriate reaction conditions, yield bioluminescence. Appropriate reaction conditions refers to the conditions necessary for a bioluminescence reaction to occur, such as pH, salt concentrations and temperature. In general, bioluminescence systems include a bioluminescence substrate (a luciferin), a luciferase, which includes enzymes luciferases and photoproteins, and one or more activators. A particular bioluminescence system may be identified by reference to the specific organism from which the luciferase derives; for example, the Vargula [also called Cypridina] bioluminescence system (or Vargula system) includes a Vargula luciferase, such as a luciferase isolated from the ostracod, Vargula or produced using recombinant means or modifications of these luciferases. This system would also include the particular activators necessary to complete the bioluminescence reaction, such as oxygen and a substrate with which the luciferase reacts in the presence of the oxygen to produce light.

As used herein, ATP, AMP, NAD+ and NADH refer to adenosine triphosphate, adenosine monophosphate, nicotinamide adenine dinucleotide (oxidized form) and nicotinamide adenine dinucleotide (reduced form), respectively.

As used herein, production by recombinant means by using recombinant DNA methods means the use of the well known methods of molecular biology for expressing proteins encoded by cloned DNA.

As used herein, substantially identical to a product means sufficiently similar so that the property of interest is sufficiently unchanged so that the substantially identical product can be used in place of the product.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein equivalent, when referring to two sequences of nucleic acids means that the two sequences in question encode the same sequence of amino acids or equivalent proteins. When "equivalent" is used in referring to two proteins or peptides, it means that the two proteins or peptides have substantially the same amino acid sequence with only conservative amino acid substitutions [see, eva., Table 2, below] that do not substantially alter the activity or function of the protein or peptide. When "equivalent" refers to a property, the property does not need to be present to the same extent [e.g., two peptides can exhibit different rates of the same type of enzymatic activity], but the activities are preferably substantially the same. "Complementary," when referring to two nucleotide sequences, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein: stringency of hybridization in determining percentage mismatch is as follows:

| | |
|---|---|
| 1) high stringency: | 0.1 × SSPE, 0.1% SDS, 65° C. |
| 2) medium stringency: | 0.2 × SSPE, 0.1% SDS, 50° C. |
| 3) low stringency: | 1.0 × SSPE, 0.1% SDS, 50° C. |

It is understood that equivalent stringencies may be achieved using alternative buffers, salts and temperatures.

As used herein, peptide nucleic acid refers to nucleic acid analogs in which the ribose-phosphate backbone is replaced by a backbone held together by amide bonds.

The term "substantially" varies with the context as understood by those skilled in the relevant art and generally means at least 70%, preferably means at least 80%, more preferably at least 90%, and most preferably at least 95%.

As used herein, biological activity refers to the in vivo activities of a compound or physiological responses that result upon administration of a compound, composition or other mixture. Biological activities may be observed in in vitro systems designed to test or use such activities. Thus, for purposes herein the biological activity of a luciferase is its oxygenase activity whereby, upon oxidation of a substrate, light is produced.

As used herein, a composition refers to a any mixture. It may be a solution, a suspension, liquid, powder, a paste, aqueous, non-aqueous or any combination thereof.

As used herein, a combination refers to any association between two or among more items.

As used herein, fluid refers to any composition that can flow. Fluids thus encompass compositions that are in the form of semi-solids, pastes, solutions, aqueous mixtures, gels, lotions, creams and other such compositions.

As used herein, macromolecules are intended to generically encompass all molecules that would be linked to a solid support for diagnostic assays. The macromolecules include, but are not limited to: proteins, organic molecules, nucleics acids, viruses, viral capsids, phage, cells or membranes thereof or portions of viruses, viral capsids, phage, cells or membranes. Of particular interest herein, are macromolecules that specifically bind to an analyte of interest. Analytes of interest are those present in body fluids and other biological samples.

As used herein, a receptor refers to a molecule that has an affinity for a given ligand. Receptors may be naturally-occurring or synthetic molecules. Receptors may also be referred to in the art as anti-ligands. As used herein, the receptor and anti-ligand are interchangeable. Receptors can be used in their unaltered state or as aggregates with other species. Receptors may be attached, covalently or noncovalently, or in physical contact with, to a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants [such as on viruses, cells, or other materials], drugs, polynucleotides, nucleic acids, peptides, cofactors, lectins, sugars, polysaccharides, cells, cellular membranes, and organelles.

Examples of receptors and applications using such receptors, include but are not restricted to:

a) enzymes: specific transport proteins or enzymes essential to survival of microorganisms, which could serve as targets for antibiotic [ligand] selection;

b) antibodies: identification of a ligand-binding site on the antibody molecule that combines with the epitope of an antigen of interest may be investigated; determination of a sequence that mimics an antigenic epitope may lead to the development of vaccines of which the immunogen is based on one or more of such sequences or lead to the development of related diagnostic agents or compounds useful in therapeutic treatments. such as for auto-immune diseases c) nucleic acids: identification of ligand, such as protein or RNA, binding sites;

d) catalytic polypeptides: polymers, preferably polypeptides, that are capable of promoting a chemical reaction involving the conversion of one or more reactants to one or more products; such polypeptides generally include a binding site specific for at least one reactant or reaction intermediate and an active functionality proximate to the binding site, in which the functionality is capable of chemically modifying the bound reactant [see, e.g., U.S. Pat. No. 5,21 5,899];

e) hormone receptors: determination of the ligands that bind with high affinity to a receptor is useful in the development of hormone replacement therapies; for example, identification of ligands that bind to such receptors may lead to the development of drugs to control blood pressure; and f) opiate receptors: determination of ligands that bind to the opiate receptors in the brain is useful in the development of less-addictive replacements for morphine and related drugs.

As used herein, antibody includes antibody fragments, such as Fab fragments, which are composed of a light chain and the variable region of a heavy chain.

As used herein, complementary refers to the topological compatibility or matching together of interacting surfaces of a ligand molecule and its receptor. Thus, the receptor and its ligand can be described as complementary, and furthermore, the contact surface characteristics are complementary to each other.

As used herein, a ligand-receptor pair or complex formed when two macromolecules have combined through molecular recognition to form a complex.

As used herein, an epitope refers to a portion of an antigen molecule that is delineated by the area of interaction with the subclass of receptors known as antibodies.

As used herein, a ligand is a molecule that is specifically recognized by a particular receptor. Examples of ligands, include, but are not limited to, agonists and antagonists for cell membrane receptors, toxins and venoms, viral epitopes, hormones [e.g., steroids], hormone receptors, opiates, peptides, enzymes, enzyme substrates, cofactors, drugs, lectins, sugars, oligonucleotides, nucleic acids, oligosaccharides, proteins, and monoclonal antibodies.

As used herein, an anti-ligand (AL.sub.i): An anti-ligand is a molecule that has a known or unknown affinity for a given ligand and can be immobilized on a predefined region of the surface. Anti-ligands may be naturally-occurring or manmade molecules. Also, they can be employed in their unaltered state or as aggregates with other species. Anti-ligands may be reversibly attached, covalently or noncovalently, to a binding member, either directly or via a specific binding substance. By "reversibly attached" is meant that the binding of the anti-ligand (or specific binding member or ligand) is reversible and has, therefore, a substantially non-zero reverse, or unbinding, rate. Such reversible attachments can arise from noncovalent interactions, such as electrostatic forces, van der Waals forces, hydrophobic (i.e., entropic) forces, and the like. Furthermore, reversible attachments also may arise from certain, but not all covalent bonding reactions. Examples include, but are not limited to, attachment by the formation of hemiacetals, hemiketals, imines, acetals, ketals, and the like (See, Morrison et al., "Organic Chemistry", 2nd ed., ch. 19 (1966), which is incorporated herein by reference). Examples of anti-ligands which can be employed in the methods and devices herein include, but are not limited to, cell membrane receptors, monoclonal antibodies and antisera reactive with specific antigenic determinants (such as on viruses, cells or other materials), hormones, drugs, oligonucleotides, peptides, peptide nucleic acids, enzymes, substrates, cofactors, lectins, sugars, oligosaccharides, cells, cellular membranes, and organelles.

As used herein, a substrate refers to any matrix that is used either directly or following suitable derivatization, as a solid support for chemical synthesis, assays and other such processes. Preferred substrates herein, are silicon substrates or siliconized substrates that are derivatized on the surface intended for linkage of anti-ligands and ligands and other macromolecules, including the fluorescent proteins, phycobiliproteins and other emission shifters.

As used herein, a matrix refers to any solid or semisolid or insoluble support on which the molecule of interest, typically a biological molecule, macromolecule, organic molecule or biospecific ligand is linked or contacted. Typically a matrix is a substrate material having a rigid or semi-rigid surface. In many embodiments, at least one surface of the substrate will be substantially flat, although in some embodiments it may be desirable to physically separate synthesis regions for different polymers with, for example, wells, raised regions, etched trenches, or other such topology. Matrix materials include any materials that are used as affinity matrices or supports for chemical and biological molecule syntheses and analyses, such as, but are not limited to: polystyrene, polycarbonate, polypropylene, nylon, glass, dextran, chitin, sand, pumice, polytetrafluoroethylene, agarose, polysaccharides, dendrimers, buckyballs, polyacrylamide, Kieselguhr-polyacrlamide non-covalent composite, polystyrene-polyacrylamide covalent composite, polystyrene-PEG [polyethyleneglycol] composite, silicon, rubber, and other materials used as supports for solid phase syntheses, affinity separations and purifications, hybridization reactions, immunoassays and other such applications.

As used herein, the attachment layer refers the surface of the chip device to which molecules are linked. Typically, the chip is a semiconductor device, which is coated on a least a portion of the surface to render it suitable for linking molecules and inert to any reactions to which the device is exposed. Molecules are linked either directly or indirectly to the surface, linkage may be effected by absorption or adsorption, through covalent bonds, ionic interactions or any other interaction. Where necessary the attachment layer is adapted, such as by derivatization for linking the molecules.

B. Bioluminescence Generating Systems

A bioluminescence generating system refers to the components that are necessary and sufficient to generate bioluminescence. These include a luciferase, luciferin and any necessary co-factors or conditions. Virtually any bioluminescence generating system known to those of skill in the art will be amenable to use in the apparatus, systems, combinations and methods provided herein. Factors for consideration in selecting a bioluminescence generating system, include, but are not limited to: the desired assay and biological fluid used in combination with the bioluminescence; the medium in which the reaction is run; stability of the components, such as temperature or pH sensitivity; shelf life of the components; sustainablity of the light emission, whether constant or intermittent; availability of components; desired light intensity; and other such factors.

1. General Description

In general, bioluminescence refers to an energy-yielding chemical reaction in which a specific chemical substrate, a luciferin, undergoes oxidation, catalyzed by an enzyme, a luciferase. Bioluminescent reactions are easily maintained, requiring only replenishment of exhausted luciferin or other substrate or cofactor or other protein, in order to continue or revive the reaction. Bioluminescence generating reactions are well known to those of skill in this art and any such reaction may be adapted for use in combination with apparatus, systems and methods described herein.

There are numerous organisms and sources of bioluminescence generating systems, and some representative genera and species that exhibit bioluminescence are set forth in the following table [reproduced in part from Hastings in (1995) *Cell Physiology:Source Book*, N. Sperelakis (ed.), Academic Press, pp 665–681]:

TABLE 1

Representative luminous organism

| Type of Organism | Representative genera |
|---|---|
| Bacteria | Photobacterium |
|  | Vibrio |
|  | Xenorhabdus |
| Mushrooms | Panus, Armillaria |
|  | Pleurotus |
| Dinoflagellates | Gonyaulax |
|  | Pyrocystis |
|  | Noctiluca |
| Cnidaria (coelenterates) | |
| Jellyfish | Aequorea |
| Hydroid | Obelia |
| Sea Pansy | Renilla |
| Ctenophores | Mnemiopsis |
|  | Beroe |
| Annelids | |
| Earthworms | Diplocardia |
| Marine polychaetes | Chaetopterus, Phyxotrix |
| Syllid fireworm | Odontosyllis |
| Molluscs | |
| Limpet | Latia |
| Clam | Pholas |
| Squid | Heteroteuthis |
|  | Heterocarpus |
| Crustacea | |
| Ostracod | Vargula (Cypridina) |
| Shrimp (euphausids) | Meganyctiphanes |
|  | Acanthophyra |
|  | Oplophorus |
|  | Gnathophausia |
| Decapod | Sergestes |
| Copepods | |
| Insects | |
| Coleopterids (beetles) | |
| Firefly | Photinus, Photuris |
| Click beetles | Pyrophorus |
| Railroad worm | Phengodes, Phrixothrix |
| Diptera (flies) | Arachnocampa |
| Echinoderms | |
| Brittle stars | Ophiopsila |
| Sea cucumbers | Laetmogone |

TABLE 1-continued

Representative luminous organism

| Type of Organism | Representative genera |
|---|---|
| Chordates | |
| Tunicates | Pyrosoma |
| Fish | |
| Cartilaginous | Squalus |
| Bony | |
| Ponyfish | Leiognathus |
| Flashlight fish | Photoblepharon |
| Angler fish | Cryptopsaras |
| Midshipman | Porichthys |
| Lantern fish | Benia |
| Shiny loosejaw | Aristostomias |
| Hatchet fish and | Agyropelecus |
| other fish | Pachystomias |
|  | Malacosteus |
| Midwater fish | Cyclothone |
|  | Neoscopelus |
|  | Tarletonbeania |

Other bioluminescent organisms contemplated for use as sources of bioluminescence generating systems herein include, but are not limited to, Gonadostomias, Gaussia, Halisturia, Vampire squid, Glyphus, Mycotophids (fish), Vinciguerria, Howella, Florenciella, Chaudiodus, Melanocostus, Paracanthus, Atolla, Pelagia, Pitilocarpus, Acanthophyra, Siphonophore, Periphylla and Sea Pens (Stylata).

It is understood that a bioluminescence generating system may be isolated from natural sources, such as those in the above Table, or may be produced synthetically. In addition, for uses herein, the components need only be sufficiently pure so that mixture thereof, under appropriate reaction conditions, produces a glow. Thus it has been found, in some embodiments, a crude extract or merely grinding up the organism may be adequate. Generally, however, substantially pure components are used, but, where necessary, the precise purity can be determined empirically. Also, components may be synthetic components that are not isolated from natural sources. DNA encoding luciferases is available [see, e.g., SEQ ID Nos. 1–13] and has been modified [see, e.g., SEQ ID Nos. 3 and 10–13] and synthetic and alternative substrates have been devised. The DNA listed herein is only representative of the DNA encoding luciferases that is available.

Any bioluminescence generating system, whether synthetic or isolated form natural sources, such as those set forth in Table 1, elsewhere herein or known to those of skill in the art, is intended for use in the chip devices, combinations, systems and methods provided herein. Chemiluminescence systems per se, which do not rely on oxygenases [luciferases] are not encompassed herein.

a. Luciferases

Luciferases refer to any compound that, in the presence of any necessary activators, catalyze the oxidation of a bioluminescence substrate [luciferin] in the presence of molecular oxygen, whether free or bound, from a lower energy state to a higher energy state such that the substrate, upon return to the lower energy state, emits light. For purposes herein, luciferase is broadly used to encompass enzymes that act catalytically to generate light by oxidation of a substrate and also photoproteins, such as aequorin, that act, though not strictly catalytically [since such proteins are exhausted in the reaction], in conjunction with a substrate in the presence of oxygen to generate light. These luciferases, including photoproteins, such as aequorin, are herein also included, among the luciferases. These reagents include the naturally-occurring luciferases [including photoproteins], proteins produced by recombinant DNA, and mutated or modified variants thereof that retain the ability to generate light in the presence of an appropriate substrate, co-factors and activators or any other such protein that acts as a catalyst to oxidize a substrate, whereby light is produced.

Generically, the protein that catalyzes or initiates the bioluminescent reaction is referred to as a luciferase, and the oxidizable substrate is referred to as a luciferin. The oxidized reaction product is termed oxyluciferin, and certain luciferin precursors are termed etioluciferin. Thus, for purposes herein bioluminescence encompasses light produced by reactions that are catalyzed by [in the case of luciferases that act enzymatically] or initiated by [in the case of the photoproteins, such as aequorin, that are not regenerated in the reaction] a biological protein or analog, derivative or mutant thereof.

For clarity herein, these catalytic proteins are referred to as luciferases and include enzymes such as the luciferases that catalyze the oxidation of luciferin, emitting light and releasing oxyluciferin. Also included among luciferases are photoproteins, which catalyze the oxidation of luciferin to emit light but are changed in the reaction and must be reconstituted to be used again. The luciferases may be naturally occurring or may be modified, such as by genetic engineering to improve or alter certain properties. As long as the resulting molecule retains the ability to catalyze the bioluminescent reaction, it is encompassed herein.

Any protein that has luciferase activity [a protein that catalyzes oxidation of a substrate in the presence of molecular oxygen to produce light as defined herein] may be used herein. The preferred luciferases are those that are described herein or that have minor sequence variations. Such minor sequence variations include, but are not limited to, minor allelic or species variations and insertions or deletions of residues, particularly cysteine residues. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, em., Watson et al. *Molecular Biology of the Gene,* 4th Edition, 1987, The Benjamin/Cummings Pub. co., p.224). Such substitutions are preferably made in accordance with those set forth in TABLE 2 as follows:

TABLE 2

| Original residue | Conservative substitution |
| --- | --- |
| Ala (A) | Gly; Ser |
| Arg (R) | Lys |
| Asn (N) | Gln; His |
| Cys (C) | Ser; neutral amino acid |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |

TABLE 2-continued

| Original residue | Conservative substitution |
| --- | --- |
| Trp (W) | Tyr |
| Tyr (Y) | Trp; Phe |
| Val (V) | Ile; Leu |

Other substitutions are also permissible and may be determined empirically or in accord with known conservative substitutions. Any such modification of the polypeptide may be effected by any means known to those of skill in this art.

The luciferases may be obtained commercially, isolated from natural sources, expressed in host cells using DNA encoding the luciferase, or obtained in any manner known to those of skill in the art. For purposes herein, crude extracts obtained by grinding up selected source organisms may suffice. Since large quantities of the luciferase may be desired, isolation of the luciferase from host cells is preferred. DNA for such purposes is widely available as are modified forms thereof.

Examples of luciferases include, but are not limited to, those isolated from the ctenophores Mnemiopsis (mnemiopsin) and *Beroe ovata* (berovin), those isolated from the coelenterates Aequorea (aequorin), Obelia (obelin), Pelagia, the Renilla luciferase, the luciferases isolated from the mollusca Pholas (pholasin), the luciferases isolated from the Aristostomias and Porichthys fish and from the ostracods, such as Cypridina (also referred to as Vargula). Preferred luciferases for use herein are the Aequorin protein, Renilla luciferase and Cypridina [also called Vargula] luciferase [see, e.g., SEQ ID Nos. 1, 2, and 4–13]. Also, preferred are luciferases which react to produce red and/or near infrared light. These include luciferases found in species of Aristostomias, such as *A. scintillans,* Pachystomias, Malacosteus, such as *M. niger.* b. Luciferins

The substrates for the reaction include any molecule(s) with which the luciferase reacts to produce light. Such molecules include the naturally-occurring substrates, modified forms thereof, and synthetic substrates [see, e.g., U.S. Pat. Nos. 5,374,534 and 5,098,828]. Exemplary luciferins include those described herein, as well as derivatives thereof, analogs thereof, synthetic substrates, such as dioxetanes [see, e.g., U.S. Pat. Nos. 5,004,,565 and 5,455,357], and other compounds that are oxidized by a luciferase in a light-producing reaction [see, e.g. U.S. Pat. Nos. 5,374,534, 5,098,828 and 4,950,588]. Such substrates also may be identified empirically by selecting compounds that are oxidized in bioluminescent reactions.

c. Activators

The bioluminescence generating systems also require additional components discussed herein and known to those of skill in the art. All bioluminescent reactions require molecular oxygen in the form of dissolved or bound oxygen. Thus, molecular oxygen, dissolved in water or in air or bound to a photoprotein, is the activator for bioluminescence reactions. Depending upon the form of the components, other activators include, but are not limited to, ATP [for firefly luciferase], flavin reductase [bacterial systems] for regenerating $FMNH_2$ from FMN, and $Ca^{2+}$ or other suitable metal ion [aequorin].

Most of the systems provided herein will generate light when the luciferase and luciferin are mixed and exposed to air or water. The systems that use photoproteins that have bound oxygen, such as aequorin, however, will require exposure to $Ca^{2+}$ [or other suitable metal ion], which can be provided in the form of an aqueous composition of a calcium salt. In these instances, addition of a $Ca^{2+}$ [or other suitable metal ion] to a mixture of luciferase [aequorin] and luciferin [such as coelenterazine] will result in generation of light. The Renilla system and other Anthozoa systems also require $Ca^{2+}$ [or other suitable metal ion].

If crude preparations are used, such as ground up Cypridina [shrimp] or ground fireflies, it may be necessary to add only water. In instances in which fireflies [or a firefly or beetle luciferase] are used the reaction may only require addition ATP. The precise components will be apparent, in light of the disclosure herein, to those of skill in this art or may be readily determined empirically.

It is also understood that these mixtures will also contain any additional salts or buffers or ions that are necessary for each reaction to proceed. Since these reactions are well-characterized, those of skill in the art will be able to determine precise proportions and requisite components. Selection of components will depend upon the chip device and system, the assay to be preformed and the luciferase. Various embodiments are described and exemplified herein; in view of such description, other embodiments will be apparent.

d. Reactions

In all embodiments, up to all but one component of a bioluminescence generating system will be bound directly or indirectly to the appropriate locations of the chip or otherwise immobilized at those positions of the array in which the presence of analyte, preferably an infectious agent, is detected. When bioluminescence is desired, the remaining component(s) will be added to the surface of the chip and the light produced at those locations of the array is detected by the photodiodes of the chip.

In general, since the result to be achieved is the production of light that can be detected by the photodiodes of the chip or visible to the naked eye for the purposes herein, the precise proportions and amounts of components of the bioluminescence reaction need not be stringently determined or met. They must be sufficient to produce light. Generally, an amount of luciferin and luciferase sufficient to generate a readily detectable signal or a visible glow is used; this amount can be readily determined empirically and is dependent upon the selected system and selected application.

For purposes herein, such amount is preferably at least the concentrations and proportions used for analytical purposes by those of skill in the such arts. Higher concentrations or longer integration times may be used if the glow is not sufficiently bright to be detected by photodiodes in the chip. Also because the conditions in which the reactions are used are not laboratory conditions and the components are subject to storage, higher concentration may be used to overcome any loss of activity. Typically, the amounts are 1 mg, preferably 10 mg and more preferably 100 mg, of a luciferase per liter of reaction mixture or 1 mg, preferably 10 mg, more preferably 100 mg. Such luciferases may be produced by drying a composition containing at least about 0.01 mg/l, and typically 0.1 mg/l, 1 mg/l, 10 mg/l or more of each component. The amount of luciferin is also between about 0.01 and 100 mg/l, preferably between 0.1 and 10 mg/l, additional luciferin can be added to many of the reactions to continue the reaction. In embodiments in which the luciferase acts catalytically and does not need to be regenerated, lower amounts of luciferase can be used. In those in which it is changed during the reaction, it also can be replenished; typically higher concentrations will be selected. Ranges of concentration per liter [or the amount of coating on substrate the results from contacting with such composition] of each component on the order of 0.1 to 20 mg, preferably 0.1 to 10 mg, more preferably between about 1 and 10 mg of each component will be sufficient. When preparing coated substrates, as described herein, greater amounts of coating compositions containing higher concentrations of the luciferase or luciferin may be used.

Thus, for example, in presence of calcium, 5 mg of luciferin, such as coelenterazine, in one liter of water will glow brightly for at least about 10 to 20 minutes, depending on the temperature of the water, when about 10 mgs of luciferase, such as aequorin photoprotein luciferase or luciferase from Renilla, is added thereto. Increasing the concentration of luciferase, for example, to 100 mg/l, provides a particularly brilliant display of light.

If desired, the onset of the bioluminescent reaction can be delayed by adding an, an inhibitor, for example magnesium, of the bioluminescence generating reaction. Also, where inhibition is not desired, the concentration of free magnesium may be reduced by addition of a sufficient amount of chelating agent, such as ethylenediaminetetraacetic acid [EDTA]. The amount of EDTA and also calcium can be empirically determined to appropriately chelate magnesium, without inhibiting or preventing the desired bioluminescence.

It is understood, that concentrations and amounts to be used depend upon the selected luciferase, the desired bacterial target, the concentration and amount of light absorbed by the immobilized anti ligand, the size of the photodiode array and these may be readily determined empirically. Proportions, particularly those used when commencing an empirical determination, are generally those used for analytical purposes, and amounts or concentrations are at least those used for analytical purposes, but the amounts can be increased, particularly if a sustained and brighter glow is desired.

2. Ctenophore and Coelenterate Systems

Ctenophores, such as Mnemiopsis (mnemiopsin) and *Beroe ovata* (berovin), and coelenterates, such as Aequorea (aequorin), Obelia (obelin) and Pelagia, produce bioluminescent light using similar chemistries [see, e.g. Stephenson et al. (1981) *Biochimica et Biophysica Acta* 678:65–75; Hart et al. (1979) *Biochemistry* 18:2204–2210; International PCT Application No. WO94/18342, which is based on U.S. application Ser. No. 08/017,116, U.S. Pat. No. 5,486,455 and other references and patents cited herein]. The Aequorin and Renilla systems are representative and are described in detail herein as exemplary and as among the presently preferred systems. The Aequorin and Renilla systems can use the same luciferin and produce light using the same chemistry, but each luciferase is different. The Aequorin luciferase aequorin, as well as, for example, the luciferases mnemiopsin and berovin, is a photoprotein that includes bound oxygen and bound luciferin, requires $Ca^{2+}$ [or other suitable metal ion] to trigger the reaction, and must be regenerated for repeated use; whereas, the Renilla luciferase acts as a true enzyme because it is unchanged during the reaction and it requires dissolved molecular oxygen.

a. The Aequorin System

The aequorin system is well known [see, e.g., Tsuji et al. (1986) "Site-specific mutagenesis of the calcium-binding photoprotein aequorin," *Proc. Natl. Acad. Sci. USA* 83:8107–8111; Prasher et al. (1985) "Cloning and Expression of the cDNA Coding for Aequorin, a Bioluminescent Calcium-Binding Protein," *Biochemical and Biophysical Research Communications* 126:1259–1268; Prasher et al.

(1986) *Methods in Enzymology* 133:288–297; Prasher, et al. (1987) "Sequence Comparisons of cDNAs Encoding for Aequorin Isotypes," *Biochemistry* 26:1326–1332; Charbonneau et al. (1985) "Amino Acid Sequence of the Calcium-Dependent Photoprotein Aequorin," *Biochemistry* 24:6762–677 1; Shimomura et al. (1 981) "Resistivity to denaturation of the apoprotein of aequorin and reconstitution of the luminescent photoprotein from the partially denatured apoprotein," *Biochem. J.* 199:825–828; Inouye et al. (1989) *J. Biochem.* 105:473–477; Inouye et al. (1986) "Expression of Apoaequorin Complementary DNA in *Escherichia coli*," *Biochemistry* 25:8425–8429; Inouye et al. (1985) "Cloning and sequence analysis of cDNA for the luminescent protein aequorin," *Proc. Natl. Acad. Sci. USA* 82:3154–3158; Prendergast, et al. (1978) "Chemical and Physical Properties of Aequorin and the Green Fluorescent Protein Isolated from *Aequorea forskalea*" *J. Am. Chem. Soc.* 17:3448–3453; European Patent Application 0 540 064 A1; European Patent Application 0 226 979 A2, European Patent Application 0 245 093 A1 and European Patent Specification 0 245 093 B1; U.S. Pat. No. 5,093,240; U.S. Pat. No. 5,360,728; U.S. Pat. No. 5,139,937; U.S. Pat. No. 5,422,266; U.S. Pat. No. 5,023,181; U.S. Pat. No. 5,162,227; and SEQ ID Nos. 5–13, which set forth DNA encoding the apoprotein; and a form, described in U.S. Pat. No. 5,162,227, European Patent Application 0 540 064 A1 and Sealite Sciences Technical Report No. 3 (1994), is commercially available from Sealite, Sciences, Bogart, Ga. as AQUALITE®].

This system is among the preferred systems for use herein. As will be evident, since the aequorin photoprotein includes noncovalently bound luciferin and molecular oxygen, it is suitable for storage in this form as a lyophilized powder or encapsulated into a selected delivery vehicle. The system can be encapsulated into pellets, such as liposomes or other delivery vehicles, or stored in single chamber dual or other multiple chamber ampules. When used, the photoproteins will be conjugated to an anti ligand, bound to the specified positions in the array and contacted with a composition, even tap water, that contains $Ca^{2+}$ [or other suitable metal ion], to produce a mixture that glows at that particular location of the array. The light is detected by the photodiodes in the chip and the data signals are analyzed by the associated computer processor. This system is preferred for use in numerous embodiments herein.

(1) Aequorin and Related Photoproteins

The photoprotein, aequorin, isolated from the jellyfish, Aequorea, emits light upon the addition of $Ca^{2+}$ [or other suitable metal ion]. The aequorin photoprotein, which includes bound luciferin and bound oxygen that is released by $Ca^{2+}$, does not require dissolved oxygen. Luminescence is triggered by calcium, which releases oxygen and the luciferin substrate producing apoaqueorin.

The bioluminescence photoprotein aequorin is isolated from a number of species of the jellyfish Aequorea. It is a 22 kilodalton [kD] molecular weight peptide complex [see, e.g, Shimomura et al. (1962) *J. Cellular and Comp. Physiol.* 59:233–238; Shimomura et al. (1969) *Biochemistry* 8:3991–3997; Kohama et al. (1971) *Biochemistry* 10:4149–4152; and Shimomura et al. (1972) *Biochemistry* 11:1602–1608]. The native protein contains oxygen and a heterocyclic compound coelenterazine, a luciferin, [see, below] noncovalently bound thereto. The protein contains three calcium binding sites. Upon addition of trace amounts $Ca^{2+}$ [or other suitable metal ion, such as strontium] to the photoprotein, it undergoes a conformational change the catalyzes the oxidation of the bound coelenterazine using the protein-bound oxygen. Energy from this oxidation is released as a flash of blue light, centered at 469 nm. Concentrations of calcium ions as low as $10^{-6}$ M are sufficient to trigger the oxidation reaction.

Naturally-occurring apoaequorin is not a single compound but rather is a mixture of microheterogeneous molecular species. Aequoria jellyfish extracts contain as many as twelve distinct variants of the protein [see, e.g., Prasher et al. (187) *Biochemistry* 26:1326–1332; Blinks et al. (1975) *Fed. Proc.* 34:474]. DNA encoding numerous forms has been isolated [see, e.g., SEQ ID Nos. 5–9 and 13].

The photoprotein can be reconstituted [see, e.g., U.S. Pat. No. 5,023,181] by combining the apoprotein, such as a protein recombinantly produced in *E. coli*, with a coelenterazine, such as a synthetic coelenterazine, in the presence of oxygen and a reducing agent [see, e.g., Shimomura et al. (1975) *Nature* 256:236–238; Shimomura et al. (1981) *Biochemistry J.* 199:825–828], such as 2-mercaptoenthanol, and also EDTA or EGTA [concentrations between about 5 to about 100 mM or higher for applications herein] tie up any $Ca^{2+}$ to prevent triggering the oxidation reaction until desired. DNA encoding a modified form of the apoprotein that does not require 2-mercaptoethanol for reconstitution is also available [see, e.g., U.S. Pat. No. 5,093,2401. The reconstituted photoprotein is also commercially available [sold, e.g, under the trademark AQUALITE®, which is described in U.S. Pat. No. 5,162,227].

The light reaction is triggered by adding $Ca^{2+}$ at a concentration sufficient to overcome the effects of the chelator and achieve the $10^{-6}$ M concentration. Because such low concentrations of $Ca^{2+}$ can trigger the reaction, for use in the methods herein, higher concentrations of chelator may be included in the compositions of photoprotein. Accordingly, higher concentrations of added $Ca^{2+}$ in the form of a calcium salt will be required. Precise amounts may be empirically determined. For use herein, it may be sufficient to merely add water to the photoprotein, which is provided in the form of a concentrated composition or in lyophilized or powdered form. Thus, for purposes herein, addition of small quantities of $Ca^{2+}$, such as those present in most tap water or in phosphate buffered saline (PBS) or other suitable buffers or possible in the moisture on the skin, should trigger the bioluminescence reaction.

Numerous isoforms of the aequorin apoprotein been identified isolated. DNA encoding these proteins has been cloned, and the proteins and modified forms thereof have been produced using suitable host cells [see,e, U.S. Pat. Nos. 5,162,227, 5,360,728, 5,093,240; see, also, Prasher et al. (1985) *Biophys. Biochem. Res. Commun.* 126:1259–1268; Inouye et al. (1986) *Biochemistry* 25: 8425–8429]. U.S. Pat. No. 5,093,240; U.S. Pat. No. 5,360,728; U.S. Pat. No. 5,139,937; U.S. Pat. No. 5,288,623; U.S. Pat. No. 5,422,266, U.S. Pat. No. 5,162,227 and SEQ ID Nos. 5–13, which set forth DNA encoding the apoprotein; and a form is commercially available form Sealite, Sciences, Bogart, Ga. as AQUALITE®]. DNA encoding apoaequorin or variants thereof is useful for recombinant production of high quantities of the apoprotein. The photoprotein is reconstituted upon addition of the luciferin, coelenterazine, preferably a sulfated derivative thereof, or an analog thereof, and molecular oxygen [see, e.g., U.S. Pat. No. 5,023,181]. The apoprotein and other constituents of the photoprotein and bioluminescence generating reaction can be mixed under appropriate conditions to regenerate the photoprotein and concomitantly have the photoprotein produce light. Reconstitution requires the presence of a reducing agent, such as mercaptoethanol, except for modified forms, discussed below, that are designed so that a reducing agent is not required [see, e.g., U.S. Pat. No. 5,093,240].

For use herein, it is preferred aequorin is produced using DNA, such as that set forth in SEQ ID Nos. 5–13 and known to those of skill in the art or modified forms thereof. The DNA encoding aequorin is expressed in a host cell, such as *E. coli*, isolated and reconstituted to produce the photoprotein [see, e.g., U.S. Pat. Nos. 5,418,155, 5,292,658, 5,360,728, 5,422,266, 5,162,227].

Of interest herein, are forms of the apoprotein that have been modified so that the bioluminescent activity is greater than unmodified apoaequorin [see, e.g., U.S. Pat. No. 5,360,728, SEQ ID Nos. 10–12]. Modified forms that exhibit greater bioluminescent activity than unmodified apoaequorin include proteins having sequences set forth in SEQ ID Nos. 10–12, in which aspartate 124 is changed to serine, glutamate 135 is changed to serine, and glycine 129 is changed to alanine, respectively. Other modified forms with increased bioluminescence are also available.

For use in certain embodiments herein, the apoprotein and other components of the aequorin bioluminescence generating system are packaged or provided as a mixture, which, when desired is subjected to conditions under which the photoprotein reconstitutes from the apoprotein, luciferin and oxygen [see, e.g., U.S. Pat. No. 5,023,181; and U.S. Pat. No. 5,093,240]. Particularly preferred are forms of the apoprotein that do not require a reducing agent, such as 2-mercaptoethanol, for reconstitution. These forms, described, for example in U.S. Pat. No. 5,093,240[see, also Tsuji et al. (1986) *Proc. Natl. Acad. Sci. U.S.A.* 83:8107–8111], are modified by replacement of one or more, preferably all three cysteine residues with, for example serine. Replacement may be effected by modification of the DNA encoding the aequorin apoprotein, such as that set forth in SEQ ID No. 5, and replacing the cysteine codons with serine.

The photoproteins and luciferases from related species, such as Obelia are also contemplated for use herein. DNA encoding the $Ca^{2+}$-activated photoprotein obelin from the hydroid polyp *Obelia longissima* is known and available [see, e.g., Illarionov et al. (1995) *Gene* 153:273–274; and Bondar et al. (1995) *Biochim. Biophys. Acta* 1231:29–32]. This photoprotein can also be activated by $Mn^{2+}$ [see, e.g., Vysotski et al. (1995) *Arch. Bioch. Biophys.* 316:92–93, Vysotski et al. (1993) *J. Biolumin. Chemilumin.* 8:301–305].

In general for use herein, the components of the bioluminescence are packaged or provided so that there is insufficient metal ions to trigger the tag reaction. When used, the trace amounts of triggering metal ion, particularly $Ca^{2+}$ is contacted with the other components. For a more sustained glow, aequorin can be continuously reconstituted or can be added or can be provided in high excess.

(2) Luciferin

The aequorin luciferin is coelenterazine and analogs therein, which include molecules having the structure [formula (I)]:

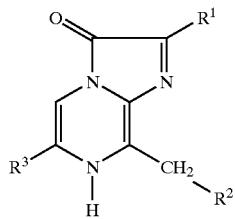

in which $R_1$ is $CH_2C_6H_5$ or $CH_3$; $R_2$ is $C_6H_5$, and $R_3$ is p-$C_6H_4OH$ or $CH_3$ or other such analogs that have activity. Preferred coelenterazine has the structure in which $R^1$ is p-$CH_2C_6H_4OH$, $R_2$ is $C_6H_5$, and $R_3$ is p-$C_6H_4OH$, which can be prepared by known methods [see, e.g., Inouye et al. (1975) *Jap. Chem. Soc., Chemistry Lttrs.* pp 141–144; and Halt et al. (1979) *Biochemistry* 18:2204–2210]. The preferred coelenterazine has the structure (formula (II)):

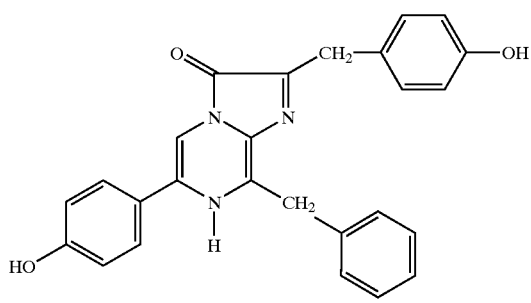

and sulfated derivatives thereof.

The reaction of coelenterazine when bound to the aequorin photoprotein with bound oxygen and in the presence of $Ca^{2+}$ can represented as follows:

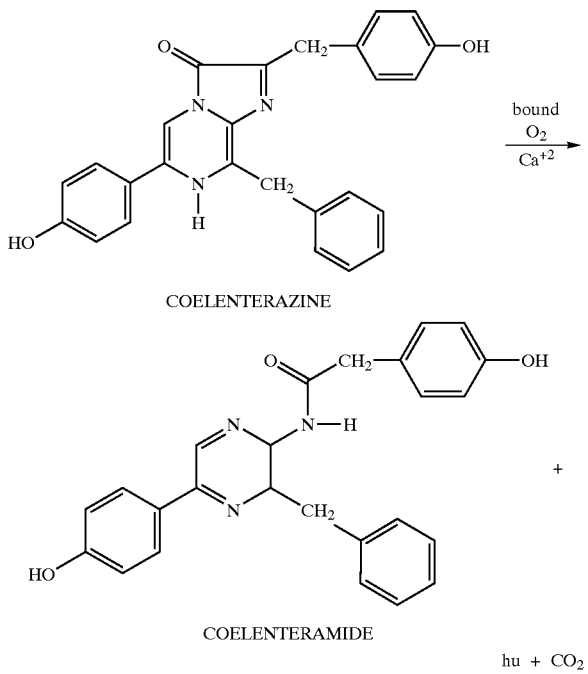

The photoprotein aequorin [which contains apoaequorin bound to a coelenterate luciferin molecule] and Renilla luciferase, discussed below, can use the same coelenterate luciferin. The aequorin photoprotein catalyses the oxidation of coelenterate luciferin [coelenterazine] to oxyluciferin [coelenteramide] with the concomitant production of blue light [lambda$_{max}$=469 nm].

Importantly, the sulfate derivative of the coelenterate luciferin [lauryl-luciferin] is particularly stable in water, and thus may be used in a coelenterate-like bioluminescence generating system. In this system, adenosine diphosphate (ADP) and a sulpha-kinase are used to convert the coelenterazine to the sulphated form. Sulfatase is then used to reconvert the lauryl-luciferin to the native coelenterazine. Thus, the more stable lauryl-luciferin is used in the item to be illuminated and the luciferase combined with the sulfatase are added to the luciferin mixture when illumination is desired.

Thus, the bioluminescence generating system of Aequorea is particularly suitable for use in the methods and apparatus herein. The particular amounts and the manner in which the components are provided depends upon the selected assay, luciferase and anti ligand. This system can be provided in lyophilized form, that will glow upon addition of $Ca^{2+}$. It can be encapsulated, linked to matrices, such as porous glass, or in as a compositions, such as a solution or suspension, preferably in the presence of sufficient chelating agent to prevent triggering the reaction. The concentration of the aequorin photoprotein will vary and can be determined empirically. Typically concentrations of at least 0.1 mg/l, more preferably at least 1 mg/l and higher, will be selected. In certain embodiments, 1–10 mg luciferin/100 mg of luciferase will be used in selected volumes and at the desired concentrations will be used.

b. The Renilla System

Representative of coelenterate systems is the Renilla system. Renilla, also known as sea pansies, are members of the class of coelenterates Anthozoa, which includes other bioluminescent genera, such as Cavarnularia, Ptilosarcus, Stylatula, Acanthoptilum, and Parazoanthus. Bioluminescent members of the Anthozoa genera contain luciferases and luciferins that are similar in structure [see, e.g., Cormier et al. (1973) *J. Cell. Physiol.* 81:291–298; see also Ward et al. (1975) *Proc. Natl. Acad. Sci. U.S.A.* 72:2530–2534]. The luciferases and luciferins from each of these anthozoans crossreact and produce a characteristic blue luminescence.

Renilla luciferase and the other coelenterate and ctenophore luciferases, such as the aequorin photoprotein, use imidazopyrazine substrates, particularly the substrates generically called coelenterazine [see, formulae (I) and (II), above]. Other genera that have luciferases that use a coelenterazine include: squid, such as Chiroteuthis, Eucleoteuthis, Onychoteuthis, Watasenia; cuttlefish, Sepiolina; shrimp, such as Oplophorus, Sergestes, and Gnathophausia; deep-sea fish, such as Argyropelecus, Yarella, Diaphus, and Neoscopelus.

Renilla luciferase does not, however, have bound oxygen, and thus requires dissolved oxygen in order to produce light in the presence of a suitable luciferin substrate. Since Renilla luciferase acts as a true enzyme [i.e., it does not have to be reconstituted for further use] the resulting luminescence can be long-lasting in the presence of saturating levels of luciferin. Also, Renilla luciferase is relatively stable to heat.

Renilla luciferase, DNA encoding Renilla luciferase, and use of the DNA to produce recombinant luciferase, as well as DNA encoding luciferase from other coelenterates, are well known and available [see, e.g., SEQ ID No. 1, U.S. Pat. Nos. 5,418,155 and 5,292,658; see, also, Prasher et al. (1985) *Biochem. Biophys. Res. Commun.* 126:1259–1268; Cormier (1981) "Renilla and Aequorea bioluminescence" in *Bioluminescence and Chemiluminescence,* pp. 225–233; Charbonneau et al. (1979) *J. Biol. Chem.* 254:769–780; Ward et al. (1979) *J. Biol. Chem.* 254:781–788; Lorenz et al. (1981) *Proc. Natl. Acad. Sci. U.S.A.* 88: 4438–4442; Hori et al. (1977) *Proc. Natl. Acad. Sci. U.S.A.* 74:4285–4287; Hori et al. (1975) *Biochemistry* 14:2371–2376; Hori et al. (1977) *Proc. Natl. Acad. Sci. U.S.A.* 74:4285–4287; Inouye et al. (1975) *Jap. Soc. Chem. Lett.*141–144; and Matthews et al. (1979) *Biochemistry* 16:85–91]. The DNA encoding Renilla luciferase and host cells containing such DNA provide a convenient means for producing large quantities of the enzyme [see, e.g, U.S. Pat. Nos. 5,418,155 and 5,292,658, which describe recombinant production of Renilla luciferase and the use of the DNA to isolate DNA encoding other luciferases, particularly those from related organisms]. A modified version of a method [U.S. Pat. Nos. 5,418,155 and 5,292,658] for the recombinant production. of Renilla luciferase that results in a higher level of expression of the recombinant enzyme is presented in the EXAMPLES herein.

When used herein, the Renilla luciferase can be packaged in lyophilized form, encapsulated in a vehicle, either by itself or in combination with the luciferin substrate. Prior to use the mixture is contacted with an aqueous composition, preferably a phosphate buffered saline or other suitable buffer, such a Tris-based buffer [such as 0.1 mm Tris, 0.1 mm EDTA] pH 7–8, preferably about pH 8; dissolved $O_2$ will activate the reaction. Addition of glycerol [about 1%] increases light intensity. Final concentrations of luciferase in the glowing mixture will be on the order of 0.01 to 1 mg/l or more. Concentrations of luciferin will be at least about $10^{-8}$ M, but 1 to 100 or more orders of magnitude higher to produce a long lasting bioluminescence.

In certain embodiments herein, about 1 to 10 mg, or preferably 2–5 mg, more preferably about 3 mg of coelenterazine will be used with about 100 mg of Renilla luciferase. The precise amounts, of course can be determined empirically, and, also will depend to some extent on the ultimate concentration and application. In particular, about addition of about 0.25 ml of a crude extract from the bacteria that express Renilla to 100 ml of a suitable assay buffer and about 0.005 µg was sufficient to produce a visible and lasting glow [see, U.S. Pat. Nos. 5,418,155 and 5,292, 658, which describe recombinant production of Renilla luciferase].

Lyophilized mixtures, and compositions containing the Renilla luciferase are also provided. The luciferase or mixtures of the luciferase and luciferin may also be encapsulated into a suitable delivery vehicle, such as a liposome, glass particle, capillary tube, drug delivery vehicle, gelatin, time release coating or other such vehicle. Kits containing these mixtures, compositions, or vehicles and also a chip device and reagents for attaching biological molecules to the surface of the chip, are also provided. The luciferase may also be linked to an anti ligand through chemical or recombinant means for use in the methods herein.

Recombinant Production of *Renilla Reniformis* Luciferase

The phagemid pTZ18R (Pharmacia) is a multi-purpose DNA vector designed for in vitro transcriptions and useful for expression of recombinant proteins in bacterial hosts. The vector contains the bla gene, which allows for the selection of transformants by resistance to ampicillin, and a polylinker site adjacent to the lacZ' gene. The heterologous gene of interest is inserted in the polylinker and transcribed from the lac promoter by induction, for example, with isopropyl-β-D-thiogalactopyranoside (IPTG).

The DNA encoding the *Renilla reniformis* luciferase has been cloned (e.g., see U.S. Pat. Nos. 5,292,658 and 5,418, 155). The plasmid pTZRLuc-1 encodes the Renilla luciferase on a 2.2 Kbp EcoRI to SstI DNA fragment inserted in EcoRI and SstI sites of pTZ18R (plasmid construction is described U.S. Pat. Nos. 5,292,658 and 5,418, 155; see also Lorenz et al. (1991) *Isolation and Expression of a cDNA encoding Renilla reniformis Luciferase,* Proc. Natl. Acad. Sci. U.S.A. 88, 4438–4442). The initiation of transcription of the Renilla luciferase cDNA is under the control of the lacZ' promoter. *E. coli* strains harboring plasmid pTZRLuc-1 express Renilla luciferase that is functional in bioluminescence assays and retains the properties of the native enzyme (see e.g., U.S. Pat. Nos. 5,292,658 and 5,418,155).

A derivative of pTZRLuc-1, pTZRLuc-3.6, produces approximately 7-fold higher levels of recombinant Renilla luciferase than pTZRLuc-1 when transformed into the same *E. coli* host. Competent *E. coli* strain XL-1 was transformed using purified pTZRLuc-3.6 according to the instructions provided by the manufacturer (XL-1 Supercompetent cells and protocol; Stratagene, Inc., La Jolla, Calif.). Transfectants were selected by plating on Luria Broth (LB) plates supplemented with 100 μg/ml ampicillin.

Single ampicillin resistant colonies were grown in LB medium supplemented with 100 μg/ml ampicillin at ambient temperature using continuous shaking until cell growth reached mid-log phase (i.e., cell culture reaches an $O.D._{600 nm}$=0.6–0.8 units). Transcription from the lac promoter was induced by addition of 1 mM IPTG and cell culture was shaken at ambient temperature for an additional 8 hours.

Cells were harvested by centrifugation at 10,000×g and frozen at −20° C. The cell pellet was thawed and resuspended at a 1:5 ratio (w/w) in a solution of 10 mM EDTA, pH 8.0, containing 4 mg/ml lysozyme (Sigma Chemical Corp.). The cells were placed in a 25° C. water bath for 30 minutes and then transferred to ice for 1 hour. The cells were lysed by sonication at 0° C. using a 1 minute pulse from an Ultrasonics, Inc. cell disruptor.

The lysed cellular debris was removed by centrifugation at 30,000×g for 3 hours and the supernatant was decanted and retained. The pellet was resuspended at a 1:5 ratio in the above-described solutions, and the subsequent incubations, lysis and centrifugation steps were repeated. The two supernatants were combined and stored at −70° C.

The resulting "clarified lysate" was employed as a source of recombinant luciferase. Alternatively, the lysate may be subjected to additional purification steps (e.g., ion exchange chromatography or immunoaffinity chromatography) to further enrich the lysate or provide a homogeneous source of the purified enzyme (see e.g., U.S. Pat. Nos. 5,292,658 and 5,418,155).

3. Crustacean, Particularly Cyrpidina Systems

The ostracods, such as *Vargula serratta, hilgendorfil* and *noctiluca* are small marine crustaceans, sometimes called sea fireflies. These sea fireflies are found in the waters off the coast of Japan and emit light by squirting luciferin and luciferase into the water, where the reaction, which produces a bright blue luminous cloud, occurs. The reaction involves only luciferin, luciferase and molecular oxygen, and, thus, is very suitable for application herein.

The systems, such as the Vargula bioluminescence generating systems, are particularly preferred herein because the components are stable at room temperature if dried and powdered and will continue to react even if contaminated. Further, the bioluminescent reaction requires only the luciferin/luciferase components in concentrations as low as 1:40 parts per billion to 1:100 parts per billion, water and molecular oxygen to proceed. An exhausted system can be renewed by addition of luciferin.

a. Vargula Luciferase

Vargula luciferase is a 555-amino acid polypeptide that has been produced by isolation from Vargula and also using recombinant technology by expressing the DNA in suitable bacterial and mammalian host cells [see, e.g., Thompson et al. (1989) *Proc. Natl. Acad. Sci. U.S.A.* 86:6567–6571; Inouye et al. (1992) *Proc. Natl. Acad. Sci. U.S.A.* 89:9584–9587; Johnson et al. (1978) *Methods in Enzymology* LVII:331–349; Tsuji et al. (1978) *Methods Enzymol.* 57:364–72; Tsuji (19740 *Biochemistry* 13:5204–5209; Japanese Patent Application No. JP 3-30678 Osaka; and European Patent Application No. EP 0 387 355 A1].

(1) Purification from Cypridina

Methods for purification of Vargula [Cypridina] luciferase are well known. For example, crude extracts containing the active can be readily prepared by grinding up or crushing the Vargula shrimp. In other embodiments, a preparation of *Cypridina hilgendorfi* luciferase can be prepared by immersing stored frozen *C. hilgendorfi* in distilled water containing, 0.5–5.0 M salt, preferably 0.5–2.0 M sodium or potassium chloride, ammonium sulfate, at 0–30° C., preferably 0–10° C., for 1–48 hr, preferably 10–24 hr, for extraction followed by hydrophobic chromatography and then ion exchange or affinity chromatography [TORAY IND INC, Japanese patent application JP 4258288, published Sep. 14, 1993; see, also, Tsuji et al. (1978) *Methods Enzymol.* 57:364–72 for other methods].

The luciferin can be isolated from ground dried Vargula by heating the extract, which destroys the luciferase but leaves the luciferin intact [see, e.g, U.S. Pat. No. 4,853,327].

(2) Preparation by Recombinant Methods

The luciferase is preferably produced by expression of cloned DNA encoding the luciferase [European Patent Application NO. 0 387 355 A1; International PCT Application No. WO90/01 542; see, also SEQ ID No. 5, which sets forth the sequence from Japanese Patent Application No. JP 3-30678 and Thompson et al. (1989) *Proc. Natl. Acad. Sci. U.S.A.* 86:6567–6571] DNA encoding the luciferase or variants thereof is introduced into *E. coli* using appropriate vectors and isolated using standard methods.

b. Vargula Luciferin

The natural luciferin in a substituted imidazopyrazine nucleus, such a compound of formula (III):

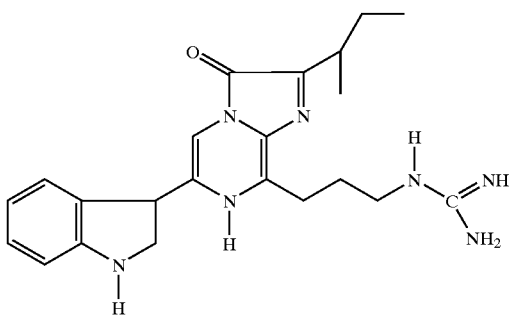

Analogs thereof and other compounds that react with the luciferase in a light producing reaction also may be used.

Other bioluminescent organisms that have luciferases that can react with the Vargula luciferin include, the genera Apogon, Parapriacanthus and Porichthys.

c. Reaction

The luciferin upon reaction with oxygen forms a dioxetanone intermediate [which includes a cyclic peroxide similar to the firefly cyclic peroxide molecule intermediate]. In the final step of the bioluminescent reaction, the peroxide breaks down to form $CO_2$ and an excited carbonyl. The excited molecule then emits a blue to blue-green light.

The optimum pH for the reaction is about 7. For purposes herein, any pH at which the reaction occurs may be used. The concentrations of reagents are those normally used for analytical reactions or higher [see, e.g., Thompson et al. (1990) *Gene* 96:257–262]. Typically concentrations of the luciferase between 0.1 and 10 mg/l, preferably 0.5 to 2.5 mg/l will be used. Similar concentrations or higher concentrations of the luciferin may be used.

4. Insect Bioluminescence Generating Systems Including Firefly, Click Beetle, and Other Insect Systems The biochemistry of firefly bioluminescence was the first bioluminescence generating system to be characterized [see, e.g., Wienhausen et al. (1985) *Photochemistry and Photobiology* 42:609–611; McElroy et al. (1 966) in *Molecular Architecture in Cell Physiology,* Hayashi et al., eds. Prentice Hall, Inc., Englewood Cliffs, N.J., pp. 63–80] and it is commercially available [e.g., from Promega Corporation, Madison, Wis., see, e.., Leach et al. (1986) *Methods in Enzymology* 133:51–70, esp. Table 1]. Luciferases from different species of fireflies are antigenically similar. These species include members of the genera Photinus, Photurins and Luciola. Further, the bioluminescent reaction produces more light at 30° C. than at 20° C., the luciferase is stabilized by small quantities of bovine albumin serum, and the reaction can be buffered by tricine.

a. Luciferase

DNA clones encoding luciferases from various insects and the use to produce the encoded luciferase is well known. For example, DNA clones that encode luciferase from *Photinus pyralis, Luciola cruciata* [see, e.g., de Wet et al. (1985) *Proc. Natl. Acad. Sci. U.S.A.* 82:7870–7873; de We et al. (1986) *Methods in Enzymology* 133:3; U.S. Pat. No. 4,968,613, see, also SEQ ID No. 3] are available. The DNA has also been expressed in Saccharomyces [see, e.g., Japanese Application No. JP 63317079, published Dec. 26, 1988, KIKKOMAN CORP] and in tobacco.

In addition to the wild-type luciferase modified insect luciferases have been prepared. For example, heat stable luciferase mutants, DNA-encoding the mutants, vectors and transformed cells for producing the luciferases are available. A protein with 60% amino acid sequence homology with luciferases from *Photinus pyralis, Luciola mingrelica, L. cruciata* or *L. lateralis* and having luciferase activity is available [see, e.g., International PCT Application No. WO95/25798]. It is more stable above 30° C. than naturally-occurring insect luciferases and may also be produced at 37° C. or above, with higher yield.

Modified luciferases that generate light at different wavelengths [compared with native luciferase], and thus, may be selected for their color-producing characteristics. For example, synthetic mutant beetle luciferase(s) and DNA encoding such luciferases that produce bioluminescence at a wavelength different from wild-type luciferase are known [Promega Corp, International PCT Application No. WO95/18853, which is based on U.S. application Ser. No. 08/177, 081 Jan. 3, 1994]. The mutant beetle luciferase has an amino acid sequence differing from that of the corresponding wild-type Luciola cruciata [see, e.g, U.S. Pat. Nos. 5,182, 202, 5,219,737, 5,352,598, see, also SEQ ID No.3] by a substitution(s) at one or two positions. The mutant luciferase produces a bioluminescence with a wavelength of peak intensity that differs by at least 1 nm from that produced by wild-type luciferases.

Other mutant luciferase have also been produced. Mutant luciferases with the amino acid sequence of wild-type luciferase, but with at least one mutation in which valine is replaced by isoleucine at the amino acid number 233, valine by isoleucine at 239, serine by asparagine at 286, glycine by serine at 326, histidine by tyrosine at 433 or proline by serine at 452 are known [see, e., U.S. Pat. Nos. 5,219,737, and 5,330,906]. The luciferases are produced by expressing DNA-encoding each mutant luciferase in *E. coli* and isolating the protein. These luciferases produce light with colors that differ from wild-type. The mutant luciferases catalyze luciferin to produce red [λ609 nm and 612 nm], orange [λ595 and 607 nm] or green [λ558 nm] light. The other physical and chemical properties of mutant luciferase are substantially identical to native wild type-luciferase. The mutant luciferase has the amino acid sequence of Luciola cruciata luciferase with an alteration selected from Ser 286 replaced by Asn, Gly 326 replaced by Ser, His 433 replaced by Tyr or Pro 452 replaced by Ser. Thermostable luciferases are also available [see, e.g, U.S. Pat. No. 5,229,285; see, also International PCT Application No.@ 95/25798, which provides Photinus luciferase in which the glutamate at position 354 is replaced lysine and Luciola luciferase in which the glutamate at 356 is replaced with lysine].

These mutant luciferases as well as the wild type luciferases are among those preferred herein, particularly in instances when a variety of colors are desired or when stability at higher temperatures is desired. It is also noteworthy that firefly luciferases have alkaline pH optima [7.5–9.5], and, thus, are suitable for use in diagnostic assays performed at alkaline pH.

b. Luciferin

The firefly luciferin is a benzothiazole:

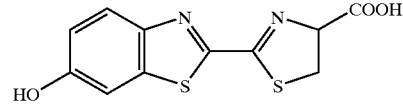

Analogs of this luciferin and synthetic firefly luciferins are also known to those of skill in art [see, e.g., U.S. Pat. No. 5,374,534 and 5,098,8281. These include compounds of formula (IV) [see, U.S. Pat. No. 5,098,828]:

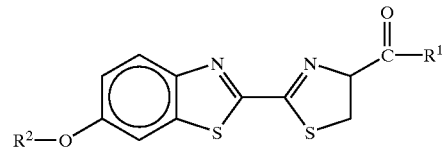

in which:

$R^1$ is hydroxy, amino, linear or branched $C_1$–$C_{20}$ alkoxy, $C_2$–$C_{20}$ alkyenyloxy, an L-amino acid radical bond via the α-amino group, an oligopeptide radical with up to ten L-amino acid units linked via the α-amino group of the terminal unit;

$R^2$ is hydrogen, $H_2PO_3$, $HSO_3$, unsubstituted or phenyl substituted linear or branched $C_1$–$C_{20}$ alkyl or $C_2$–$C_{20}$alkenyl, aryl containing 6 to 18 carbon atoms, or $R^3$—C(O)—; and $R^3$ is an unsubstituted or phenyl substituted linear or branched $C_1$–$C_{20}$ alkyl or $C_2$–$C_{20}$alkenyl, aryl containing 6 to 18 carbon atoms, a nucleotide radical with 1 to 3 phosphate groups, or a glycosidically attached mono- or disaccharide, except when formula (IV) is a D-luciferin or D-luciferin methyl ester.

c. Reaction

The reaction catalyzed by firefly luciferases and related insect luciferases requires ATP, $Mg^{2+}$ as well as molecular oxygen. Luciferin must be added exogenously. Firefly luciferase catalyzes the firefly luciferin activation and the subsequent steps leading to the excited product. The luciferin reacts with ATP to form a luciferyl adenylate intermediate. This intermediate then reacts with oxygen to form a cyclic luciferyl peroxy species, similar to that of the coelenterate intermediate cyclic peroxide, which breaks down to yield $CO_2$ and an excited state of the carbonyl product. The excited molecule then emits a yellow light; the color, however, is a function of pH. As the pH is lowered the color of the bioluminescence changes from yellow-green to red.

Different species of fireflies emit different colors of bioluminescence so that the color of the reaction will be dependent upon the species from which the luciferase is obtained. Additionally, the reaction is optimized at pH 7.8.

Addition of ATP and luciferin to a reaction that is exhausted produces additional light emission. Thus, the system, once established, is relatively easily maintained. Therefore, it is highly suitable for use herein in embodiments in which a sustained glow is desired or reuse of the item is contemplated. Thus, the components of a firefly system can be packaged with the chip.

5. Bacterial Systems

Luminous bacteria typically emit a continuous light, usually blue-green. When strongly expressed, a single bacterium may emit $10^4$ to $10^5$ photons per second. Bacterial bioluminescence systems include, among others, those systems found in the bioluminescent species of the genera Photobacterium, Vibrio and Xenorhabdus. These systems are well known and well characterized [see, e.g., Baldwin et al. (1984) *Biochemistry* 23:3663–3667; Nicoli et al. (1974) *J. Biol. Chem.* 249:2393–2396; Welches et al. (1981) *Biochemistry* 20:512–517; Engebrecht et al. (1986) *Methods in Enzymology* 133:83–99; Frackman et al. (1990) *J. of Bacteriology* 172:5767–5773; Miyamoto et al. (1986) *Methods in Enzymology* 133:70; U.S. Pat. No. 4,581,335].

a. Luciferases

Bacterial luciferase, as exemplified by luciferase derived from *Vibrio harveyi* [EC 1. 14.14.3, alkanol reduced-FMN-oxygen oxidoreductase 1-hydroxylating, luminescing], is a mixed function oxidase, formed by the association of two different protein subunits α and β. The α-subunit has an apparent molecular weight of approximately 42,000 kD and the β-subunit has an apparent molecular weight of approximately 37,000 kD [see, e.g., Cohn et al. (1989) *Proc. Natl. Acad. Sci. U.S.A.* 90:102–123]. These subunits associate to form a 2-chain complex luciferase enzyme, which catalyzes the light emitting reaction of bioluminescent bacteria, such as *Vibrio harveyi* [U.S. Pat. No. 4,581,335; Belas et al. (1982) *Science* 218:791–793], *Vibrio fischeri* [Engebrecht et al. (1983) *Cell* 32:773–781; Engebrecht et al. (1984) *Proc. Natl. Acad. Sci. U.S.A.* 81:4154–4158] and other marine bacteria.

Bacterial luciferase genes have been cloned [see, e.g., U.S. Pat. No. 5,221,623; U.S. Pat. No. 4,581,335; European Patent Application No. EP 386 691 A]. Plasmids for expression of bacterial luciferase, such as *Vibrio harveyi*, include pFIT001 (NRRL B-18080), pPALE001 (NRRL B-18082) and pMR19 (NRRL B-18081)] are known. For example the sequence of the entire lux regulon from *Vibiro fisheri* has been determined [Baldwin et al. (1984), *Biochemistry* 23:3663–3667; Baldwin et al. (1981) *Biochem.* 20: 512–517; Baldwin et al. (1984) *Biochem.* 233663–3667; see, also, e.g, U.S. Pat. Nos. 5,196,318, 5,221,623, and 4,581, 335]. This regulon includes luxI gene, which encodes a protein required for autoinducer synthesis [see, e.g., Engebrecht et al. (1984) *Proc. Natl. Acad. Sci. U.S.A.* 81:4154–4158], the luxC, luxD, and luxE genes, which encode enzymes that provide the luciferase with an aldehyde substrate, and the luxA and luxB genes, which encode the alpha and beta subunits of the luciferase.

Lux genes from other bacteria have also been cloned and are available [see, e.g., Cohn et al. (1985) *J. Biol. Chem.* 260:6139–6146; U.S. Pat. No. 5,196,524, which provides a fusion of the luxA and luxB genes from *Vibrio harveyi*]. Thus, luciferase alpha and beta subunit-encoding DNA is provided and can be used to produce the luciferase. DNA encoding the α[1065 bp] and β[984 bp] subunits, DNA encoding a luciferase gene of 2124 bp, encoding the alpha and beta subunits, a recombinant vector containing DNA encoding both subunits and a transformed *E. coli* and other bacterial hosts for expression and production of the encoded luciferase are available. In addition, bacterial luciferases are commercially available.

b. Luciferins

Bacterial luciferins include:

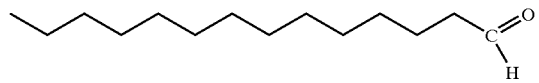

or

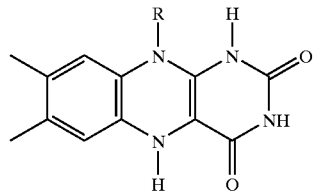

R is, for example, 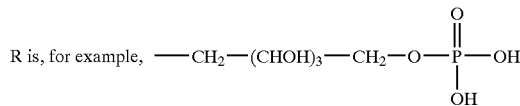

in which the tetradecanal with reduced flavin mononucleotide are considered luciferin since both are oxidized during the light emitting reaction.

c. Reactions

The bacterial systems require, in addition to reduced flavin, five polypeptides to complete the bioluminescent reaction: two subunits, α and β, of bacterial luciferin and three units of a fatty acid reductase system complex, which supplies the tetradecanal aldehyde. Examples of bacterial bioluminescence generating systems useful in the apparatus and methods provided herein include those derived from *Vibrio fisheri* and *Vibrio harveyi*. One advantage to this system is its ability to operate at cold temperatures. It will thus be particularly amenable to methods of using the chip for the detection and monitoring of antibiotic sensitivity of psychrophilic organisms. All components of a bacterial system can be frozen into ice or placed in solutions stored below 0° C. After incubation at temperatures near 0° C., the chip can be transferred to warmer temperatures and the reaction will proceed thereby providing a sustained glow.

Bacterial luciferase catalyzes the flavin-mediated hydroxylation of a long-chain aldehyde to yield carboxylic acid and an excited flavin; the flavin decays to ground state with the concomitant emission of blue green light [$\lambda_{max}$=490 nm; see, e.g., Legocki et al. (1986) *Proc. Natl. Acad. Sci. USA* 81:9080; see U.S. Pat. No. 5,196,524]:

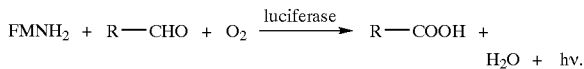

The reaction can be initiated by contacting reduced flavin mononucleotide [FMNH$_2$] with a mixture of the bacterial luciferase, oxygen, and a long-chain aldehyde, usually n-decyl aldehyde.

DNA encoding luciferase from the fluorescent bacterium *Alteromonas hanedai* is known [CHISSO CORP; see, also, Japanese application JP 7222590, published Aug. 22, 1995]. The reduced flavin mononucleotide [FMNH$_2$; luciferin] reacts with oxygen in the presence of bacterial luciferase to produce an intermediate peroxy flavin. This intermediate reacts with a long-chain aldehyde [tetradecanal] to form the acid and the luciferase-bound hydroxy flavin in its excited state. The excited luciferase-bound hydroxy flavin then emits light and dissociates from the luciferase as the oxidized flavin mononucleotide [FMN] and water. In vivo FMN is reduced again and recycled, and the aldehyde is regenerated from the acid.

Flavin reductases have been cloned [see, e.g., U.S. Pat. No. 5,484,723; see, SEQ ID No. 14 for a representative sequence from this patent]. These as well as NAD(P)H can be included in the reaction to regenerate FMNH$_2$ for reaction with the bacterial luciferase and long chain aldehyde. The flavin reductase catalyzes the reaction of FMN, which is the luciferase reaction, into FMNH2; thus, if luciferase and the reductase are included in the reaction system, it is possible to maintain the bioluminescent reaction. Namely, since the bacterial luciferase turns over many times, bioluminescence continues as long as a long chain aldehyde is present in the reaction system.

The color of light produced by bioluminescent bacteria also results from the participation of a blue-florescent protein [BFP] in the bioluminescence reaction. This protein, which is well known [see, e.g., Lee et al. (1978) *Methods in Enzymology LVII*:226–234], may also be added to bacterial bioluminescence reactions in order to cause a shift in the color.

6. Other Systems a. Dinoflagellate Bioluminescence Generating Systems

In dinoflagellates, bioluminescence occurs in organelles termed scintillons. These organelles are outpocketings of the cytoplasm into the cell vacuole. The scintillons contain only dinoflagellate luciferase and luciferin [with its binding protein], other cytoplasmic components being somehow excluded. The dinoflagellate luciferin is a tetrapyrrole related to chlorophyll:

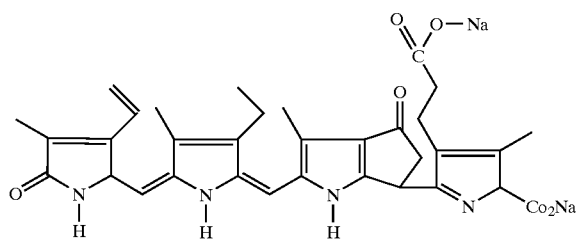

or an analog thereof.

The luciferase is a 135 kD single chain protein that is active at pH 6.5, but inactive at pH 8[see, e.g, Hastings (1981) *Bioluminescence and Chemiluminescence*, DeLuca et al., eds. Academic Press, NY, pp.343–360]. Luminescent activity can be obtained in extracts made at pH 8 by shifting the pH from 8 to 6. This occurs in soluble and particulate fractions. Within the intact scintillon, the luminescent flash occurs for ~100 msec, which is the duration of the flash in vivo. In solution, the kinetics are dependent on dilution, as in any enzymatic reaction. At pH 8, the luciferin is bound to a protein [luciferin binding protein] that prevents reaction of the luciferin with the luciferase. At pH 6, however, the luciferin is released and free to react with the enzyme.

b. Systems from Molluscs, such as Latia and Pholas

Molluscs *Latia neritoides* and species of Pholas are bioluminescent animals. The luciferin has the structure:

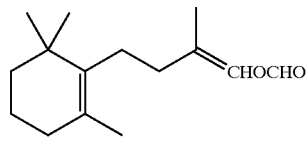

and has been synthesized [see, e.g., Shimomura et al. (1968) *Biochemistry* 7:1734–1738; Shimomura et al. (1972) *Proc. Natl. Acad. Sci. U.S.A.* 69:2086–2089]. In addition to a luciferase and luciferin the reaction has a third component, a "purple protein". The reaction, which can be initiated by an exogenous reducing agent is represented by the following scheme:

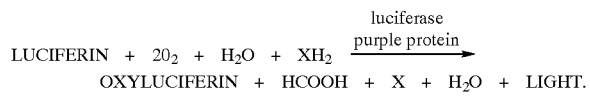

XH$_2$ is a reducing agent.

Thus for practice herein, the reaction will require the purple protein as well as a reducing agent.

c. Earthworms and other Annelids

Earthworm species, such as *Diplocardia Ionga*, Chaetopterus and Harmothoe, exhibit bioluminescence. The luciferin has the structure:

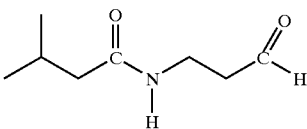

The reaction requires hydrogen peroxide in addition to luciferin and luciferase. The luciferase is a photoprotein.

d. Glow Worms

The luciferase/luciferin system from the glow worms that are found in New Zealand caves, Australia and those found in Great Britain are also intended for use herein.

e. Marine Polycheate Worm Systems

Marine polycheate worm bioluminescence generating systems, such as Phyxotrix and Chaetopterus, are also contemplated for use herein.

f. South American Railway Beetle

The bioluminescence generating system from the South American railway beetle is also intended for use herein.

9. Fish

Of interest herein, are luciferases and bioluminescence generating systems that generate red light. These include luciferases found in species of Aristostomias, such as *A. scintillans*[see, e.g.,O'Day et al. (1974) *Vision Res.* 14:545–550], Pachystomias, Malacosteus, such as *M. niger*.

7. Fluorescent Proteins
a. Green and Blue Fluorescent Proteins

As described herein, blue light is produced using the Renilla luciferase or the Aequorea photoprotein in the presence of $Ca^{2+}$ and the coelenterazine luciferin or analog thereof. This light can be converted into a green light if a green fluorescent protein (GFP) is added to the reaction. Green fluorescent proteins, which have been purified [see, e.g., Prasher et al. (1992) *Gene* 111:229–233] and also cloned [see, e.g., International PCT Application No. WO 95/07463, which is based on U.S. application Ser. No. 08/119,678 and U.S. application Ser. No. 08/192,274, which are herein incorporated by reference], are used by cnidarians as energy-transfer acceptors. GFPs fluoresce in vivo upon receiving energy from a luciferase-oxyluciferein excited-state complex or a $Ca^{2+}$-activated photoprotein. The chromophore is modified amino acid residues within the polypeptide. The best characterized GFPs are those of Aequorea and Renilla [see, e.g., Prasher et al. (1992) *Gene* 111 :229–233; Hart, et al. (1979)*Biochemistry* 18:2204–2210]. For example, a green fluorescent protein [GFP] from Aequorea Victoria contains 238 amino acids, absorbs blue light and emits green light. Thus, inclusion of this protein in a composition containing the aequorin photoprotein charged with coelenterazine and oxygen, can, in the presence of calcium, result in the production of green light. Thus, it is contemplated that GFPs may be included in the bioluminescence generating reactions that employ the aequorin or Renilla luciferases or other suitable luciferase in order to enhance or alter color of the resulting bioluminescence.

GFPs are activated by blue light to emit green light and thus may be used in the absence of luciferase and in conjunction with an external light source with novelty items, as described herein. Similarly, blue fluorescent proteins (BFPs), such as from *Vibrio fischeri, Vibrio harveyi* or *Photobacterium phosphoreum,* may be used in conjunction with an external light source of appropriate wavelength to generate blue light. (See for example, Karatani, et al., "A blue fluorescent protein from a yellow-emitting luminous bacterium," *Photochem. Photobiol.* 55(2):293–299 (1992); Lee, et al., "Purification of a blue-fluorescent protein from the bioluminescent bacterium *Photobacterium phosphoreum" Methods Enzymol.* (Biolumin. Chemilumin.) 57:226–234 (1978); and Gast, et al. "Separation of a blue fluorescence protein from bacterial luciferase" *Biochem. Biophys. Res. Commun.* 80(1):14–21 (1978), each, as all references cited herein, incorporated in its entirety by reference herein.) In particular, GFPs, and/or BFPs or other such fluorescent proteins may be used in the methods provided herein for the detection of infectious agents by binding an analyte to one or more anti ligand-GFP conjugate (s) at a plurality of locations and illuminating the chip with light of an appropriate wavelength to cause the fluorescent proteins to fluoresce whereby the emitted fluorescence is detected by the photodiodoes in the chip.

GFPs and/or BFPs or other such fluorescent proteins may be used in conjunction with any of the chips or devices described herein. These fluorescent proteins may also be used alone or in combination with bioluminescence generating systems to produce an array of colors. They may be used in combinations such that the color, for example, of the emitted light may be altered to maximize the amount of light available for detection by the photodiodes of the chip.

b. Phycobiliproteins

Phycobiliproteins are water soluble fluorescent proteins derived from cyanobacteria and eukaryotic algae [see, e.g., Apt et al. (1995) *J. Mol. Biol.* 238:79–96; Glazer (1982) *Ann. Rev. Microbiol.* 36:173–198; and Fairchild et al. (1994) *J. of Biol. Chem.* 269:8686–8694]. These proteins have been used as fluroescent labels in immmunoassay [see, Kronick (1986) *J. of Immunolog. Meth.* 92:1–13], the proteins have been isolated and DNA encoding them is also available [see, e.g., Pilot et al. (1984) *Proc. Natl. Acad. Sci. U.S.A.* 81:6983–6987; Lui et al. (1993) *Plant Physiol* 103:293–294; and Houmard et al. (1988) *J. Bacteriol.* 170:5512–5521; the proteins are commercially available from, for example, ProZyme, Inc., San Leandro, Calif.].

In these organisms, the phycobiliproteins are arranged in subcellular structures termed phycobilisomes and function as accessory pigments that participate in photosynthetic reactions by absorbing visible light and transferring the derived energy to chlorophyll via a direct fluorescence energy transfer mechanism.

Two classes of phycobiliproteins are known based on their color: phycoerythrins (red) and phycocyanins (blue), which have reported absorbtion maxima between 490 and 570 nm and between 610 and 665 nm, respectively. Phycoerythrins and phycocyanins are heterogenous complexes composed of different ratios of alpha and beta monomers to which one or more class of linear tetrapyrrole chromophores are covalently bound. Particular phycobiliproteins may also contain a third γ-subunit which often associated with $(\alpha,\beta)_6$ aggregate proteins.

All phycobiliproteins contain phycothrombilin or phycoerythobilin chromophores, and may also contain other bilins, such as phycourobilin, cryptoviolin or a 697 nm bilin. The γ-subunit is covalently bound with phycourobilin, which results in the 495–500 nm absorbance peak of B- and R-phycoerythrins. Thus, the spectral characteristics of phycobiliproetins may be influenced by the combination of the different chromophores, the subunit composition of the apo-phycobiliproteins and/or the local environment that affects the tertiary and quaternary structure of the phycobiliproteins.

As described above for GFPs & BFPs, phycobiliproteins are also activated by visible light of the appropriate wavelength and thus may be used in the absence of luciferase and in conjunction with an external light source to illuminate the phycobiliprotein bound to the chip at locations where analyte has been detected. In particular, phycobiliproteins may be covalently bound to one or more anti-ligand specific for the targeted analyte and illuminated with light of an appropriate wavelength to cause the fluorescent proteins to fluoresce and the fluorescence is measured by the photodiodes of the chip at that location of the array. The data signals are sent to the computer processor and analyzed. As noted above, these proteins may be used in combination with other fluoresent proteins and/or bioluminescence generating systems to produce an array of colors or to provide different colors over time that can be detected by the photodiodes of the chip.

Attachment of phycobiliproteins to solid support matrices is known (e.g., see U.S. Pat. Nos. 4,714,682; 4,767,206; 4,774,189 and 4,867,908). Therefore, phycobiliproteins may be coupled to microcarriers coupled to one or more components of the bioluminescent reaction, preferably a luciferase, to convert the wavelength of the light generated from the bioluminescent reaction. Microcarriers coupled to one or more phycobiliproteins may be used when linked to the anti-ligand or to any of the chips used in the methods herein.

c. Design, Fabrication, and use of Chips

Chips for use as diagnostic devices are provided herein. The chips can be nonself-addressable or self-addressable and are typically in the form of an array, such as a 96-member or higher density array or any of those described herein.

1. Nonself-addressable Chips

Referring to FIG. 1, a nonself-addressable microelectronic device 100 for detecting and identifying analytes in a biological sample using bioluminescence includes an address control circuit 102, a photodetector array 104, an analog multiplexer 106, a comparator 108, a reference circuit 110, a feedback control circuit 112 and an output control circuit 114. Address control circuit 102 receives a clock input signal 116 from an external oscillator, and output control circuit 114 generates data output signals 118. Device 100 also includes electrical connections 120 and 122 for receiving electrical power and ground, respectively, from an external power source (e.g., an AC-DC converter). Thus, device 100 requires only four electrical connections: clock input signal 116; data output signals 118; power 120; and ground 122.

Address control circuit 102 receives clock input signal 116 and generates address signals on busses 124–128 in response thereto which sequentially address each pixel element within array 104. Each pixel element has a row and a column address that are used to address the pixel. Address control circuit 102 sequentially addresses each row of pixel elements within array 104 using row address signals asserted on bus 124. For each row, address control circuit 102 generates address signals on bus 126 that are used as select signals by analog multiplexer 106, and also generates address signals on bus 128 that are used by feedback control circuit 112 to generate feedback signals for the pixel elements as described below. Address control circuit 102 generates binary address signals decoded into individual row and column address enable signals by one or more address decode circuits located in address control circuit 102, array 104, multiplexer 106 and/or feedback control circuit 112. The addressing of an array in electronic circuits is well known to those of ordinary skill in the art.

Array 104 receives row address signals 124 from address control circuit 102 and feedback signals 130 from feedback control circuit 112. Each element in array 104 includes a photodetector that receives photons of light from a chemical reaction optically coupled to the photodetector. Based on these inputs, array 104 generates analog column output signals 132 that are applied to analog multiplexer 106. Array 104 uses row address signals 124 to address each row of pixel elements, uses feedback signals 130 when performing a delta-sigma analog-to-digital (A/D) conversion on each pixel element as described below, and generates column output signals 132 that are also used in the delta-sigma A/D conversion.

Analog multiplexer 106 uses address signals 126 to multiplex column output signals 132 into multiplexed analog output signals 134. Comparator 108 compares multiplexed output signals 134 to a reference signal 136 (e.g., a reference current) generated by reference circuit 110 and, based upon the results of the comparison, generates quantized output signals 138. Quantized output signals 138 and address signals 128 are used by feedback control circuit 112 to generate feedback signals 130 that are applied to array 104 as described below. Quantized output signals 138, that are indicative of the photons of light detected at each element in array 104, are also used by output control circuit 114 to generate data output signals 118.

In one embodiment, output control circuit 114 formats quantized output signals 138 into an RS-232 serial data stream indicative of the light detected at each pixel element in array 104. To allow an external instrument or computer to correlate the received RS-232 serial data stream with specific pixel elements in array 104, output control circuit 114 transmits the serial data stream in frames separated by a synchronization signal (sync). Each frame contains an output data signal for each pixel element in array 104, and the sync signal is an arbitrary value (e.g., a byte having a value of decimal 255) used as a control signal to identify the start of each data frame. The external computer waits for the sync signal before correlating the received frame data to the appropriate pixel elements in array 104. Alternatively, output control circuit 114 could include labels in the serial data stream that identify the pixel elements. A parallel data interface can also be used.

As will become apparent from the description below, array 104 includes pixel elements located at an array of micro-locations on the surface of the semiconductor substrate used for device 100. Each element includes a photodetector for receiving photons of light emitted by a chemical reaction optically coupled at the respective micro-location and for converting the received photons into an electric charge. Each element also includes a pixel unit cell circuit with a capacitance circuit for integrating the electric charge. The integrated charge is quantized using delta-sigma A/D conversion techniques, and the digitized signal is multiplexed into a serial data output stream interfaced to an external computer. The computer executes a control program to integrate the delta-sigma digital signal for a desired integration period ranging from seconds to hours depending on the desired resolution. In one embodiment, the delta-sigma A/D conversion is clocked for a 56 Kbaud interface to achieve 12-bit resolution in an integration period of about 10 seconds, and 16-bit resolution in a time period of about 3 minutes.

Figure 2:
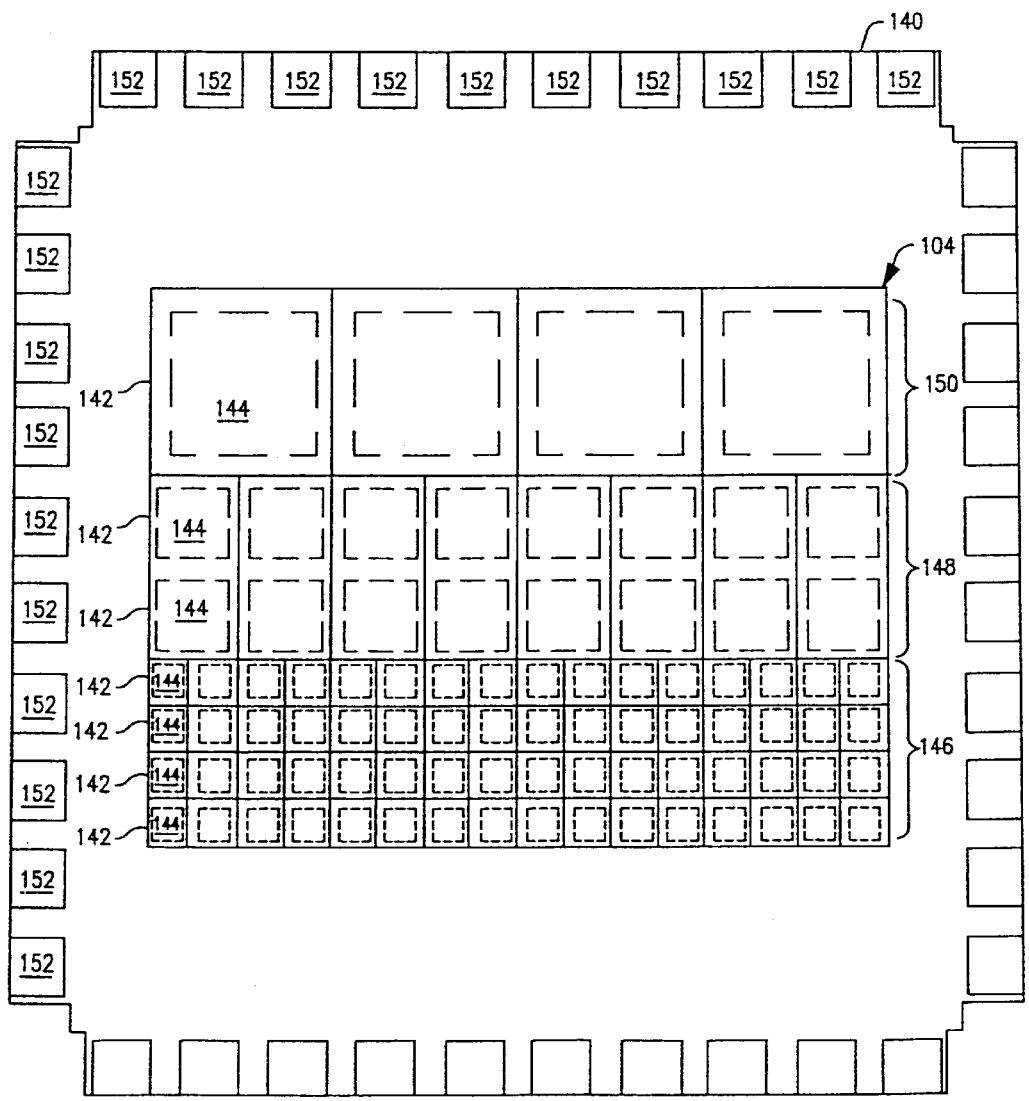
FIG. 2 is a top view of the die for the microelectronic device of FIG. 1 showing the photodetector array disposed on a semiconductor substrate.

Referring to FIG. 2, device 100. includes a semiconductor substrate or die 140 having array 104 defined on a surface thereof. Array 104 includes an array of micro-locations 142, and an independent photodetector 144 optically coupled to each micro-location. (Only the left-most micro-location 142 and photodetector 144 in each row are labeled in FIG. 2 for clarity.) Array 104 includes three sub-arrays 146, 148 and 150 having three different sizes of micro-locations 142. Sub-array 146 includes a 4×16 array of 50 micron square pixels, sub-array 148 includes a 2×8 array of 100 micron square pixels, and sub-array 150 includes a 1×4 array of 200 micron square pixels. Photodetectors 144 are located on a portion of the surface of die 140 at each micro-location 142. The portion taken up by photodetector 144 includes about 90% of the surface area for larger pixel elements and about 50% for smaller pixel elements. In one embodiment, photodetectors 144 are silicon photodiodes that convert photons of light impinging on their surfaces into a photocurrent. The quantum efficiency of this conversion is about 40% at a wavelength of 500–800 nm (i.e., a photocurrent of 40 electrons is generated for each 100 photons of received light). Photodiodes 144 can thus convert low photon levels into measurable signals. The surface of substrate 140 has a slight depression (eq., 1 micron) at each micro-location 142 to help contain the fluid sample applied to device 100.

Figure 3:
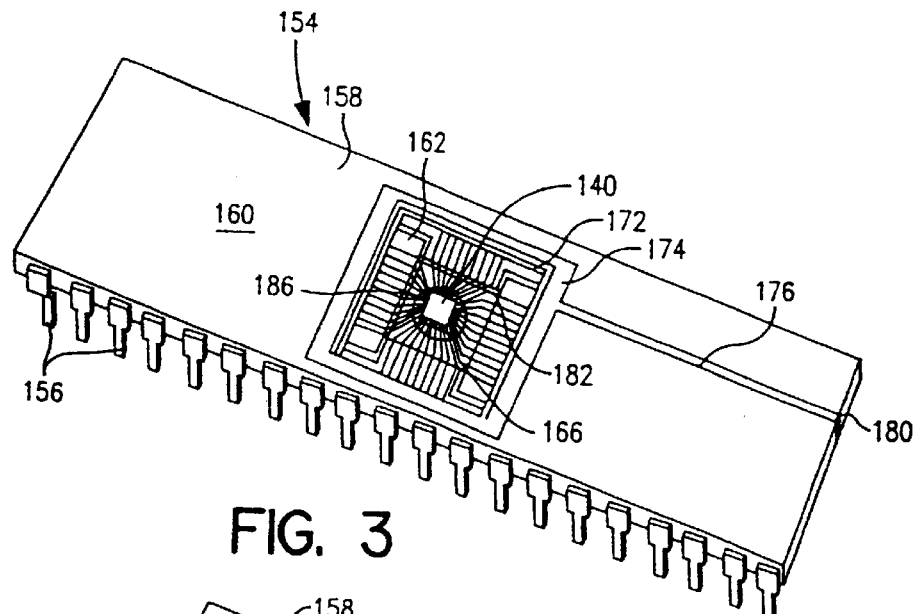
FIG. 3 is a perspective view of the microelectronic device of FIG. 1 including the die of FIG. 2 housed in a ceramic dual in-line package (DIP)

Array 104 is formed on a relatively small die 140 (e.g., 2.4×2.4 mm) to allow for low-cost production of device 100. Die 140 also has the electronic circuitry of device 100 formed thereon (not shown in FIG. 2), and the outer perimeter of die 140 includes bonding pads 152 that connect to the electronic circuitry via traces formed on the die. Pads 152 are bonded by wire bonds or other conductors to external leads or conductors of the microelectronic package for die 140 as shown in FIG. 3. Pads 152 include pads for clock input signal 116, data output signal 118, electrical power 120, ground 122, and various test signals as desired. In one embodiment, microelectronic device 100 is an integrated circuit device fabricated using a standard CMOS process well known to those of skill in the art.

The larger pixels elements (e.g., 200 um) in array 104 have a higher sensitivity to detect lower concentrations of analytes than the smaller pixel elements (e.g., 50 um) since a greater number of receptor antibodies can be bound to their larger surface areas, as explained herein, such that more photons of light will be emitted when a chemical reaction occurs at the respective micro-location. The smaller pixels can be used to form a larger matrix on a given die size to allow a greater number of assays to be performed simultaneously. The optimum pixel size for detecting a particular analyte may be determined empirically. The use of different-sized pixel elements on device 100 has two advantages. First, larger pixel elements can be used to detect analytes requiring larger sensitivities while smaller pixel elements can be used to increase the number of pixel elements in the matrix for analytes having lower sensitivities. Second, different sizes can be used to help determine the optimum size for a particular analyte by empirical testing, with the optimum-size being used for other embodiments of array 104.

Alternative arrangements of array 104 will be apparent to a person of ordinary skill in the art. For example, array 104 can include sub-arrays of pixel elements having different sizes (as in FIG. 2), or an array having only a single pixel size (e.g., a 12×16 array of 50 micron pixels). The size of each pixel (e.g., 50, 100, 200 microns in FIG. 2) can be modified (e.g., a 400 micron pixel can be used). Also, the number of pixels in the array or sub-array (e.g., 4×16, 2×8 or 1×16 in FIG. 2) can be changed to include an n×m array or sub-array having n rows and m columns, n and m being integers. Further, shapes other than squares can be used for each pixel element (e.g., rectangles or circles). The size of die 140 can be modified to accommodate the different arrangements of array 104, although use of a larger die may increase the cost of device 100. Also, die 140 may include more or fewer bonding pads 152, provided there are separate pads for clock input signal 116, data output signals 118, electrical power 120 and ground 122 (FIG. 1).

Figure 3A:
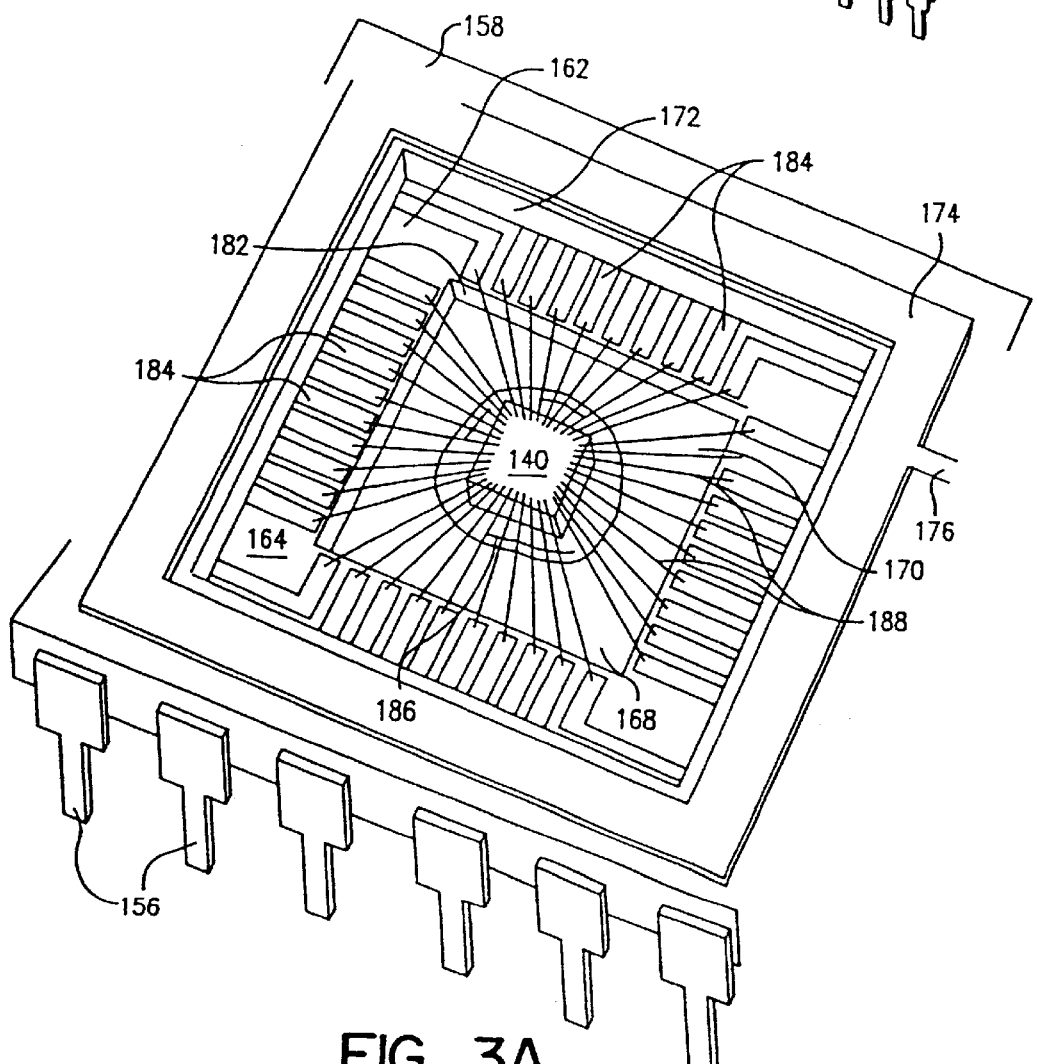
FIG. 3A is a magnified view showing the test well formed in the DIP in detail.

Referring to FIGS. 3 and 3A, die 140 is packaged within a ceramic dual in-line package (DIP) 154 with 40 pins or leads 156. Four pins 156 are dedicated to clock input signal 116, data output signals 118, electrical power 120, and ground 122. The other pins 156 are used for test signals. Other microelectronic packages may also be used, such as plastic packages having more or fewer conductors including the four required conductors.

Package 154 has a top layer 158 having an upper surface 160, a middle layer 162 having an upper surface 164, and a lower layer 166 having an upper surface 168. Layers 158 and 162 are made of a non-conductive dielectric (e.g. ceramic) and lower layer 166 forms a conductive ground plane 170 electrically coupled to the ground pin 156 of package 154. Upper surface 160 of top layer 158 has a first square aperture 172 formed therein. A ground conductor trace 174 formed on upper surface 160 surrounds aperture 172 and is electrically coupled to ground by a ground trace 176 also formed on upper surface 160 that passes through a cut 180 formed in the outer perimeter of package 154, and attaches to ground plane 170. Aperture 172 reveals a square portion of middle layer 162 having a second square aperture 182 formed therein. The dimensions of second aperture 182 are smaller than the dimensions of first aperture 172 such that a portion of upper surface 164 of middle layer 162 is visible from the top of package 154. The visible portion of upper surface 164 has conductive pads 184 formed thereon that electrically connect to pins 156 of package 154 via traces (only partially shown) passing between layers 158 and 162. Aperture 182 reveals a square portion of ground plane 170 that has die 140 attached thereto by a suitable adhesive 186. Each bonding pad 152 of die 140 is electrically connected to one conductive pad 184 by a bond wire 188.

Bond wires 188 are coated with a material (.e.g., epoxy) impervious to the fluid sample to be analyzed. The other conductive components of package 154, except for pins 156, may also be coated with the material to prevent direct contact with the fluid sample. Pins 156 of package 154 are not coated by the material such that pins 156 will make electrical contact with an external computer or instrument when package 154 is read thereby.

When performing an assay, the fluid sample to be analyzed is applied through apertures 172 and 182 to the surface of die 140 (and micro-locations 142 formed thereon) housed within package 154. The fluid sample may be applied by pipetting the fluid sample into the test well formed by apertures 172 and 182, or simply by dipping package 154 into a container (now shown) filled with the sample. The electrical components of device 100 are protected from the sample by the materials of package 154 itself, or by the epoxy coating. After the fluid sample is applied, the remaining components needed to cause light-emitting reactions optically coupled to micro-locations 142 are also applied to the surface of die 140 through apertures 172 and 182. The resulting light-emitting reactions are then detected by photodetectors 144 as described below in relation to FIG. 4.

Figure 4:
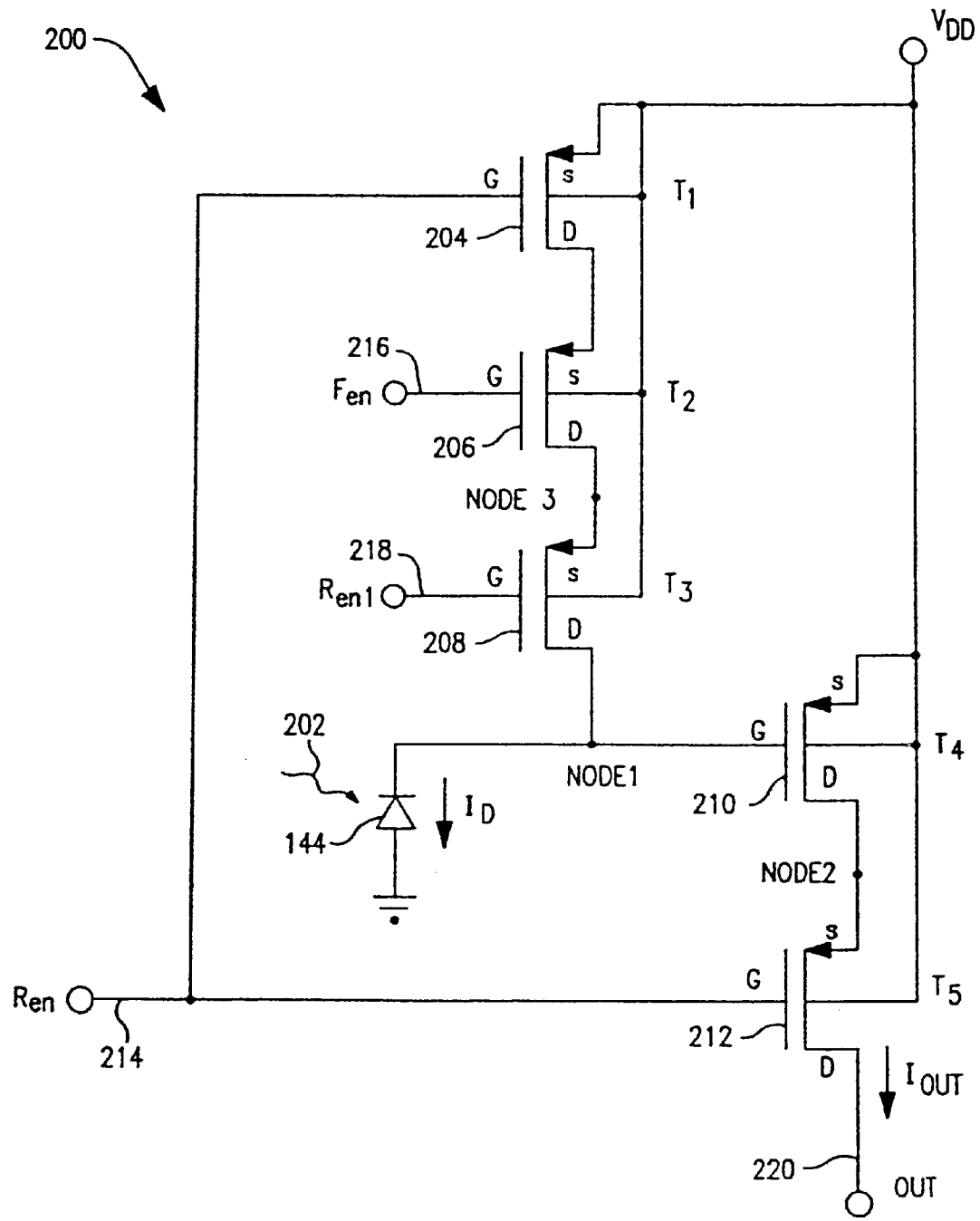
FIG. 4 is a schematic diagram showing a pixel unit cell circuit for detecting the bioluminescence emitted at each micro-location in the array.

Referring to FIG. 4, the photodetector 144 of each pixel element in array 104 includes a pixel unit cell circuit 200 associated therewith. Each photodetector 144 is preferably a photodiode that generates sensed signals (i.e., photocurrents) in response to photons of light 202 impinging on its surface. Each pixel unit cell circuit 200 integrates this sensed signal and quantizes the integrated signal using delta-sigma A/D conversion techniques. Circuit 200 includes five MOSFET transistors $T_1$–$T_5$ designated by numerals 204–212, each having a gate terminal G, a source terminal S (with an arrow pointing in toward the oxide layer), a drain terminal D, and a base terminal (unlabeled). Transistor T1 has its gate G connected to a row enable input signal Ren designated 214, its source S connected to power supply voltage $V_{DD}$ and its drain D connected to source S of $T_2$. Transistor $T_2$ has its gate G connected to a feedback enable signal Fen designated 216, its source S connected to drain D of $T_1$, and its drain D connected to source S of $T_3$ at Node 3. Transistor $T_3$ has its gate G connected to a next row enabled signal $R_{en1}$ designated 218, its source S connected to Node 3, and its drain D connected to gate G of $T_4$ at Node 1. The cathode of photodiode 144 is also connected to Node 1, and its anode is connected to ground. Transistor $T_4$ has its gate G connected to Node 1, its source S connected to $V_{DD}$, and its drain D connected to source S of $T_5$, at Node 2. Transistor $T_5$ has its gate G connected to $R_{en}$ (214), its source S connected to Node 2, and its drain D connected to output terminal 220. The base of each transistor $T_1$–$T_5$ is connected to $V_{DD}$. Transistor $T_2$ uses a second layer of polysilicon for its gate G to allow for a slightly smaller spacing between transistors, while transistors $T_1$ and $T_3$–$T_5$ use only a first layer of polysilicon.

The current flowing through photodiode 144, designated $I_D$, includes two components. The first component is a leakage current flowing through photodiode 144, that has a constant value. The second component is the current flow caused by photons 202 impinging on photodiode 144 due to the light-emitting chemical reaction, if any, optically coupled to the respective micro-location 142, taking into account the photodiode's quantum efficiency. Current $I_D$ discharges Node 1 toward ground at a rate depending on the leakage current and the number of photons impinging on photodiode 144. Node 1 will be discharged relatively quickly when a large amount of light is received, and relatively slowly when little or no light is present. Even when no light is present, Node 1 is still discharged due to the leakage component of $I_D$. The photocurrent component of $I_D$ can be separated from the leakage current component by taking dark readings when the light-emitting reactions are not occurring, taking test readings when the reactions are taking place, and correcting the test readings using the dark readings (e.g., by subtracting the dark readings from the test readings). The dark readings may be taken either before, after, or both before and after, the actual test takes place.

Referring back to FIG. 1 for a moment, the output currents flowing from output terminal 220, designated $I_{OUT}$, are the column output signals 132 that are multiplexed by analog multiplexer 106 to form multiplexed output signals 134 input to comparator 108. Comparator 108 maintains $I_{OUT}$ at a constant voltage since the sensed signal is a current, and generates quantized output signals 138 based upon comparisons between signals 134 and reference current 136. Feedback control circuit 112 generates feedback signals 130, that form enable signals $F_{en}$ (216), based upon quantized output signals 138 and address signals 128. $F_{en}$ for each pixel element is generated during the time period when the next pixel element is being addressed. When address control circuit 102 addresses the next row of pixel elements, causing $R_{en}$ (214) to be asserted for that row, the next row enabled signal $R_{en1}$ (218) is also asserted for the previous row of pixel elements using address decode circuits as are well known in the art.

Returning to FIG. 4, pixel unit cell circuit 200 operates as follows. Photons 202 impinging on photodiode 144 generate current $I_D$ that discharges Node 1 at a rate depending on the number of photons of light received, the photodiode's quantum efficiency, and the constant leakage current. When this pixel element is addressed by address control circuit 102 (i.e., $R_{en}$ activated), transistors $T_1$ and $T_5$ are enabled (i.e., become conductive). With $T_5$ conducting, and output terminal 220 held at a constant voltage less than $V_{DD}$ by comparator 108, transistor $T_4$ produces a current proportional to the difference between $V_{DD}-V_T$ and the voltage at Node 1. $V_T$ is the transistor threshold voltage (e.g., about 1 V). This current flows through transistor $T_5$ as $I_{OUT}$. After passing through multiplexer 106, $I_{OUT}$ is compared to reference current 136 by comparator 108, which includes a differential current amplifier. Quantized output signal 138 is reset to 0 by comparator 108 when $I_{OUT}$ is less than reference current 136 and is set to 1 when $I_{OUT}$ is greater than reference current 136.

When $I_{OUT}$ is less than reference current 136 (i.e., quantized output signal 138=0), feedback control circuit 112 disables feedback signal 130 (i.e., $F_{en}=0$) to keep transistor $T_2$ in a non-conducting state. Thus, the voltage at Node 3 is not affected and $I_D$ continues to discharge Node 1. When $I_{OUT}$ exceeds reference current 136 (i.e., quantized output signal 138=1), feedback control circuit 112 enables feedback signal 130 (i.e., $F_{en}=1$) to turn on $T_2$ while $T_1$ is still enabled by $R_{en}$. This sets the capacitance (i.e., the inherent source and drain to bulk capacitance of the MOSFET transistors) at Node 3 to $V_{DD}$. There will be no appreciable voltage drop across $T_1$ or $T_2$ since these transistors are turned on into their linear regions and no current is flowing. When the next row is addressed (causing $R_{en1}$ to be set to 1), the charge on the capacitance circuit is transferred to Node 1 to raise the voltage at Node 1. Thus, the capacitance circuit is reset to an initial charge whenever $I_{OUT}$ transitions above reference current 136. This charge transfer is standard in switched capacitor circuits, and is well known to those of skill in the art. Since $I_D$ discharges the capacitance for a period of time before the discharge of Node 1 is sufficient to trip comparator 108, the capacitance effectively integrates $I_D$ flowing through photodiode 144.

After being reset to its initial value, the capacitance at Node 1 is again discharged by photodiode 144 at a rate dependent on the magnitude of $I_D$ until $I_{OUT}$ again transitions above reference current 136, at which time Node 1 is again recharged. Thus, Node 1 is kept at a voltage near the voltage value required for $T_4$ to produce reference current 136. The number of times that comparator 108 senses reference current 136 exceeded (i.e., "comparator positive transitions") is proportional to the total charge that has flowed through photodiode 144. As stated previously, $I_D$ is the sum of the constant leakage current and the current due to sensed photons 202. Thus, the number of comparator positive transitions over a period of time can be used to acc-emitting reaction, after the number is adjusted for the leakage current flowing through photodiode 144 by subtracting the dark readings. Quantized output signals 138, as stated above, are formatted into an RS-232 serial data stream transmitted to an external computer as data output signals 118.

Figure 5:
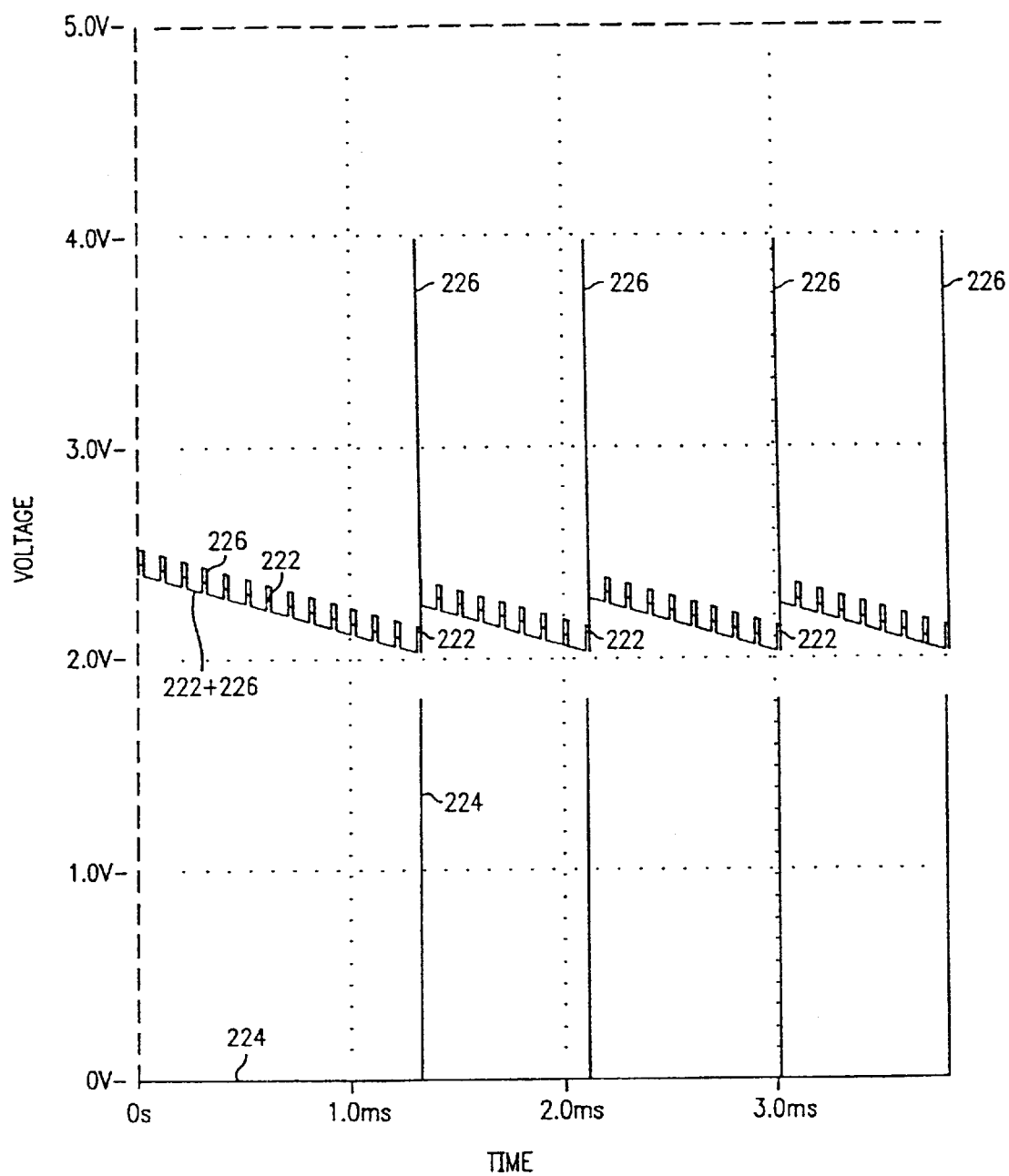
FIG. 5 is a graph showing the voltage levels at three nodes of the pixel unit cell circuit of FIG. 4 as a function of time during operation of the device.

Referring to FIG. 5, the voltages at Nodes 1, 2 and 3 during operation of device 100 are shown. The voltages at Nodes 1, 2 and 3 are designated by curves 222, 224 and 226, respectively. The x-axis represents time (msec), and the y-axis represents voltage (V). Voltages at nodes 1 and 3 are essentially equal during most of the downward sloping portions of curves 222 and 226, differing as shown in FIG. 5. At the start of each cycle (i.e., at each comparator positive transition occurring at each large spike in voltage at Node 3), the voltage at Node 1 is recharged to its initial value when Node 3 is set to $V_{DD}$. Then, Node 1 is discharged by $I_D$ at a rate depending on the amount of light detected by photodiode 144. A steep decreasing slope on curve 222 occurs when photodiode 144 receives a relatively large amount of light, while a gradually decreasing slope occurs when photodiode 144 receives relatively little or no light. Current $I_{OUT}$ caused by the difference between $V_{DD}-V_T$ and the voltage at Node 1 is compared to reference current 136 whenever the pixel is addressed (approximately every 0.1 msec). When $I_{OUT}$ is less than reference current 136, circuit 200 integrates the sensed signal from photodiode 144 by continuing to discharge Node 1, and the voltage at Node 1 decreases as shown by curve 222. When $I_{OUT}$ exceeds reference current 136, $F_{en}$ causes the capacitance at Node 3 to be reset to $V_{DD}$. Then, when the next row is addressed (i.e., causing $R_{en1}$ to be set), the charge on this capacitance circuit is transferred to Node 1, thereby raising the voltage at Node 1. The cycle repeats throughout the integration time period. The external computer counts the number of comparator positive transitions that occur during the integration time period using data output signal 118. After integration is complete, the computer corrects for the leakage current using the dark readings. The corrected number of counts is proportional to the concentration of the analyte in the fluid sample.

Figure 6:
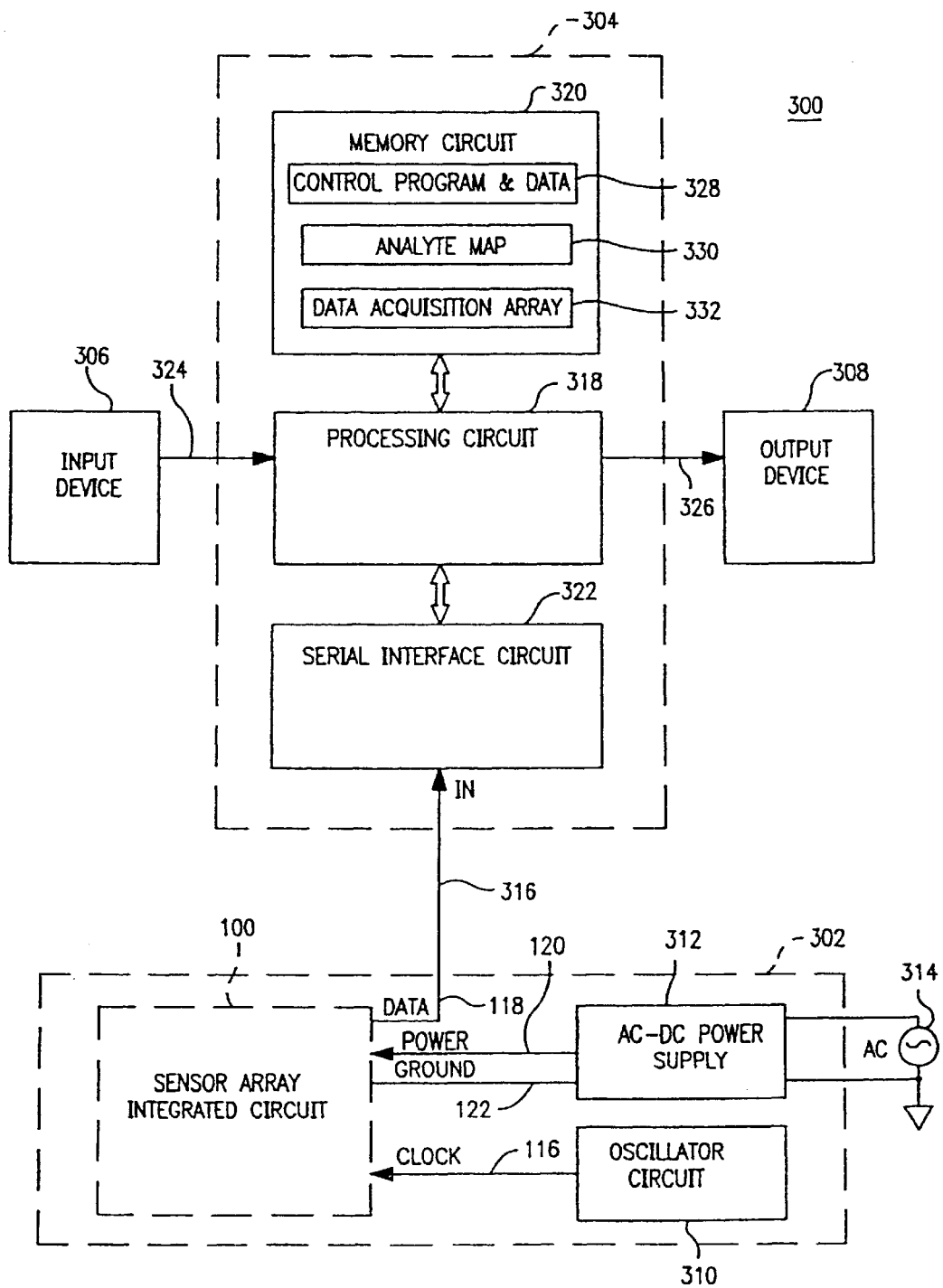
FIG. 6 is a system block diagram showing the microelectronics device of FIG. 1 mounted on an adaptor circuit board and serially interfaced to a computer programmed to read the serial output data stream, to correlate the output data with the array of micro-locations, to integrate the data correlated with each micro-location for a predetermined time period set using an input device, to identify the analytes present in the biological medium by reference to an analyte map, and to display the results on an output device.

Referring to FIG. 6, a system 300 for detecting and identifying analytes in a fluid sample using light-emitting reactions includes an adaptor circuit board 302, a computer 304, an input device 306, and an output device 308. System 300 forms a test instrument. Board includes a zero-insertion force (ZIF) socket (not shown) for receiving device 100, housed in package 154, after it has been dipped into the fluid sample to be analyzed and then exposed to the remaining components of the light-emitting chemical reactions. Board 302 also includes an oscillator circuit 310 for generating clock input signal 116, and an AC-DC power supply 312 for receiving AC power from an external AC power supply 314 and for generating DC electrical power signal 120 therefrom. An RS-232 serial data cable 316 carries serial data output signals 118 from board 302 to computer 304.

Computer 304 includes a processing circuit 318, a memory circuit 320, and a serial interface circuit 322. Processing circuit 318 includes a central processing unit such as a microprocessor or microcontroller that receives input signals 324 from input device 306 and transmits output signals 326 to output device 308 via I/O interface circuits (not shown). Memory circuit 320 includes three memory areas 328–332 including volatile and non-volatile memory. Memory area 328 stores the control program executed by processing circuit 318 and the fixed and variable data (e.g., calibration and empirical testing data) needed during execution. Optional memory area 330 stores an analyte map used by processing circuit 318 to identify the particular analyte being tested for at each micro-location 142 in array 104. When the map is present, processing circuit 318 may be programmed to identify analytes detected in the fluid sample by correlating the received data output signals 118 to the analytes identified in the map, and to generate output signals 326 to identify the detected analytes on output device 308. Memory area 332 stores a data acquisition array used by processing circuit 318 to accumulate the comparator positive transitions for each pixel element during the integration time period. The number of comparator positive transitions received during this period is indicative of the amount of light received by the photodetector 144 at each pixel element.

Input device 306 includes, for example, a keyboard, a mouse, a touch screen, or another input device for generating input signals 324 used to control operation of system 300. Input signals 324 from device 306 allow the user to, for example, start and stop operation of system 300, input analyte map data, input a desired integration time period, and input any other data or commands needed by processing circuit 318 to detect and identify analytes in the fluid sample being analyzed. Input signals 324 may also be used to configure computer 304 to read a particular device 100 having a predetermined arrangement of array 104. Output device 308 may include electronic display for displaying the presence and/or concentration of analytes in the fluid sample being analyzed in response to output signals 326. Output device 308 may also include a printer for displaying such data.

In one embodiment, the user enters a desired integration time period into computer 304 using input device 306 before starting a test. For example, the user may input a period of 10 seconds for 12-bit resolution, or 3 minutes for 16-bit resolution. The user then applies the fluid sample to be analyzed to device 100 (e.g., by dunking package 154 into a container holding the sample), adds the remaining components of the light-emitting reaction, and inserts package 154 into the ZIF socket on board 302. Device 100 will then start to transmit frames of data over cable 316 to computer 304. Each frame includes the quantized delta-sigma A/D conversion data for each pixel element in array 104. Processing circuit 318 waits for the sync byte to determine the start of a data frame. Once a frame starts, processing circuit 318 correlates the data received in each frame with micro-locations 142 in array 104 (based upon the known arrangement of array 104), and integrates the output data signals 118 correlated with each micro-location 142 by accumulating the comparator positive transitions in the respective locations in data acquisition array 332. The transitions are accumulated for the duration of the desired integration time period. After the integration period is complete, processing circuit 318 corrects the integrated data to correct for the leakage current through photodetectors 144 based upon dark readings previously taken (e.g., by inserting package 154 into board 302 before starting the light-emitting reactions). At this point, the corrected data in each location of array 332 is related to the presence of the analytes in the fluid sample being tested for. Processing circuit 318 then generates output signals 326 that, when applied to output device 308, causes output device 308 to display the corrected data. This corrected data is related to the presence and/or concentration of each analyte being tested for by relationships determined empirically using known concentrations of analytes.

In another embodiment, the optional analyte map has been pre-programmed in memory area 330 with the identities of-the analytes being tested for at each micro-location 142 in array 104 before the test is started (possibly by using input device 306). Then, instead of simply outputting the corrected data for display on output device 308, processing circuit 318 performs the additional step of correlating the locations in data acquisition array 332 with the analyte map to identify the analytes, and generates output signals 326 to identify that analytes the corrected data represents.

In yet another embodiment, the data stored in memory area 328 includes threshold data indicative of the presence of each analyte in the fluid sample being analyzed. The threshold data for each analyte may have been determined by empirical testing using a fluid sample having a known minimum concentration of the analyte, or may simply be stored as an offset from the dark readings. Processing circuit 318 then compares the corrected data to the threshold data (or the uncorrected data to the dark readings when offsets are used) to determine which analytes are present in the fluid sample being analyzed. Output signals 326 are then generated so that the analytes present in the fluid sample are displayed or printed. This embodiment may also include the use of the analyte map to allow processing circuit 318 to identify the analytes whose presence in the sample fluid is detected.

In still another embodiment, the data within memory area 328 includes empirically-determined equations, curves or tables representing relationships between the corrected data and the concentrations of the analytes being tested for. Methods for determining such equations, curves or tables are well known in the art, and can include computer curve-fitting techniques. Processing circuit 318 uses the corrected data as input data for the equations, curves or tables to determine the concentration of each analyte in the sample. Output signals 326 are generated so that the concentration of analytes present in the sample are displayed or printed. This embodiment may again include the analyte map to allow processing circuit 318 to identify the analytes whose concentration in the sample fluid was determined.

Figure 7:
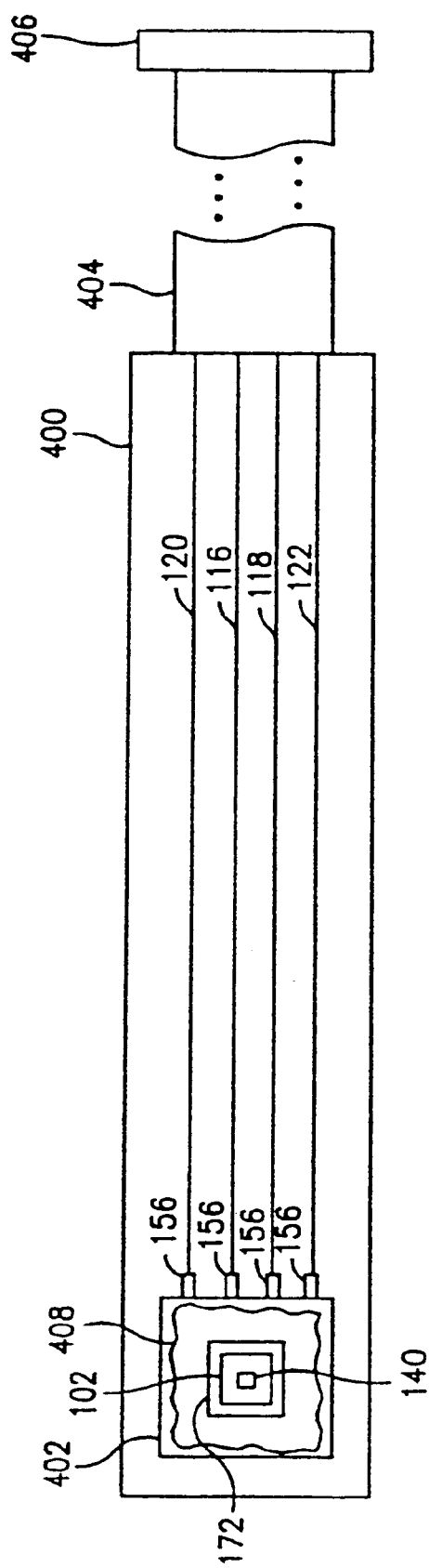
FIG. 7 shows the microelectronics device of FIG. 1 received on a circuit board which does not require the user to directly handle the package.

System 300 provides a kit useful for evaluating device 100. This system requires the user to directly handle package 154, which may result in mechanical damage to pins 156 or electrostatic discharge damage to circuit 100. To avoid the need for direct handling by the user, device 100 may be mounted on a disposable test circuit board 400 as shown in FIG. 7. Device 100 may again be packaged in ceramic DIP package 154, or may alternatively be packaged in another style of microelectronic package 402 (e.g., a leadless chip carrier) mounted on board 400. Varieties of microelectronic packages are well known in the art. Package 402 is adhered (e.g., soldered) to board 400 such that the user only needs to handle board 400, and does not need to handle package 402 directly.

Package 402 includes leads or pins 156 that are electrically coupled to traces 116–122 formed on board 400 for the clock input signal, data output signal, power and ground, respectively. Package 402 may have only these four pins to reduce cost in high-volume applications. Traces 116–122 are electrically coupled to a cable 404 that attaches to a connector 406, which attaches to a mating connector on the test instrument or computer. The conductors of package 402, traces 116–122 and the surface of board 400 are protected from the fluid sample to be analyzed with an epoxy coating 408. Coating 408 is not applied over apertures 172 and 182 or die 140 to allow the fluid sample and the remaining components of the light-emitting reactions to be applied to device 100.

Alternatively, multi-well chips are composed of three layers [see, e.g., FIGS. 8–11]. The bottom layer forms the lower section of each well and incorporates a semiconductor layer, a photodiode at the bottom of each well and an anode electrode, i.e., metal wire surrounding each well. The middle layer fits into grooves in the bottom layer and is composed of a reflective metal layer, an insulating layer, preferably derivatized plastic or silicon, such as MYLAR (oriented polyethylene terephthalate is commercially available from the E.I. du Pont de Nemours & Co., Inc.) to which the specific antibody or ligand for each well is attached [e.g., antibodies attached to MYLAR; see FIG. 10]. The top cap layer forms the remaining upper portion of each well and also contains the cathode electrode. Analytes or reactants may be transported within or among wells by free field electrophoresis by supplying direct current, or by reversing the polarity of the current, through the upper cathode and lower anode [e.g., see FIG. 11].

Figure 20:
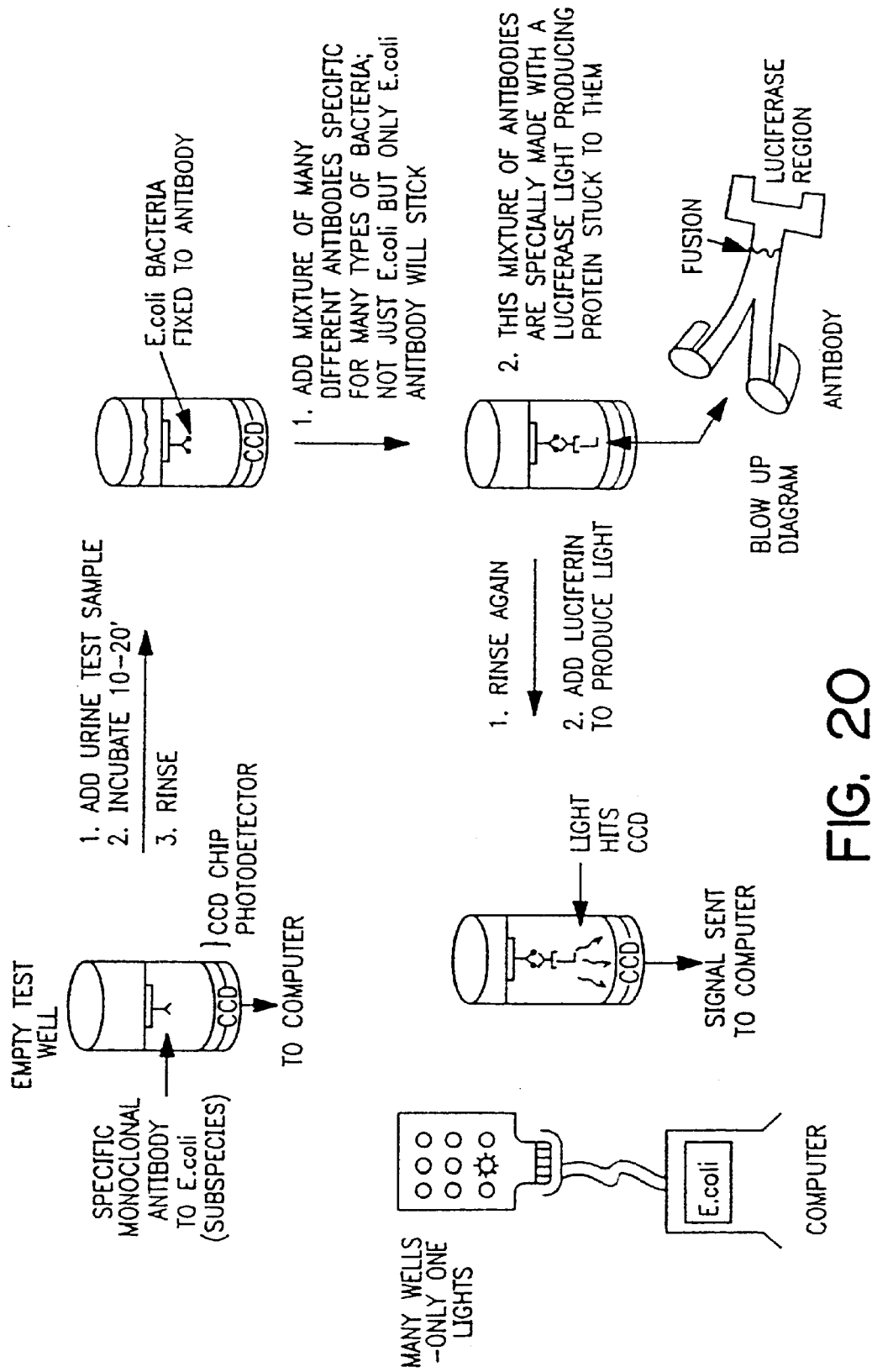
FIG. 20 depicts a scheme for operation of chips described herein in diagnostic assays for detecting infectious microorganisms.

When-used, the chip is contacted with a sample and washed thoroughly. Buffer or other suitable compositions is added to each well, until the level is above the cathode position. The chip is then contacted with a composition containing a luciferin or, preferably a luciferase, conjugated or fused or otherwise linked to an antibody or antibody binding portion thereof or a plurality of such fusions. The antibodies or portions thereof are each specific for the antigens of interest. The remaining components of the bioluminescence generating system are added and the chip is attached to a power source through a wire harness [see, e.g., see FIG. 11, bottom]. Light produced is contained within each well and is detected by the photodiode located at the bottom of each well. The reflective surface will enhance the signal. The detected signal is relayed to a computer processing unit essentially as described above and the computer identifies the detected well and then displays the specific infectious agent detected on an accompanying monitor or printout [see, e.g., FIG. 20].

2. Self Addressable Chips

The self-addressable chips [see, e.g., FIGS. 12–16] include a matrix, an insulating a layer, a metal layer to which an attachment layer and a permeation layer are affixed. The chip also includes photodiodes that will detect emitted light.

a. Matrix Materials

Any matrix or chip may be employed as a substrate for fabricating the devices provided herein. The substrate may be biological, nonbiological, organic, inorganic, or a combination of any of these, existing as particles, strands, precipitates, gels, sheets, tubing, spheres, containers, capillaries, pads, slices, films, plates, slides, etc. The substrate may have any convenient shape, such as a disc, square, sphere, and a circle. The substrate and its surface preferably form a rigid support on which to carry out the reactions described herein. The substrate and its surface should also be chosen to provide appropriate light-absorbing characteristics. For instance, the substrate may be a polymerized Langmuir Blodgett film, functionalized glass, Si, Ge, GaAs, GaP, $SiO_2$, $SiN_4$, modified silicon, or any one of a wide variety of polymers such as (poly)tetrafluoroethylene, (poly)vinylidenedifluoride, or combinations thereof. Other substrate materials will be readily apparent to those of skill in the art in light of the disclsoure herein. Presently preferred are silica substrates used in the fabrication of microelectric chip devices.

b. Fabrication Procedures i. Microlithography

International patent application Publication Nos. WO 95/12808 and WO 96/07917 describe general microlithographic or photolithographic techniques that can be used for the fabrication of the complex "chip" type device that has a large number of small micro-locations. While the fabrication of devices does not require complex photolithography, the selection of materials and the requirement that an electronic device function actively in aqueous solutions does not require special considerations.

Figure 14:
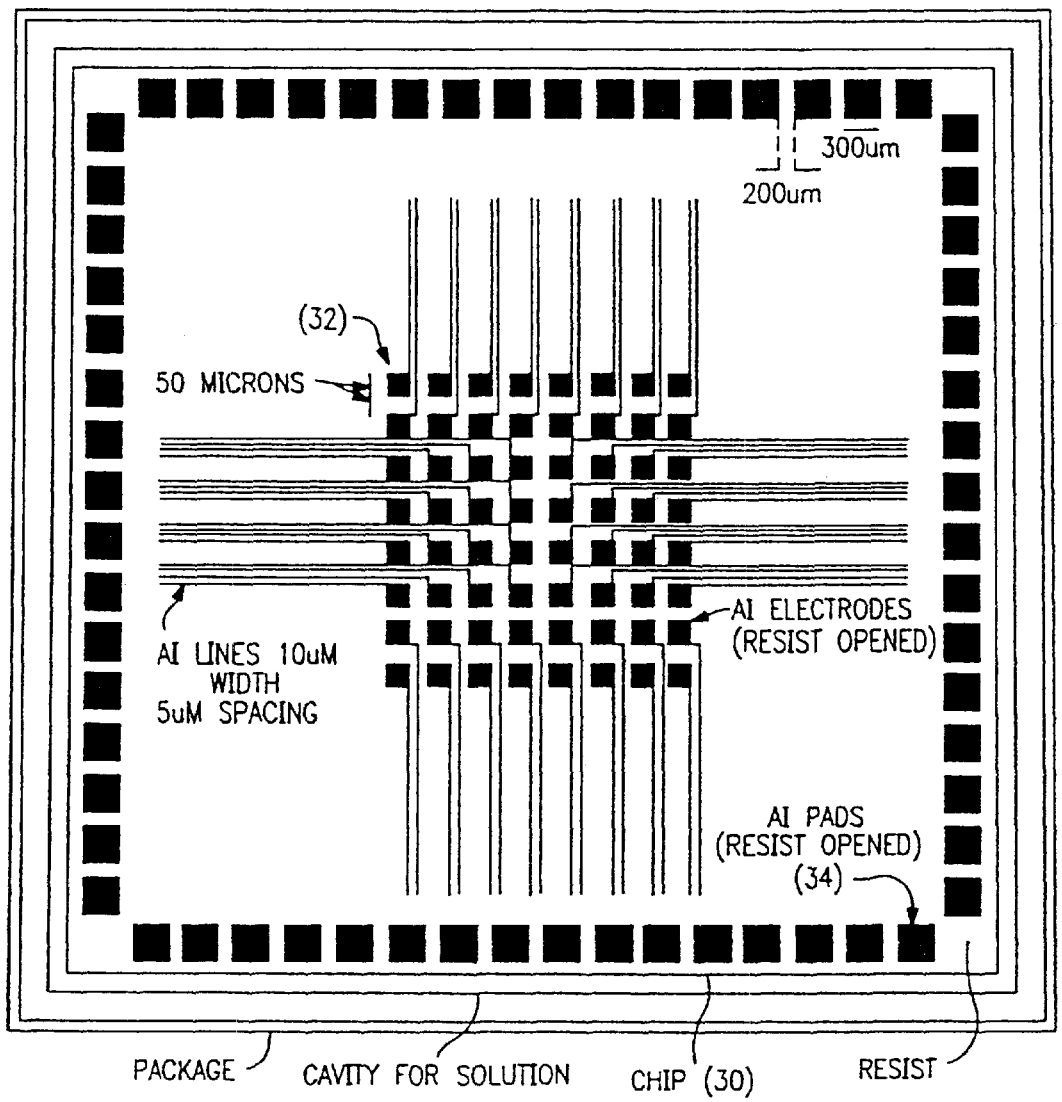
FIG. 14 is a schematic representation of a self-addressable 64 micro-location chip which was actually fabricated, addressed with oligonucleotides, and tested.

The 64 micro-location device shown in FIG. 14 of WO 95/12808 that can be fabricated using relatively simple mask design and standard microlithographic techniques. Generally, the base substrate material would be a 1 to 2 centimeter square silicon wafer or a chip approximately 0.5 millimeter in thickness. The silicon chip is first overcoated with a 1 to 2 $\mu$m thick silicon dioxide ($SiO_2$) insulation coat, which is applied by plasma enhanced chemical vapor deposition (PECVD).

The chips are preferably designed to contain detector elements, e.g., photodiodes, that are incorporated into the semicondutor layer and coupled through optical paths, such as by waveguides or other means, to the other optical paths of the chip. In preferred embodiments, the detector element is comprised of a linear array of photodiodes with an approximate resolution of 1–5 microns, preferably 1–2 microns. Using a detector located with the chip, identification of a target in a test sample may be achieved at the site of the attachment of the biological molecule or anti-ligand.

In the next step, a 0.2 to 0.5 $\mu$m metal layer (e.g., aluminum) is deposited by vacuum evaporation. In addition to aluminum, suitable metals for circuitry include gold, silver, tin, copper, platinum, palladium, carbon, and various metal combinations. Special techniques for ensuring proper adhesion to the insulating substrate materials ($SiO_2$) are used with different metals.

The chip is next overcoated with a positive photoresist (Shipley, Microposit AZ 1350 J), masked (light field) with the circuitry pattern, exposed and developed. The photo-solubilized resist is removed, and the exposed aluminum is etched away. The resist island is now removed, leaving the aluminum circuitry pattern on the chip. This includes an outside perimeter of metal contact pads, the connective circuitry (wires), and the center array of micro-electrodes that serve as the underlying base for the addressable micro-locations.

Using PECVD, the chip is overcoated first with a 0.2 to 0.4 micron layer of $SiO_2$, and then with a 0.1 to 0.2 micron layer of silicon nitride ($Si_3N_4$). The chip is then covered with positive photoresist, masked for the contact pads and micro-electrode locations, exposed, and developed. Photosolubilized resist is removed, and the $SiO_2$ and $Si_3N_4$ layers are etched way to expose the aluminum contact pads and micro-electrodes. The surrounding island resist is then removed, the connective wiring between the contact pads and the micro-electrodes remains insulated by the $SiO_2$ and $Si_3N_4$ layers.

The $SiO_2$ and $Si_3N_4$ layers provide important properties for the functioning of the device. First, the second $SiO_2$ layer has better contact and improved sealing with the aluminum circuitry. It is also possible to use resist materials to insulate and seal. This prevents undermining of the circuitry due to electrolysis effects when the micro-electrodes are operating. The final surface layer coating of $Si_3N_4$ is used because it has much less reactivity with the subsequent reagents used to modify the micro-electrode surfaces for the attachment of specific binding entities.

At this point the micro-electrode locations on the device are modified with a specialized permeation and attachment layer, which is a crucial element required for the active functioning of the device. The objective is to create on the micro-electrode an intermediate permeation layer with selective diffusion properties and an attachment surface layer with optimal binding properties. The attachment layer should preferably have from $10^5$ to $10^7$ functionalized locations per square micron ($\mu m^2$) for the optimal attachment of specific binding entities. The attachment of specific binding entities must not overcoat or insulate the surface to percent the underlying micro-electrode from functioning. A functional device requires some fraction (~5% to 25%) of the actual metal electro-electrode surface to remain accessible to solvent ($H_2O$) molecules, and to allow the diffusion of counter-ions (e.g., $Na^+$ and $Cl^-$) and electrolysis gases (e.g., $O_2$ and $H_2$) to occur.

The intermediate permeation layer must also allow diffusion to occur. Additionally, the permeation layer should have a pore limit property that inhibits or impedes the larger binding entities, reactants, and analytes from physical contact with the micro-electrode surface. The permeation layer keeps the active micro-electrode surface physically distinct from the binding entity layer of the micro-location.

In terms of the primary device function, this design allows the electrolysis reactions required for electrophoretic transport to occur on micro-electrode surface, but avoids adverse electrochemical effects to the binding entities, reactants, and analytes.

One preferred procedure for the derivatization of the metal micro-electrode surface uses aminopropyltriethoxy silane (APS). APS reacts readily with the oxide and/or hydroxyl groups on metal and silicon surfaces. APS provides a combined permeation layer and attachment layer, with primary amine groups for the subsequent covalent coupling of binding entities. In terms of surface binding sites, APS produces a relatively high level of functionalization (i.e., a large number of primary amine groups) on slightly oxidized aluminum surfaces, an intermediate level of functionalization on $SiO_2$ surfaces, and very limited functionalization of $Si_3N_4$ surfaces, and very limited functionalization of $Si_3N_4$ surfaces.

The APS reaction is carried out by treating the whole device (e.g., a chip) surface for 30 minutes with a 10% solution of APS in toluene at 50° C. The chip is then washed in toluene, ethanol, and then dried for one hour at 50° C. The micro-electrode metal surface is functionalized with a large number of primary amine groups ($10^5$ to $10^6$ per square micron). Binding entities can now be covalently bound to the derivatized micro-electrode surface.

ii. Micromachining

International patent application Publication Nos. WO 95/12808 and WO 96/07917 describe micro-machining techniques (e.g., drilling, milling, etc.) and non-lithographic techniques to fabricate devices. In general, the resulting devices have relatively larger micro-locations (>100 microns) than those produced by microlithography. These devices could be used for analytical applications, as well as for preparative type applications, as well as for preparative type applications, such as biopolymer synthesis. Large addressable locations could be fabricated in three dimensional formats (e.g., tubes or cylinders) in order to carry a large amount of binding entities. Such devices could be fabricated using a variety of materials including, but not limited to, plastic, rubber, silicon, glass (e.g., microchannelled, microcapillary, etc.), or ceramics. In the case of micromachined devices, connective circuitry and large electrode structures can be printed onto materials using standard circuit board printing techniques known to those skilled in the art.

In the instant application, the chips are preferably designed to contain detector elements, e.g., photodiodes, that are incorporated into the semicondutor layer and coupled through optical paths, such as by waveguides or other means, to the other optical paths of the chip. In preferred embodiments, the detector element is comprised of a linear array of photodiodes with an approximate resolution of 1–5 microns, preferably 1–2 microns. Using a detector located with the chip, identification of a target in a test sample may be achieved at the site of the attachment of the biological molecule or anti-ligand.

Figure 15:
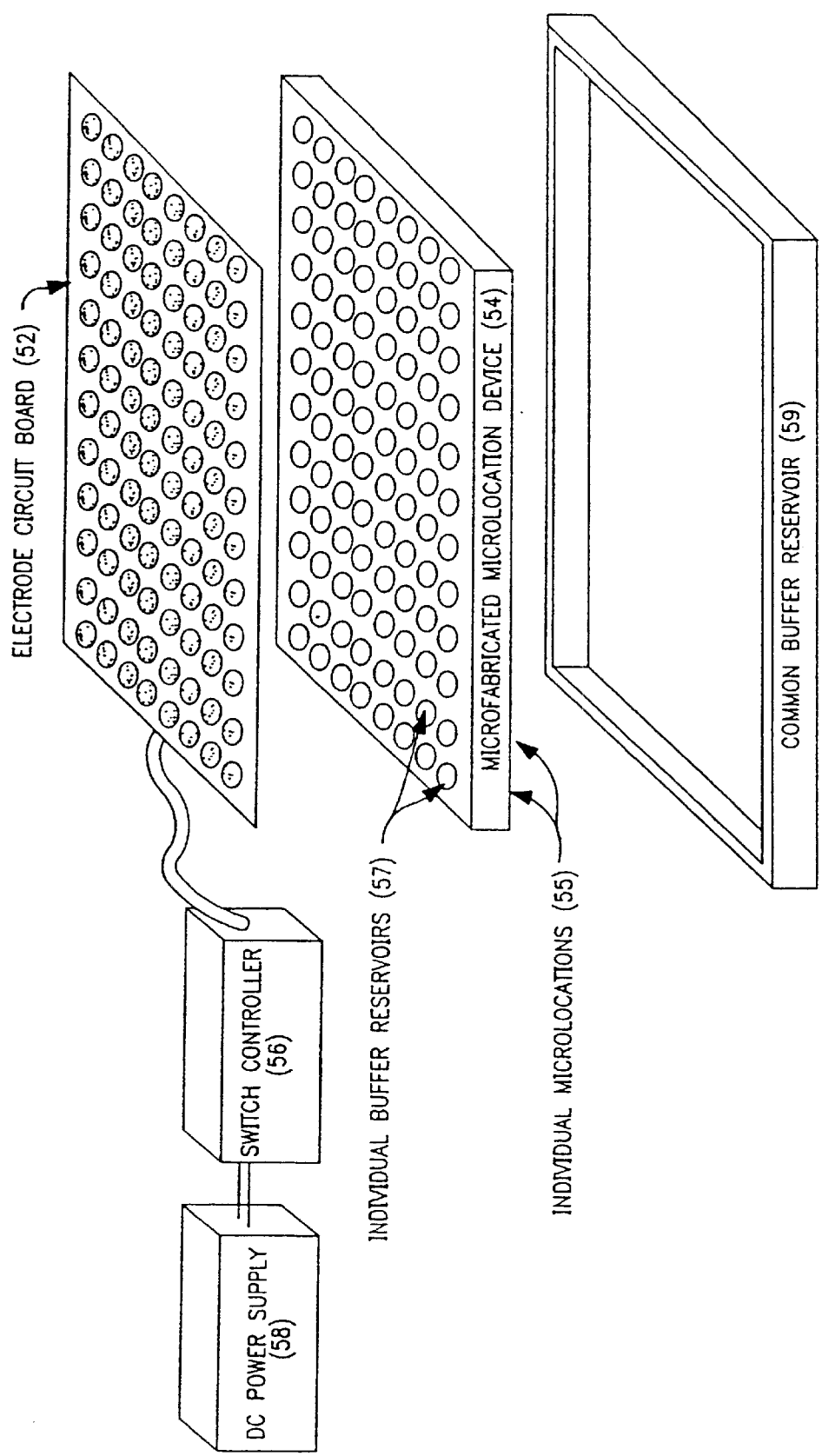
FIG. 15 shows a blown-up schematic diagram of a micro-machined 96 micro-locations device.
Figure 16:
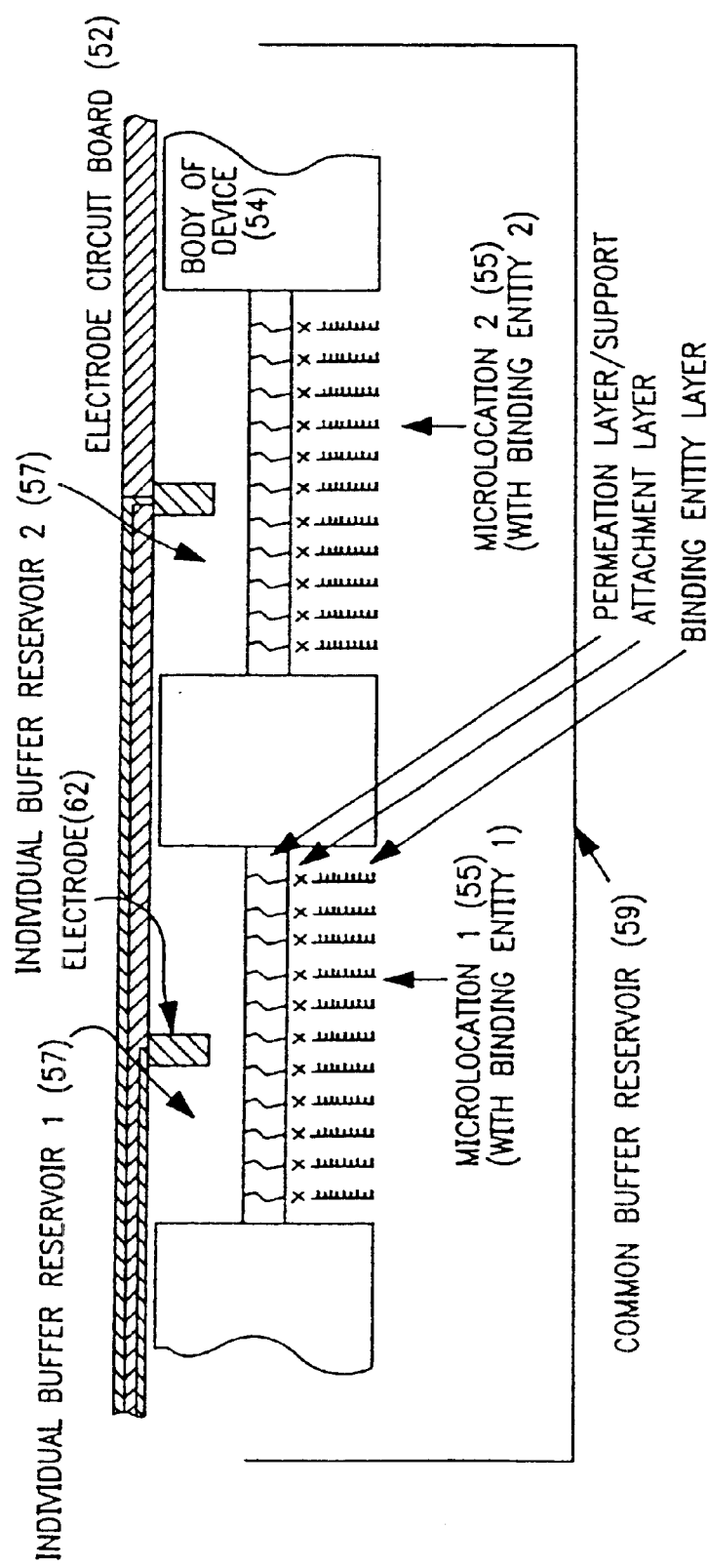
FIG. 16 is the cross-section of a micro-machined device.

Addressable micro-location devices can be fabricated relatively easily using micro-machining techniques. FIG. 15 of WO 95/12808 shows a schematic of a representative 96 micro-location device. This micro-location device is fabricated from a suitable material stock (2 cm×4 cm×1 cm), by drilling 96 proportionately spaced holes (1 mm in diameter) through the material. An electrode circuit board is formed on a thin sheet of plastic material stock, which fit precisely over the top of the micro-location component. The underside of the circuit board contains the individual wires (printed circuit) to each micro-location. Short platinum electrode structures (~3–34 mm) are designed to extend down into the individual micro-location chambers. The printed circuit wiring is coated with a suitable water-proof insulating material. The printed circuit wiring converges to a socket, which allows connection to a multiplex switch controller and DC power supply. The device is partially immersed and operates in a common buffer reservoir.

While the primary function of the micro-locations in devices fabricated by micro-machining and microlithography techniques is the same, their designs are different. In devices fabricated by microlithography, the permeation and attachment layers are formed directly on the underlying metal micro-electrode. In devices fabricated by micro machining techniques, the permeation and attachment layers are physically separated from their individual metal electrode structure by a buffer solution in the individual chamber of reservoir. In micro-machined devices the permeation and attachment layers can be formed using functionalized hydrophilic gels, membranes, or other suitable porous materials.

In general, the thickness of the combined permeation and attachment layers ranges from 10 $\mu m$ to 10 mm. For example, a modified hydrophilic gel of 26% to 35% polyacrylamide (with 0.1% polylysine), can be used to partially fill (~0.5 mm) each of the individual micro-location chambers in the device. This concentration of gel forms an ideal permeation layer with a pore limit of from 2 nm to 3 nm. The polylysine incoroporated into the gel provides primary amine functional groups for the subsequent attachment of specific binding entities. This type of gel permeation layer allows the electrodes to function actively in the DC mode. When the electrode is activated, the gel permeation layer allows small counter-ions to pass through it, but the larger specific binding entity molecules are concentrated on the outer surface. Here they become covalently bonded to the outer layer of primary amines, which effectively becomes the attachment layer.

An alternative technique for the formation of the permeation and attachment layers is to incorporate into the base of each micro-location chamber a porous membrane material. The outer surface of the membrane is then derivatized with chemical functional groups to form the attachment layer. Appropriate techniques and materials for carrying out this approach are known to those skilled in the art.

The above description for the design and fabrication of a device should not be considered as a limit to other variations or forms of the basic device. Many variations of the device with larger or smaller numbers of addressable micro-locations are envisioned for different analytical and preparative applications. Variations of the device with larger addressable locations are envisioned for preparative biopolymer synthesis applications. Variations are also contemplated as electronically addressable and controllable reagent dispensers for use with other devices, including those produced by microlithographic techniques.

c. Self-addressing of Chips

The chips and devices described in International patent application Publication Nos. WO 95/12808 and WO 96/07917 are able to electronically self-address each micro-location with a specific binding entity. The device itself directly affects or causes the transport and attachment of specific binding entities to specific micro-locations. The device self-assembles itself in the sense that no outside process, mechanism, or equipment is needed to physically direct, position, or place a specific binding entity at a specific micro-location. This self-addressing process is rapid and specific, and can be carried out in either a serial or parallel manner.

Figure 8:
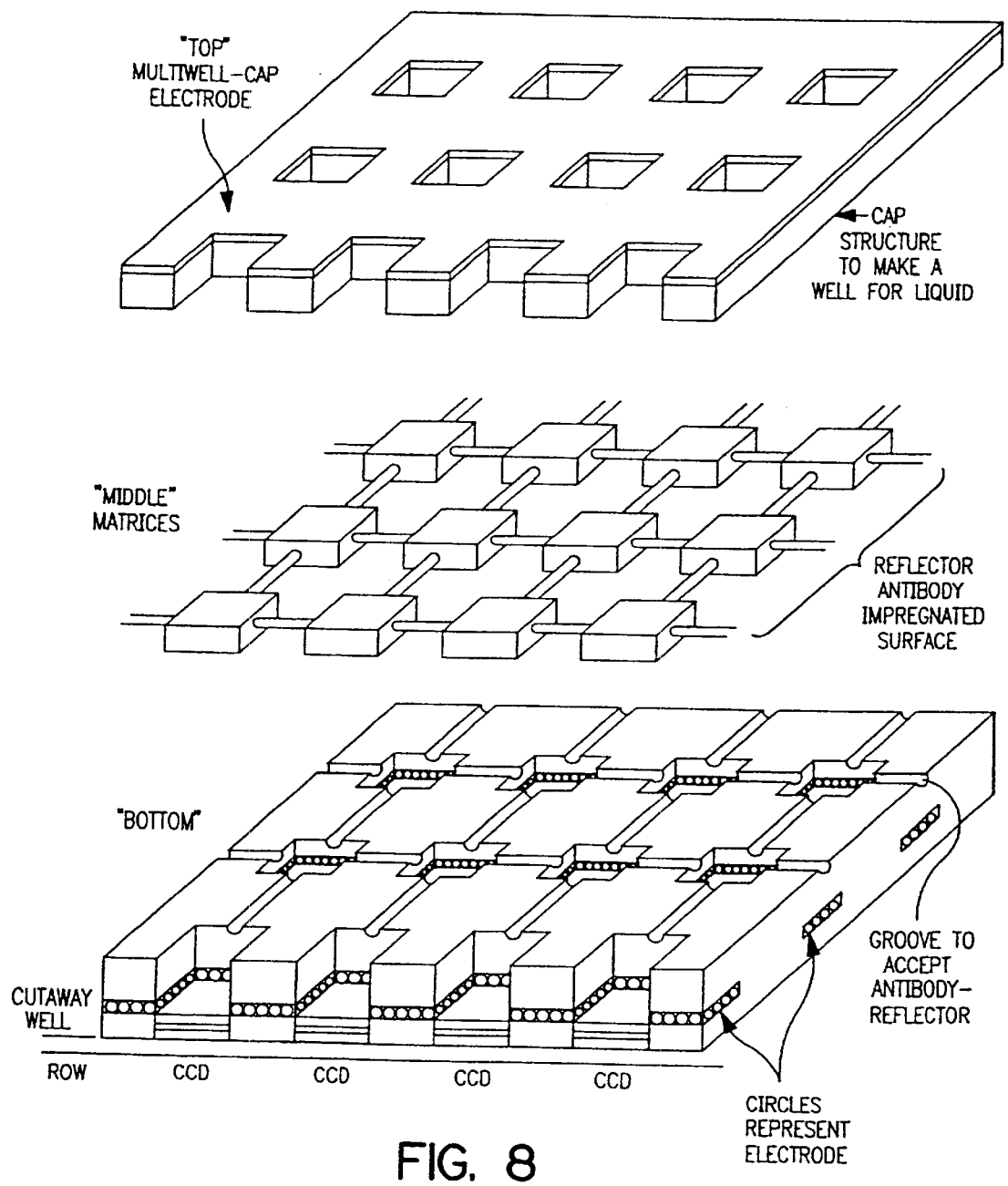
FIG. 8 is a schematic cross-sectional diagram of a three layer multi-well CCD. chip (a chip containing a photodiode/CCD).
Figure 9A:
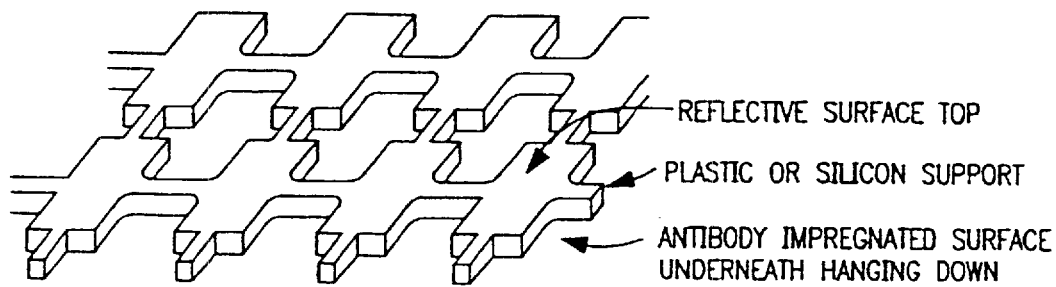
FIG. 9 shows a blown-up schematic diagram of a multi-well CCD chip bottom layer and middle reflective layer and schematic diagram of an individual well.
Figure 9B:
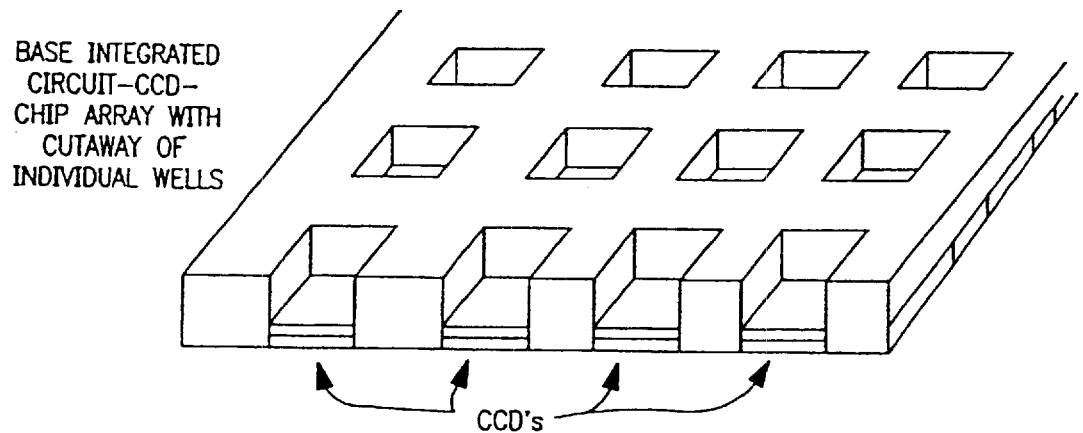
Figure 9C:
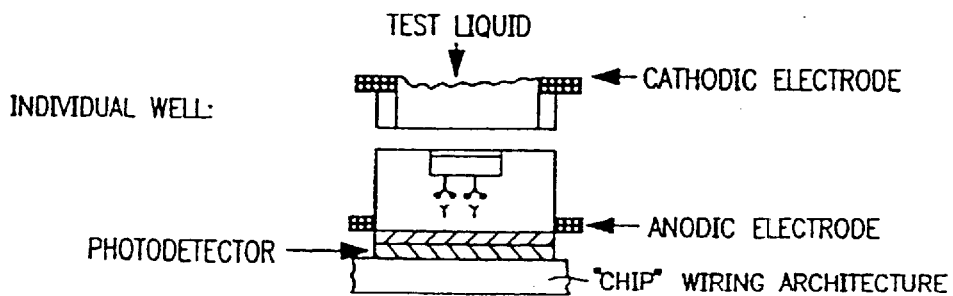
Figure 10A:
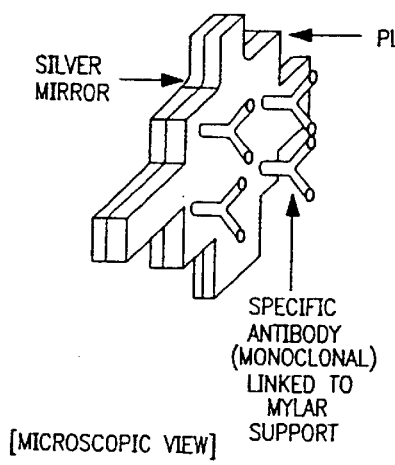
FIG. 10 shows a blown-up schematic diagram of specific antibodies attached to the middle reflective layer of the multi-well CCD chip of FIG. 8.
Figure 10B:
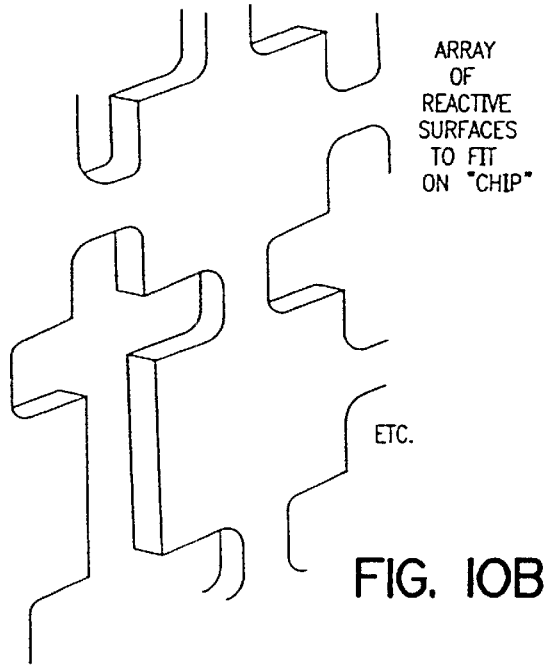

A device can be serially addressed with specific binding entities by maintaining the selected micro-location in a DC mode and at the opposite charge (potential) to that of a specific binding entity. All other micro-locations are maintained at the same charge as the specific binding entity. In cases where the binding entity is not in excess of the attachment sites on the micro-location, it is necessary to activate only one other micro-electrode to affect the electrophoretic transport to the specific micro-location. The specific binding entity is rapidly transported (in a few seconds, or preferably less than a second) through the solution, and concentrated directly at the specific micro-location where it immediately becomes covalently bonded to the special surface. The ability to electronically concentrate reactants or analytes (70) on a specific micro-location (72) is shown in FIG. 7 of the patent. All other micro-locations remain unaffected by that specific binding entity. Any unreacted binding entity is removed by reversing the polarity of that specific micro-location, and electro-phoresing it to a disposal location. The cycle is repeated until all desired micro-locations are addressed with their specific binding entities. FIG. 8 of the patent shows the serial process for addressing specific micro-locations (81, 83, 85) with specific oligonucleotide binding entities (82, 84, 86).

The parallel process for addressing micro-locations simply involves simultaneously activating a large number (particular group or line) of micro-electrodes so that the same specific binding entity is transported, concentrated, and reacted with more than one specific micro-locations.

When used, the chip is contacted with a sample, such as a body fluid, particularly urine, sputum or blood. The chip is then contacted with a composition containing a luciferin or, preferably a luciferase, conjugated or linked or fused to an antibody or antibody binding portion thereof or a plurality of such fusions. The antibodies or portions thereof are each specific for the antigens of interest. Detection is effected by reacting the chip with a bioluminescence generating system that generates light detected by the photodiodes.

3. Attachment of Biological Molecules to the Surface of Chips

A large variety of methods are known for attaching biological molecules, including proteins, nucleic acids and peptide nucleic acids, to solid supports [see. e.g., Affinity Techniques. Enzyme Purification: Part B. *Methods in Enzymol.*, Vol. 34, ed. W. B. Jakoby, M. Wilchek, Acad. Press, N.Y. (1974) and Immobilized Biochemicals and Affinity Chromatography, Advances in *Experimental Medicine and Biology*, vol. 42, ed. R. Dunlap, Plenum Press, N.Y. (1974); U.S. Pat. No. 5,451,683, see, also U.S. Pat. Nos. 5,624,711, 5,412,087, 5,679,773, 5,143,854], particularly silicon chips are known.

These methods typically involve derivatization of the solid support to form a uniform layer of reactive groups on the support surface and subsequent attachment of the biological molecule to the derivatized surface via a covalent bond between the reactive group and a reactive moiety present on the biological molecule. Presently preferred methods are those applicable for the derivatization and attachment of biological molecules to silica substrates, particularly methods for derivatizing the silica surface of microelectronic chip devices.

a. Derivatization of Silica Substrates

Numerous methods for derivitizing silica surfaces or for coating surfaces with silica and then derivatizing the surface are known. A number of reagents may be used to derivatize the surface of a silica substrate. For example, U.S. Pat. No. 4,681,870 describes a method for introducing free amino or carboxyl groups onto a silica matrix. Alternatively, a layer of free amino groups or carboxyl groups may be introduced using amino- and carboxymethyl silane derivatives, such as 3-aminopropyltriethoxysilane, 3-aminopropyltrimethoxysilane, 4-aminobutyltriethoxysilane, (aminoethylaminomethyl) phenethyltrimethoxysilane, 2-(carbomethoxy) ethyltrichlorosilane, (10-carbomethoxydecyl)dimethylchlorosilane and 2-(carbomethoxy) ethylmethyldichlorosilane (e, see Hulls Catalog).

The silica surface may also be derivatized to introduce a layer of hydroxyl groups using alkyl- and alkoxyalkyl halogenated silane derivatives. The alkoxy groups of trialkoxysilanes are hydrolyzed to their corresponding silanol species, which may occur during the formal preparation of aqueous solutions or the reaction of the silane with the absorbed moisture on the silica substrate. The silanols usually condense with themselves or with alkoxysilanes to form siloxanes. The silanol-containing species are highly reactive intermediates that react with the hydroxyl groups on the surface of the silica [e.g., see Mohsen et al. (1995) *J.*

*Oral Rehabil.* 22:213–220]. Furthermore, a silica matrix may also be activated by treatment with a cyanogen halide under alkaline conditions. The anti-ligand is covalently attached to the surface upon addition to the activated surface.

The selection and use of an appropriate derivatizing reagent is within the skill of the skilled artisan. For example, the selection of the appropriate silane derivative may be accomplished by empirical evaluation of silanes within the predicted categories. In preparing these silica substrates, the entire surface of the substrate may be derivatized with the appropriate silane derivative or the surface can be derivatized at only plurality of locations to form a discrete array. The reagents and solutions containing biological molecules may be added to the surface of the silica manually or by using a tamping tool or any other tool known to those of skill in the art for this purpose.

b. Attachment of Biological Molecules

The attachment of biological molecules to the surface of silica substrates may be effected using procedures and techniques known in the art and described herein. The attachment of the biological molecule may also be effected in the absence or presence of a linker moiety (e.g., see Section D1 below). Any linker known to those of skill in the art may be used herein.

Derivatized silica substrates containing a layer of free amino or carboxyl groups or other suitable group may subsequently be covalently linked to a free carboxyl or amino group on a heterobifunctional linker or a biological molecule, such as a protein, a protein nucleic acid or other anti-ligand, in the presence of a carbodiimide. The use of carbodiimides [e.g., N-ethyl-N'-($\gamma$-dimethylaminopropylcarbodiimide], as coupling agents is well known to those of skill in the art [see, e.g., Bodansky et al. in "The Practice of Peptide Synthesis," Springer-Verlag, Berlin (1984)].

Another method for attaching biological molecules involves modification of a silica surface through the successive application of multiple layers of biotin, avidin and extenders [see, e., U.S. Pat. No. 4,282,287]; other methods involve photoactivation in which a polypeptide chain is attached to a solid substrate by incorporating a light-sensitive unnatural amino acid group into the polypeptide chain and exposing the product to low-energy ultraviolet light [see, e.g., U.S. Pat. No. 4,762,881]. Oligonucleotides have also been attached using a photochemically active reagents, such as a psoralen compound, and a coupling agent, which attaches the photoreagent to the substrate [see, e.g., U.S. Pat. No. 4,542,102 and U.S. Pat. No. 4,562,157]. Similar methods are applicable to peptide nucleic acids. Photoactivation of the photoreagent binds a nucleic acid molecule or peptide nucleic acid molecule to the substrate to give a surface-bound probe. In certain embodiments, the photoactivation may occur in situ by selecting an appropriate bioluminescence generating system with an appropriate emission wavelength sufficient to photoactivate and immobilize the nucleic acid.

Furthermore, U.S. Pat. No. 5,451,683 describes a technique for attaching biochemical ligands to surfaces of matrices by attachment of a photoactivatable biotin derivatives. Photolytic activation of the biotin derivatives for biotin analogs having strong binding affinity for avidin or streptavidin. The biotinylated ligands are immobilized on activated regions previously treated with avidin or streptavidin.

The attachment of anti-ligands to a matrix material may also be achieved electronically. Self-addressable, self-assembling microelectronic systems and devices for electronically controlling the transport and binding of specific binding entities to specific microlocations on a matrix [e.g., see International Patent Application Publication Nos. WO 95/12808; WO 96/01836 and WO 96/07917, U.S. Pat. No. 5,632,957, 5,605,662]. Electronic control of the individual micro-locations may be effected whereby voltage or current is controlled. When one aspect is set, the other may be monitored. For example, when voltage is set, the current may be monitored. Alternatively, when voltage is set, the current may be monitored. The voltage and/or current may be applied in a direct current mode, or may vary with time.

The spatial addressability afforded by these methods allows the formation of patterned surfaces having preselected reactivities. For example, by using lithographic techniques known in the semiconductor industry, light can be directed to relatively small and precisely known locations on the surface. It is, therefore, possible to activate discrete, predetermined locations on the surface for attachment of anti-ligands. The resulting surface will have a variety of uses. For example, direct binding assays can be performed in which ligands can be simultaneously tested for affinity at different anti-ligands attached to the surface.

For example, the attachment of biological molecules to a silica surface of the non-self addressable chip using alkoxysilanes typically involves pre-hydrolysis of the surface. All of the following operations should be performed in a laminar flow hood/clean environment to avoid contamination with dust, organic particles and other particulates. Typically, the appropriate alkoxysilane is dissolved in a 3:1 ethanol-water solution at room temperature for 12 hours. The chip is treated by flooding a selected area of the chip repeatedly using fresh aliquots of the silane-alcohol solution. After this treatment, the chip is washed using large amounts of absolute ethanol, followed by washes in THF or dioxane, hexane (ultrapure) and finally pentane, which is evaporated under a stream of dry nitrogen.

The efficiency of the derivatization of the surface of the chip may be determined by coupling an appropriate fluorescent amine (carboxyl derivatized) or fluorescent carboxylic acid (amino derivatized) to the surface of the chip by exciting the fluorescence of the bound molecules using a laser of appropriate wavelength. Appropriate compounds for this purpose may be amino, carboxyl or other reactive derivatives of fluorescein, rhodamine or Texas Red, which are known to those of skill in the art and are also commercially available (e.g., see Molecular Probes, Inc.).

The isothiocyanates of fluorescein, rhodamine, or Texas Red, for example, react in an irreversible and covalent manner with any free amino groups on the silica surface. A solution of an effective concentration of fluorescein (about 10 mM) isothiocyanate (mixed isomers) in acetone or dioxane is placed on the amine-derivatized silica of the chip for sufficient time, typically about 30 minutes at ambient temperatures. To remove all unreacted material, the chip is washed with hot (i.e., 60° C.) solutions of acetone, hexane and pentane or other suitable solvent. A region on the same chip that has not been chemically derivatized is similarly treated with the fluorescein isothiocyanate as a control. A small amount of direct covalent reaction with the glass is possible and thus the control should be performed to indicate background levels. The fluorescence of the bound fluorescein can be excited using a suitable sources, such as an argon ion laser (e.g., 488 nm), preferably using a 45-degree angle geometry. The argon laser can further contain a photomultiplier equipped with a 10 nm bandpass filter for detecting the emitted fluorescence signal at about 520 nm. The amount of fluorescence detected is a function of the extent and efficiency of derivatization.

In another embodiment, provided herein, a reflective surface,. e.g., MYLAR, may be derivatized as described above such that an anti-ligand may be immobilized directly to the protective, activated outer surface overlaying the reflective metal layer, such as a derivatized silane layer. In this embodiment, light generated by the bioluminescence generating system will not be scattered or absorbed by the anti-ligand because the photodiodes are not occuled by bound anti-ligand.

D. Formation of Luciferase Conjugates

1. Linkers

The conjugation of a luciferase to an anti-ligand, e.g., an antibody, oligonucleotide or peptide nucleic acid, may be achieved in the absence or presence of a linker sequence using methods known to those of skill in the art. Any linker known to those of skill in the art may be used herein. Methods for linking a luciferase to an antibody are described in U.S. Pat. Nos. 4,657,853; 5,486,455 and International Patent Application Publication No. WO 96107100.

Other linkers are suitable for incorporation into chemically linked proteins. Such linkers include, but are not limited to: disulfide bonds, thioether bonds, hindered disulfide bonds, and covalent bonds between free reactive groups, such as amine and thiol groups. These bonds are produced using heterobifunctional reagents to produce reactive thiol groups on one or both of the polypeptides and then reacting the thiol groups on one polypeptide with reactive thiol groups or amine groups to which reactive maleimido groups or thiol groups can be attached on the other. Other linkers include, acid cleavable linkers, such as bismaleimideothoxy propane; cross linkers that are cleaved upon exposure to UV or visible light. In some embodiments, several linkers may be included in order to take advantage of desired properties of each linker.

Chemical linkers and peptide linkers may be inserted by covalently coupling the linker to the anti ligand and to the surface of the chip. The heterobifunctional agents, described below, may be used to effect such covalent coupling. Peptide linkers may also be linked by expressing DNA encoding the linker and the anti ligand, e.g., an antibody,, as a fusion protein.

Numerous heterobifunctional cross-linking reagents that are used to form covalent bonds between amino groups and thiol groups and to introduce thiol groups into proteins, are known to those of skill in this art (see, e.g., the PIERCE CATALOG, ImmunoTechnology Catalog & Handbook, 1992–1993, which describes the preparation of and use of such reagents and provides a commercial source for such reagents; see, also, e.g., Cumber et al. (1992) *Bioconjugate Chem.* 3:397–401; Thorpe et al. (1987) *Cancer Res.* 47:5924–5931; Gordon et al. (1987) *Proc. Natl. Acad Sci.* 84:308–312; Walden et al. (1986) *J. Mol. Cell Immunol.* 2:191–197; Carlsson et al. (1978) *Biochem. J.* 173: 723–737; Mahan et al. (1987) *Anal. Biochem.* 162:163–170; Wawryznaczak et al. (1992) *Br. J. Cancer* 66:361–366; Fattom et al. (1992) *Infection & Immun.* 60:584–589). These reagents may be used to form covalent bonds between the anti ligand and the luciferase molcecule. These reagents include, but are not limited to: N-succinimidyl-3-(2-pyridyidithio)-propionate (SPDP; disulfide linker); sulfos-uccinimidyl 6-[3-(2-pyridyidithio)propionamido]hexanoate (sulfo-LC-SPDP); succinimidyl-oxycarbonyl-α-methyl benzyl thiosulfate (SMBT, hindered disulfate linker); succinimidyl 6-[3-(2-pyridyldithio) propionamido]hexanoate (LC-SPDP); sulfosuccinimidyl 4-(N-maleimidomethyl) cyclohexane-1-carboxy-late (sulfo-SMCC); succinimidyl 3-(2-pyridyldithio)butyrate (SPDB; hindered disulfide bond linker); sulfosuccinimidyl 2-(7-azido-4-methyl-coumarin-3-acetamide) ethyl-1,3'-dithiopropionate (SAED); sulfosuccinimidyl 7-azido-4-methylcoumarin-3-acetate (SAMCA); sulfosuccinimidyl 6-[alpha-methyl-alpha-(2-pyridyidithio)toluamido]hexanoate (sulfo-LC-SMPT); 1,4-di-[3'-(2'-pyridyldithio)propionamido]butane (DPDPB); 4-succinimidyloxycarbonyl-α-methyl-α-(2-pyridylthio) toluene (SMPT, hindered disulfate linker) ;sulfosuccinimidyl6[α-methyl-α-(2-pyridyidithio)-toluamido]hexanoate (sulfo-LC-SMPT); m-maleimidobenzoyl-N-hydroxy-succinimide ester (MBS); m-maleimidobenzoyl-N-hydroxysulfosuccinimide ester (sulfo-MBS); N-succinimidyl(4-iodoacetyl)aminobenzoate (SIAB; thioether linker); sulfosuccinimidyl(4-iodoacetyl) amino benzoate (sulfo-SIAB); succinimidyl4(p-maleimidophenyl)butyrate (SMPB); sulfo-succinimidyl4-(p-maleimidophenyl)butyrate (sulfo-SMPB); azidobenzoyl hydrazide (ABH).

Acid cleavable linkers, photocleavable and heat sensitive linkers may also be used, particularly where it may be necessary to cleave the targeted agent to permit it to be more readily accessible to reaction. Acid cleavable linkers include, but are not limited to, bismaleimideothoxy propane; and adipic acid dihydrazide linkers (see, e.g., Fattom et al. (1992) *Infection & Immun.* 60:584–589).

2. Luciferase Fusion Proteins

In addition to antibody-luciferase conjugates, a recombinant luciferase protein fusion to an anti ligand, e.g., an antibody or F(Ab)$_2$ antigen-binding fragment thereof, is also contemplated for use herein. For example, the DNA encoding a monoclonal antibody may be ligated to DNA encoding a luciferase or the luciferase may be linked to an antibody [see, e.g., U.S. Pat. No. 4,478,817, which describes antibody/luciferase conjugates and the use thereof].

3. Nucleic Acid and Peptide Nucleic Acid Conjugates

The luciferase molecules described herein may also be conjugated to nucleic acids or peptide nucleic acids. The coupling may also be effected in the absence or presence of a linker. Methods for conjugating nucleic acids, at the 5' ends, 3' ends and elsewhere, to the amino and carboxyl terminii and other sites in proteins are known to those of skill in the art (for a review see em., Goodchild, (1993) In:*Perspectives in Bioconiugate Chemistry,* Mears, Ed., American Chemical Society, Washington, D.C. pp.77–99. For example, proteins have been linked to nucleic acids using ultraviolaet irradiation (Sperling et al. (1978) *Nucleic Acids Res.* 5:2755–2773; Fiser et al. (1975) *FEBS Lett.* 52:281–283), bifunctional chemicals (Bäumert et al. (1978) *Eur. J. Biochem.* 89353–359; and Oste et al. (1979) *Mol. Gen. Genet.* 168::81–86) photochemical cross-linking (Vanin et al. (1981) *FEBS Lett.* 124:89–92; Rinke et al. (1980) *J.Mol.Biol.* 137:301–314; Millon et al. (1980) *Eur. J. Biochem.* 110:485–454).

In addition, the carboxyl terminus of a luciferase may be conjugated to one of the free amino groups of peptide nucleic acids [e.g., see Nielsen et al. (1990) *Science* 254:1497–1500; Peffer et al. (1993) *Proc. Natl. Acad. Sci. U.S.A.* 90:10648–10652) using standard carbodiimide peptide chemistry.

Additional sites for conjugation can also be introduced into the nucleic acid molecule by chemical modification of one or more position or by the introduction of a small antigenic determinant covalently coupled to the 5' or 3'-end of the molecule. A variety of small antigenic determinants (i.e., His Tags, fig antigens, S-Tags, dioxigenin and the like) are known to those of skill in the art and are also commercially available [e.g., Boehringer Mannheim, Indianapolis, Ind.; Novagen, Inc., Madison Wis.]. Modified nucleic acids and peptide nucleic acid analogs may also be prepared by direct chemical synthesis using standard phosphoroamidite chemistry and commercially available modified nucleoside triphosphate analogs (ea., 5'-thiolated nucleoside triphosphates and oligonucleotides). 5' and 3' thiolated oligonucleotides are also commercially available [e.g., Operon Technologies, Alameda, Calif.].

E. Radiolaria and Diatoms for Depositing Silica on Matrices

A method of using biomineralization to deposit silica on a matrix material is also provided herein. The method uses diatom and radiolaria enzymes and cell wall proteins to effect the polymerization of silicon dioxide along the interface region of the matrix to form a matrix-silicate mesostructure. This method may be used in the semiconductor industry for the preparation of silicate chips that have a variety of end use applications.

Organisms such as diatoms and radiolaria synthesize elaborate biomineral silica-based cell walls, also termed frustulum/frustles or exoskeletons, which display hierarchichal structures patterned on scales from less that a micrometer to millimeters [e.g., see in general, Anderson (1983) in *Radiolaria,* Spriner-Verlag, N.Y.; Sullivan (1986) *Ciba Found. Symp.* 121:59–89]. The two main principles of the architecture in diatom cell walls are cell walls with radial symmetry (centric diatoms; e.g., *Cylindrotheca crypta*) and those with bilateral symmetry (pennate diatoms; e.g., *Navicula peliculosa* and *C. fusiformis*).

The diatom cell wall includes of two parts, the epitheca and the hypotheca. Each theca is composed of a valve and several silica strips, girdle bands, which are composed of amorphous, hydrated silica and other organic components [e.g., see Volcani (1981) in *Silicon and Siliceous Structures in Biological Systems,* Simpson and Volcani, eds, pp. 157–200, Springer-Verlag; Kroger et al. (1996) *EMBO* 13:4676–4683]. The major organic protein constituents of these cell walls is a family of proteins known as frustulins [see, e.g., Kroger et al. (1996) *Eur. J. Biochem.* 239:259–264]. In marine diatoms, new valves are produced after cell division and cytokinesis of the mother protoplast. The resulting daughter protoplast produces a new valve in a specialized intracellular organelle, the silica deposition vesicle. Silica is transported into the silicalemma where nucleation and epitaxial growth of Si monomers occurs on a template or more complex polymerization of silica occurs within the vesicles [see, e.g, Pickett-Heaps et al. (1979) *Bio. Cell.* 35:199–203; Sullivan (1986) *Ciba Found. Symp.* 121:59–89; Pickett-Heaps et al. (1990) *Pro Phycol. Res.* 7:1–186].

In radiolaria, the deposition of the silicate skeleton is associated with a cytoplasmic sheath that encloses, molds and deposits the skeleton termed "cytokalymma". The thickness of the skeleton may be influenced by the physiological state of the organism. The cytokalymma may function in an analogous manner to the silicalemma in the silica deposition in diatoms.

Artificial inorganic assemblies that mimic diatom and radiolaria exoskeletons have been described [e.g., see Oliver et al. (1995) *Nature* 378:47–50; U.S. Pat. Nos. 5,057,296, 5,108,725 and 5,364,797]. Several morphologies of mesophases may be formed, esg, lamellar, hexagonal and cubic mesostructures, depending on the selected starting materials and conditions used. These crystalline mesostructures, however, may only be formed at higher temperatures, which may be unsuitable for use with certain matrix materials.

Models have been proposed to explain the biomineralization process and also the formation and morphology of these surfactant-silicate mesostructures [see, e.g., Sullivan (Monnier et al. *Science* 261:1299–1303]. For example, it is postulated that the control of the silicate wall thickness is related to the double layer potential: silicate species only accumulate at the surface interface, which would thicken the wall or produce amorphous bulk $SiO_2$, does not occur because of the strong electrostatic replusion produced by the high negative charge on the silicate species at the high pHs at which these are formed, e.g., pH 12 and above [e.g., Ilier (1979) in *The Chemistry of Silica,* p. 182, Wiley, N.Y.].

Artificial assemblies of mesoprous crystalline material containing M41S has been included in sensor services, including biosensors [see, e.g., U.S. Pat. No. 5,364,797]. In biosensors, either biological analyte in each pair is affixed to the ultra-large pore crystalline substrate by covalent binding to silanols in the crystalline material [e.g., Harlow et al. *Antibodies, A Laboratory Manual,* Cold Spring Harbor Laboratory (1988)]. The analyte, e.g., an antibody, is attached and the interaction between the affixed analyte and the test sample is monitored.

The diatom silica-based cell walls are analogous in structure to the the above-described artificial assemblies. Thus, these silica deposits may have similar morphology and optical properties as the fiber optic sensors to the M41S artificial assemblies useful in biosensors and other molecular biological apparatus [see, e.g., U.S. Pat. No. 5,364,797].

In a method of using biomineralization using the enzymes and cell wall proteins of the silicalemma and/or silica deposition vesicles of diatoms to deposit silica on the surface of a matrix material of a chip is provided herein, silica may be deposited on a matrix material that has been linked with a uniform coating of a Si template using a silicalemma isolated from a diatom. The deposited silica may be attached to the matrix through another suitable linker, such as sugars or other diol-containing compounds. Alternatively, the components of the silicalemma may be further purified using methods known to those of skill in the art in protein chemistry.

F. Methods of use

1. Immunoassays

The chips described herein may be used in diagnostic assays. For example, the chips are used in an immunosandwich assay for the detection of infectious agents using antibodies directed against infectious microorganisms, e.g., bacteria, viruses, protozoa and other lower eukaryotic organisms [e.g., see FIG. 20]. A plurality of anti-ligands, e.g., antibodies, is linked to each location or microlocation on the chip or attached to an appropriate layer of the reflective middle layer of a multi-well chip creating a panel of antibodies raised against a particular microorganisms. The antibody-bound chip is placed directly into a sample of body fluid obtained from a patient, e.g, urine, sputum or blood.

Sufficient time is allowed to form antibody-antigen complexes and the chip is removed and rinsed thoroughly. A solution containing a plurality of secondary antibodies directed against a panel of known pathogens conjugated to a luciferase or luciferase fusion protein is added, which may be directed against the same antigen or another antigen present on the targeted species. Alternatively, a phage or virus may be employed that has been genetically engineered to contain DNA encoding a luciferase. Preferably, the virus or phage has a broad specificity.

The chip or individual well is washed, and the remaining components of the bioluminescence generating system, e.g., a luciferin and any necessary activators, are added. If an antigen has been detected, light is emitted from the bound luciferase, which is in turn detected by the photodiodes located within the semiconductor layer in the attached chip. In the multi-well chip system, the output signal of the bioluminescent reaction is increased by detecting light directly emitted from the reaction as well as light reflected off of the middle layer [e.g., see FIGS. 10 & 11]. The output signal may optionally be amplified and/or multiplexed prior to be sent to a computer processing unit for data analysis.

The assay may be used quantitatively by adding a known amount of luciferin to the well and by measuring the rate of the utilization of the luciferin (i.e., a reduction in light production over time is proportional to the amount present in the sample as compared to controls).

2. Nucleic Acid Hybridization Assays

The chips described herein may also be used in nucleic acid hybridization assays. For example, a desired nucleic acid or peptide nucleic acid probe or a nucleic acid with linked peptide is covalently coupled to the derivatized silica surface of the chip directly or via a linker group. The nucleic acids can be coupled to the entire surface or the chip or may be added to one or more microlocations on the chip in an array format.

The infectious agents present in the biological sample are lysed using chemical, enzymatic or physical means and the nucleic acids, preferably DNA, is isolated from the sample using standard methods known to those of skill in the art [e.g., see Sambrook et al., (1989) Molecular Cloning, 2nd ed., Cold Spring Harbor Laboratory Press, New York]. Alternatively, the sample can be analyzed without purification of the nucleic acid species.

The nucleic acid is resuspended in hybridization buffer and the sample is added to the surface of the chip and incubated at the desired hybridization temperature. After allowing sufficient time for hybridization, the chip is washed thoroughly and then washed under the appropriate stringency conditions as described herein, i.e. high medium or low. The complementary nucleic acid immobilized to the chip is detected by the addition of an anti ligand conjugated to a component of a bioluminescence generating system, preferably a luciferase. Presently preferred anti ligands are antibodies, or a F(Ab)$_2$ fragments thereof, that preferentially recognize double stranded nucleic acids or the associated small antigenic determinant. Antibodies that recognize double stranded DNA are associated with a number of autoimmune diseases [e.g., see Tsuzaka et al. (1996) *Clin. Exp. Immunol.* 106:504–508; Kanda et al. (1997) *Arthritis Rhem.* 40:1703–1711].

The chip or individual well is washed to remove unbound antibody luciferase conjugate, and the remaining components of the bioluminescence generating system, e.g., a luciferin and any necessary activators, are added. If a complementary nucleic acid or peptide nucleic acid has been detected, light is emitted from the bound luciferase, which is in turn detected by the photodiodes located within the semiconductor layer in the attached chip.

The assay may also be used quantitatively by adding a known amount of luciferin to the well and by measuring the rate of the utilization of the luciferin (i.e., a reduction in light production over time is proportional to the amount present in the sample as compared to controls).

3. Detection of Antibiotic Sensitivity

Among other uses for the chip is testing the sensitivity of a clinical isolate to known antibiotics or as a device to screen for antibacterial agents. For example, after detecting light emission from a targeted well, an isolate may be grown directly in the well for a short period by the addition of a suitable growth medium [e.g., L-broth or other undefined medium] followed by incubation under appropriate environmental conditions, such as temperatures of 20° C. to 42° C. under aerobic or anaerobic atmospheres.

The growing bacteria are then infected with a bacteriophage, such as lambda or P22 for enterobacteria, that has been genetically engineered to encode firefly luciferase, which requires available ATP as a co-factor [see e.g., Section B.4]. The expression of intracellular luciferase in these bacteria, in the presence of ATP, results in the production light.

The effectiveness of antibiotic therapy can be monitored directly in this system by incubating the bacteria with an effective concentration of an antibiotic and following subsequent light emission. If the antibiotic results in cell death, intracellular ATP pools will be depleted thereby inhibiting the bioluminescent reaction. The decrease in light is suggestive that the particular antibiotic or compound is effective. In other embodiments, the bacterial are incubated with test compounds and the antibacterial activity of the test compound is assessed.

4. Synthetic Synapse

Figure 17:
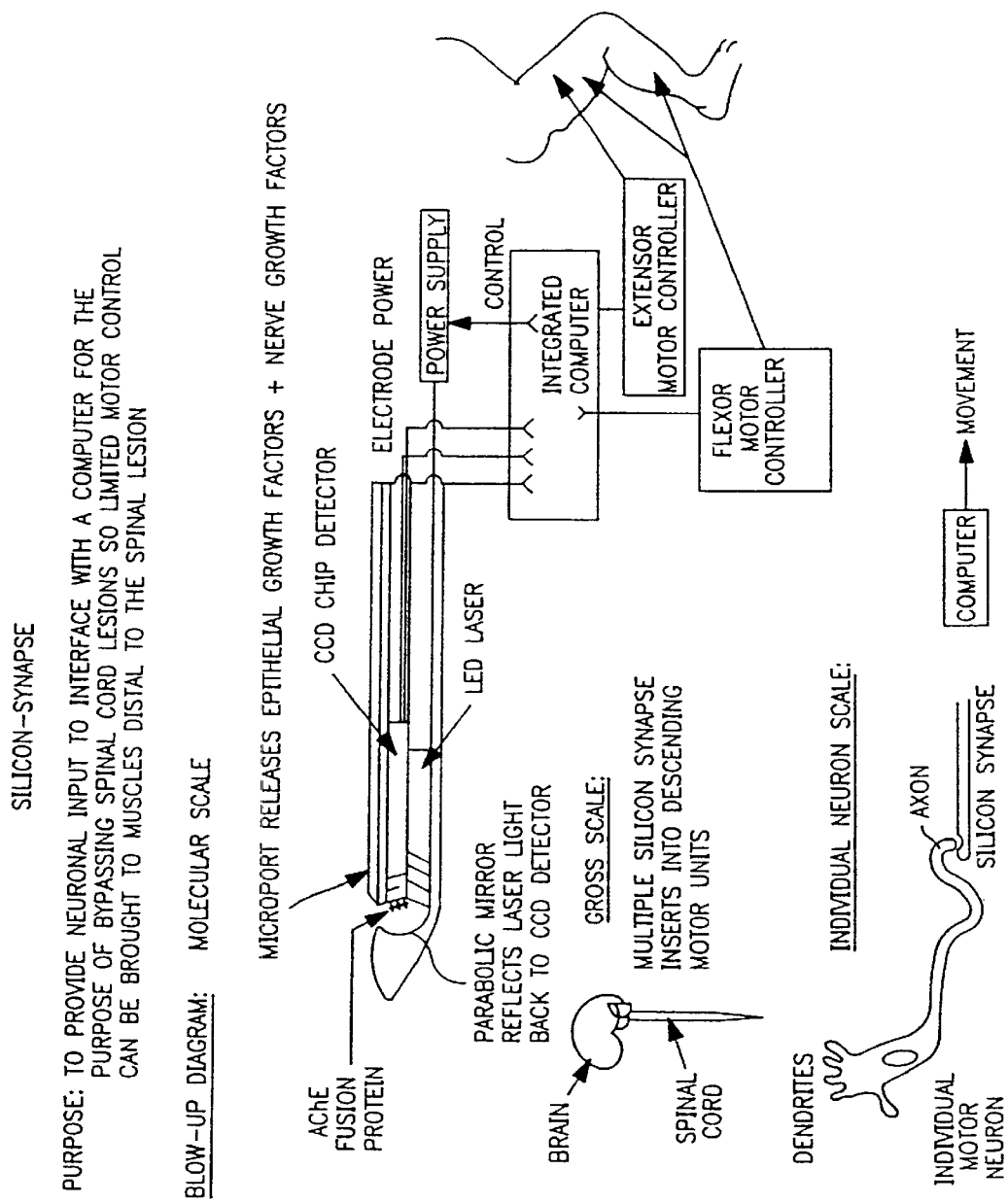
FIG. 17 shows a schematic representation of an artificial silicon-synapse.
Figure 18:
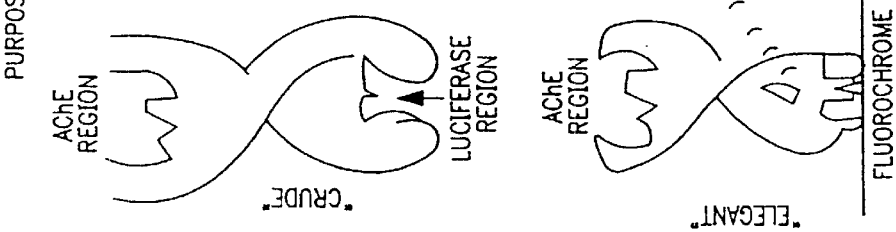
FIG. 18 shows a detailed schematic view of an acetylcholine esterase-luciferase fusion protein and an acetylcholine esterase-fluorochrome conjugate used in the silicon-synapse.

Versions of the chips provided herein may also be used to generate a synthetic neuronal synapse [e.g., see FIGS. 17–19]. A suitable enzyme, particularly, acetycholine esterase is fused to a luciferase, such as by recombinant expression. The luciferase is either in an inactive or active conformation. Suitable mutations in either protein may be selected to insure that luciferase can undergo appropriate conformational changes as described herein. The resulting fusion is attached to a chip, such as a chip provided herein. The neuron or bundle of neurons is kept in close proximity to the fusion protein linked to the chip by providing neuronal growth factors, e.g., EGF or NGF, near the location of the chip through a microport to promote and maintain local neurite outgrowth [see FIG. 17].

The silicon-synapse electrodes may be permanently implanted in an afflicted patient by insertion into the appropriate stereotaxic locations in the spinal cord by MRI localization [see FIG. 19]. To implant the electrodes, microholes are drilled into the spinal cord using a suitable laser, such as a $CO_2$ laser, and the electrode is placed into proximity of a known nerve fiber or bundle. The placement of the silicon-synapse may be from superficial to deep within the spinal cord along known neuronal pathways. Exact tracing of the appropriate neuron is preferable, though not essential, because the human brain will reprogram itself to send the signal along those neurons that transmit the proper signal.

The transmission of neuronal impulses involves various neurotransmitters, such as acetylcholine, which are released into the synapse. Upon binding of the ligand to the enzyme, such as the binding of acetylcholine to the esterase, the linked luciferase is, if previously inactive, is activated by the binding, or if previously active, is inactivated by the binding [see FIG. 18]. In the presence of the remaining components of a bioluminescence generating system, light is produced (or is quenched), which change is detected by the photodiodes associated with the chip. This detection generates one or more electrical or data signals that is/are sent through one or more wires leading to a computer, such a miniature computer that is attached to a belt, which processes the information. The processed information is transmitted by appropriate means, such as a fiber, to one or more electrodes, which are attached to any desired device or effector, particularly a muscle. Upon receipt of the signal, work, such as a muscle twitch, occurs and body movements may be initiated. The devices will be inserted in a manner that bypasses a lesioned area of the spinal cord [see, e.g., see FIG. 17].

Alternatively, the acetylcholine binding region of acetylcholine esterase may be fused to a fluorochrome or phycobiliprotein and used in conjunction with a laser. In this embodiment, monochromatic light of a known wavelength is generated by a laser to excite the fluorophore and the emitted fluorescence is directed to the photodiode surface of the chip by a parabolic mirror [see e.g., FIGS. 17 & 18], and the emitted light detected and employed as described for the bioluminescence.

Since modifications will be apparent to those of skill in this art, it is intended that this invention be limited only by the scope of the appended claims.

Summary of Sequences of Representative Luciferases and the Reductase Set Forth in the Sequence Listing 1. SEQ ID NO. 1 *Renilla reinformis* Luciferase [U.S. Pat. No. 5,418,155]
2. SEQ ID NO. 2 *Cypridina hilgendorfii* luciferase [EP 0 387 355]
3. SEQ ID NO. 3 Modified *Luciola cruciata* Luciferase [firefly; U.S. Pat. No. 4,968,613]
4. SEQ ID NO. 4 Vargula (Cypridina) luciferase [Thompson et al. (1989) *Proc. Natl. Acad. Sci. U.S.A.* 86:6567–6571 and from JP 3-30678 Osaka
5. SEQ ID NO. 5 Apoaequorin-encoding gene [U S. Pat. No. 5,093,240, pAQ440]
6. SEQ ID NO. 6 Recombinant Aequorin AEQ1 [Prasher et al. (1987) "Sequence Comparisons of cDNAs Encoding for Aequorin isotypes," *Biochemistry* 26:1326–1332]
7. SEQ ID NO. 7 Recombinant Aequorin AEQ2 [Prasher et al. (1987)]
8. SEQ ID NO. 8 Recombinant Aequorin AEQ3 [Prasher et al. (1987)]
9. SEQ ID NO. 9 Aequorin photoprotein [Charbonneau et al. (1985) "Amino Acid Sequence of the Calcium-Dependent Photoprotein Aequorin," *Biochemistry* 24:6762–67711
10. SEQ ID NO. 10 Aequorin mutant with increased bioluminescence activity [U.S. Pat. No. 5,360,728; Asp 124 changed to Ser]
11. SEQ ID NO. 11 Aequorin mutant with increased bioluminescence activity [U.S. Pat. No. 5,360,728; Glu 135 changed to Ser]
12. SEQ ID NO. 12 Aequorin mutant with increased bioluminescence activity [U.S. Pat. No. 5,360,728 Gly 129 changed to Ala]
13. SEQ ID NO. 13 Recombinant apoaequorin [sold by Sealite, Sciences, Bogart, Ga. as AQUALITE®, when reconstituted to form aequorin]
14. SEQ ID NO. 14 *Vibrio fisheri* Flavin reductase [U.S. Pat. No. 5,484,723]

We claim:

1. A method of depositing silica on a matrix material, comprising:

isolating a silicalemma from a diatom or a cytokalymma from radiolaria;

transporting silicon into the silicalemma or cytokalymma to effect nucleation and epitaxial growth of silicon monomers in the silicalemma or cytokalymma; and effecting polymerization of silicon dioxide in the silicalemma or cytokalymma along an interface region of the matrix to form a matrix-silicate mesostructure.

* * * * *